(12) United States Patent
Keren et al.

(10) Patent No.: US 11,690,745 B2
(45) Date of Patent: Jul. 4, 2023

(54) ENDOLUMINAL SLEEVE GASTROPLASTY

(71) Applicant: Nitinotes Ltd., Caesarea (IL)

(72) Inventors: Dvir Keren, Tel Aviv (IL); Yekaterina Dlugach, Mabuim (IL); Irit Yaniv, Ramat-Gan (IL); Tamir Wolf, Haifa (IL)

(73) Assignee: Nitinotes Ltd., Caesarea (IL)

( * ) Notice: Subject to any disclaimer, the term of this patent is extended or adjusted under 35 U.S.C. 154(b) by 240 days.

(21) Appl. No.: 16/594,105

(22) Filed: Oct. 7, 2019

(65) Prior Publication Data
US 2020/0030130 A1 Jan. 30, 2020

Related U.S. Application Data

(63) Continuation of application No. 15/028,428, filed as application No. PCT/IL2014/050893 on Oct. 8, 2014, now Pat. No. 10,433,998.
(Continued)

(51) Int. Cl.
*A61F 5/00* (2006.01)
*A61B 17/04* (2006.01)
(Continued)

(52) U.S. Cl.
CPC ........ *A61F 5/0083* (2013.01); *A61B 17/0469* (2013.01); *A61B 17/0491* (2013.01); *A61B 17/062* (2013.01); *A61B 17/064* (2013.01); *A61B 17/068* (2013.01); *A61B 17/0644* (2013.01); *A61B 2017/00818* (2013.01); *A61B 2017/00867* (2013.01); *A61B 2017/00907* (2013.01); *A61B 2017/0608* (2013.01);
(Continued)

(58) Field of Classification Search
CPC .... A61F 5/0083; A61F 5/0086; A61F 5/0013; A61F 5/0003; A61B 17/062; A61B 17/0469; A61B 17/0491; A61B 17/068; A61B 17/064; A61B 17/0644; A61B 17/3468; A61B 2017/00867; A61M 25/007; A61M 2025/0018; A61M 2039/1224
See application file for complete search history.

(56) References Cited

U.S. PATENT DOCUMENTS

| 7,083,629 B2 | 8/2006 | Weller et al. |
| 7,520,884 B2 | 4/2009 | Swanstrom et al. |

(Continued)

FOREIGN PATENT DOCUMENTS

| CN | 102307530 | 1/2012 |
| CN | 202875401 | 4/2013 |

(Continued)

OTHER PUBLICATIONS

Official Action dated Feb. 24, 2020 From the US Patent and Trademark Office Re. U.S. Appl. No. 15/517,230. (16 pages).
(Continued)

*Primary Examiner* — Sarah A Simpson
*Assistant Examiner* — Raihan R Khandker

(57) ABSTRACT

Devices and methods of endolumenal formation of gastric sleeves are described. Some embodiments allow templating of a gastric sleeve by a gastric bougie, exposing a selected amount of tissue for suturing access, while maintaining sufficient internal working space for suturing within the template lumen.

25 Claims, 39 Drawing Sheets

Related U.S. Application Data

(60) Provisional application No. 61/889,099, filed on Oct. 10, 2013.

(51) Int. Cl.
*A61B 17/062* (2006.01)
*A61B 17/068* (2006.01)
*A61B 17/064* (2006.01)
*A61B 17/00* (2006.01)
*A61B 17/06* (2006.01)
A61B 17/08 (2006.01)
A61B 17/22 (2006.01)
A61B 17/30 (2006.01)

(52) U.S. Cl.
CPC .............. *A61B 2017/0641* (2013.01); *A61B 2017/06076* (2013.01); *A61B 2017/081* (2013.01); *A61B 2017/22069* (2013.01); *A61B 2017/306* (2013.01)

(56) References Cited

U.S. PATENT DOCUMENTS

| | | | |
|---|---|---|---|
| 7,896,890 | B2 | 3/2011 | Ortiz et al. |
| 7,918,869 | B2 | 4/2011 | Saadat et al. |
| 8,794,243 | B2 | 8/2014 | Deem et al. |
| 2003/0065359 | A1 | 4/2003 | Weller et al. |
| 2003/0208209 | A1 | 11/2003 | Gambale et al. |
| 2004/0158125 | A1 | 8/2004 | Aznoian et al. |
| 2005/0228504 | A1 | 10/2005 | Demarais |
| 2005/0261711 | A1 | 11/2005 | Okada et al. |
| 2005/0288688 | A1 | 12/2005 | Sakamoto et al. |
| 2006/0094929 | A1 | 5/2006 | Tronnes |
| 2006/0253126 | A1 | 11/2006 | Bjerken et al. |
| 2006/0253127 | A1* | 11/2006 | Bjerken ............ A61B 17/0482 606/139 |
| 2007/0032800 | A1 | 2/2007 | Ortiz et al. |
| 2007/0055292 | A1 | 3/2007 | Ortiz et al. |
| 2007/0073098 | A1 | 3/2007 | Lenker et al. |
| 2008/0249404 | A1 | 10/2008 | Mikkaichi et al. |
| 2008/0275473 | A1 | 11/2008 | Filipi et al. |
| 2008/0319470 | A1 | 12/2008 | Viola |
| 2009/0275960 | A1 | 11/2009 | Provenza et al. |
| 2010/0076440 | A1 | 3/2010 | Pamichev et al. |
| 2010/0076488 | A1 | 3/2010 | Spivey et al. |
| 2010/0185140 | A1 | 7/2010 | Kassab et al. |
| 2011/0098530 | A1 | 4/2011 | Yamane |
| 2013/0178698 | A1 | 7/2013 | Bender et al. |
| 2013/0178877 | A1 | 7/2013 | Bender et al. |
| 2014/0276333 | A1 | 9/2014 | Neisz et al. |
| 2015/0025550 | A1 | 1/2015 | Heneveld |
| 2015/0119905 | A1 | 4/2015 | Shluzas et al. |
| 2016/0250056 | A1 | 9/2016 | Keren et al. |
| 2017/0304099 | A1 | 10/2017 | Keren et al. |
| 2021/0000628 | A1 | 1/2021 | Keren et al. |

FOREIGN PATENT DOCUMENTS

| | | |
|---|---|---|
| EP | 1538965 | 9/2008 |
| JP | 2009-078158 | 4/2009 |
| WO | WO 2004/021873 | 3/2004 |
| WO | WO 2011/149891 | 12/2011 |
| WO | WO 2013/087096 | 6/2013 |
| WO | WO 2013/103998 | 7/2013 |
| WO | WO 2015/052720 | 4/2015 |
| WO | WO 2015/069506 | 5/2015 |
| WO | WO 2016/056016 | 4/2016 |

OTHER PUBLICATIONS

Notification of Office Action dated Dec. 10, 2019 From the State Intellectual Property Office of the People's Republic of China Re. Application No. 201580064414.3 and Its Summary in English. (4 Pages).
Translation dated Dec. 18, 2019 of Notification of Office Action dated Dec. 10, 2019 From the State Intellectual Property Office of the People's Republic of China Re. Application No. 201580064414. 3. (2 Pages).
Communication Pursuant to Article 94(3) EPC dated Oct. 12, 2020 From the European Patent Office Re. Application No. 15849674.5. (6 Pages).
Applicant-Initiated Interview Summary dated Nov. 7, 2019 From the US Patent and Trademark Office Re. U.S. Appl. No. 15/517,230. (3 pages).
Interview Summary dated Apr. 1, 2020 from the US Patent and Trademark Office Re. U.S. Appl. No. 15/517,230. (3 pages).
Notice of Reasons for Rejection dated Jun. 30, 2020 From the Japan Patent Office Re. Application No. 2017-538477 and Its Translation Into English. (8 Pages).
Applicant-Initiated Interview Summary dated Mar. 14, 2018 From the US Patent and Trademark Office Re. U.S. Appl. No. 15/028,428. (3 pages).
Communication Pursuant to Article 94(3) EPC dated Nov. 6, 2018 From the European Patent Office Re. Application No. 14851903.6. (7 Pages).
Communication Relating to the Results of the Partial International Search dated Jan. 25, 2016 From the International Searching Authority Re. Application No. PCT/IL2015/051009.
Examination Report dated Jul. 3, 2019 From the Australian Government, IP Australia Re. Application No. 2015329518. (2 Pages).
International Preliminary Report on Patentability dated Apr. 20, 2017 From the International Bureau of WIPO Re. Application No. PCT/IL2015/051009. (10 Pages).
International Preliminary Report on Patentability dated Apr. 21, 2016 From the International Bureau of WIPO Re. Application No. PCT/IL2014/050893.
International Search Report and the Written Opinion dated Mar. 3, 2016 From the International Searching Authority Re. Application No. PCT/IL2015/051009.
International Search Report and the Written Opinion dated Jan. 21, 2015 From the International Searching Authority Re. Application No. PCT/IL2014/050893.
Notice of Reasons for Rejection dated Aug. 6, 2019 From the Japan Patent Office Re. Application No. 2017-538477 and Its Translation Into English. (7 Pages).
Notification of Office Action and Search Report dated Nov. 2, 2018 From the State Intellectual Property Office of the People's Republic of China Re. Application No. 201580064414.3 and Its Summary in English. (10 Pages).
Notification of Office Action dated Jun. 5, 2019 From the State Intellectual Property Office of the People's Republic of China Re. Application No. 201580064414.3 and Its Summary in English. (7 Pages).
Official Action dated Jan. 8, 2019 From the US Patent and Trademark Office Re. U.S. Appl. No. 15/028,428. (20 pages).
Official Action dated Aug. 13, 2018 From the US Patent and Trademark Office Re. U.S. Appl. No. 15/028,428. (19 pages).
Official Action dated Aug. 21, 2019 From the US Patent and Trademark Office Re. U.S. Appl. No. 15/517,230. (43 pages).
Official Action dated Jan. 25, 2018 From the US Patent and Trademark Office Re. U.S. Appl. No. 15/028,428. (29 pages).
Official Action dated Mar. 26, 2019 From the US Patent and Trademark Office Re. U.S. Appl. No. 15/028,428. (7 pages).
Supplementary European Search Report and the European Search Opinion dated Jul. 25, 2017 From the European Patent Office Re. Application No. 14851903.6. (10 Pages).
Supplementary European Search Report and the European Search Opinion dated May 25, 2018 From the European Patent Office Re. Application No. 15849674.5. (10 Pages).
Translation dated Nov. 13, 2018 of Notification of Office Action and Search Report dated Nov. 2, 2018 From the State Intellectual Property Office of the People's Republic of China Re. Application No. 201580064414.3 (8 Pages).

(56) References Cited

OTHER PUBLICATIONS

Translation dated Jun. 18, 2019 of Notification of Office Action dated Jun. 5, 2019 From the State Intellectual Property Office of the People's Republic of China Re. Application No. 201580064414.3. (7 Pages).
Requisition by the Examiner dated Sep. 12, 2021 From the Innovation, Science and Economic Development Canada, Canadian Intellectual Property Office Re. Application No. 2,963,075. (19 Pages).
Official Action dated Jun. 23, 2022 from US Patent and Trademark Office Re. U.S. Appl. No. 17/026,345. (27 pages).
Requisition by the Examiner dated Sep. 16, 2022 From the Innovation, Science and Economic Development Canada, Canadian Intellectual Property Office Re. Application No. 2,963,075. (5 Pages).
Notice of Allowance dated Oct. 18, 2022 from the US Patent and Trademark Office Re. U.S. Appl. No. 17/026,345. (9 pages).

\* cited by examiner

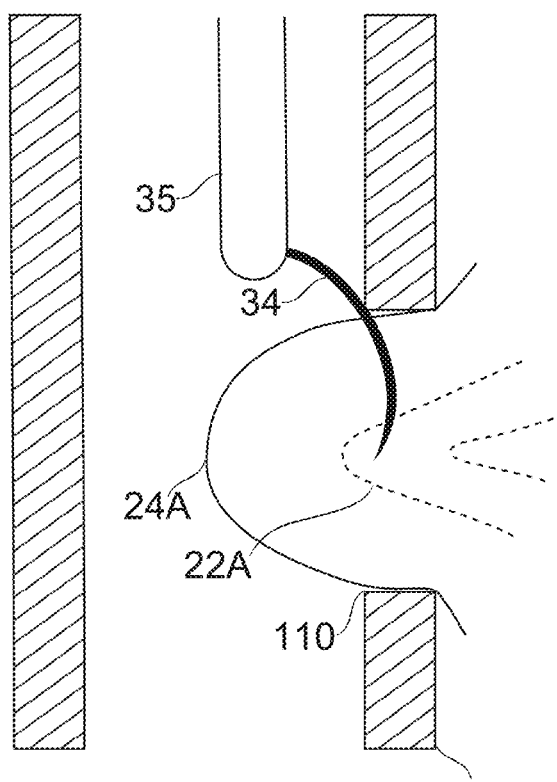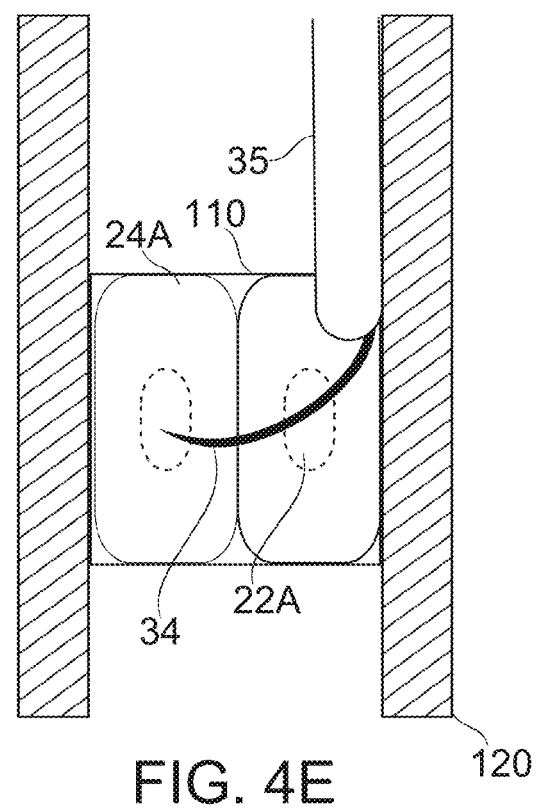

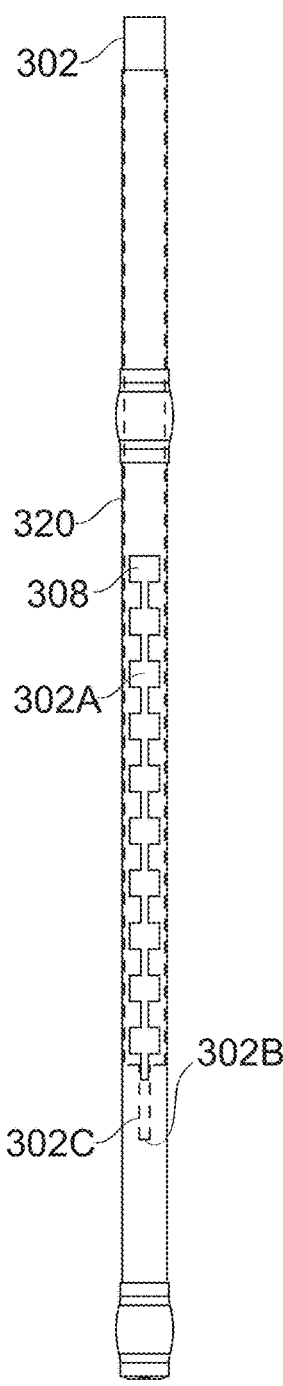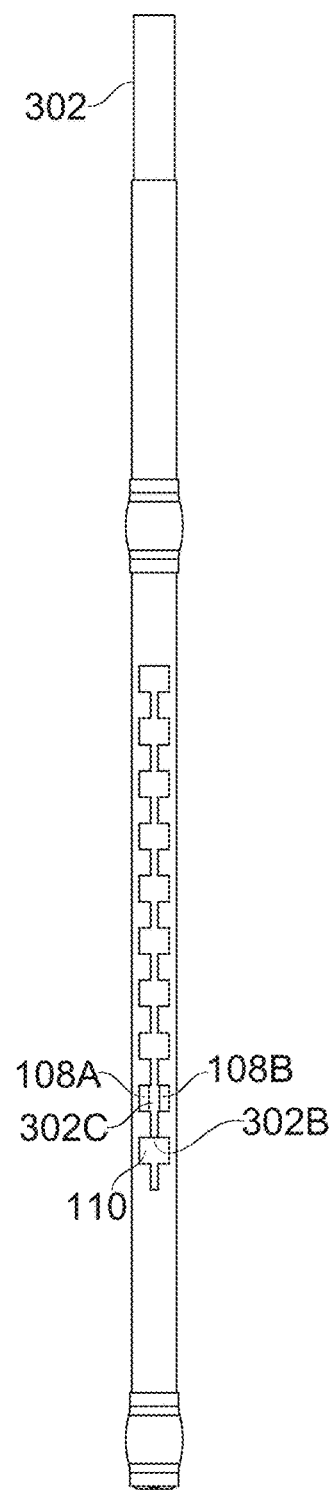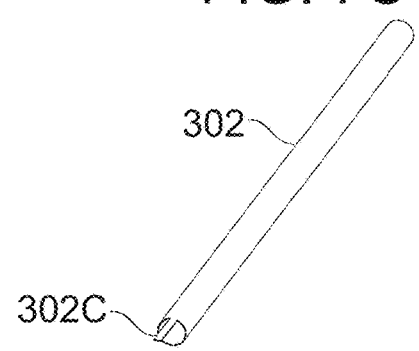
FIG. 7A  FIG. 7B  FIG. 7D
FIG. 7C

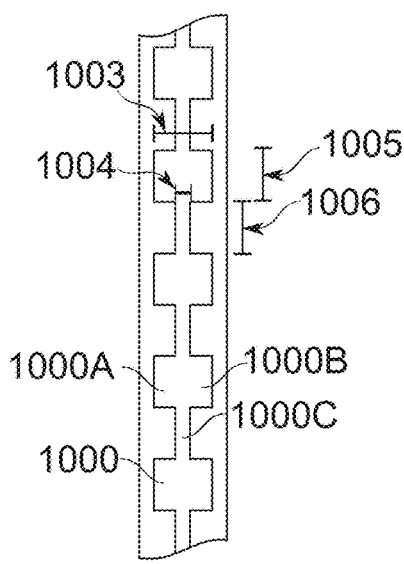
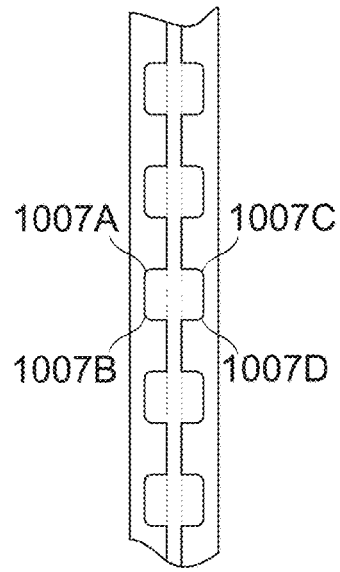
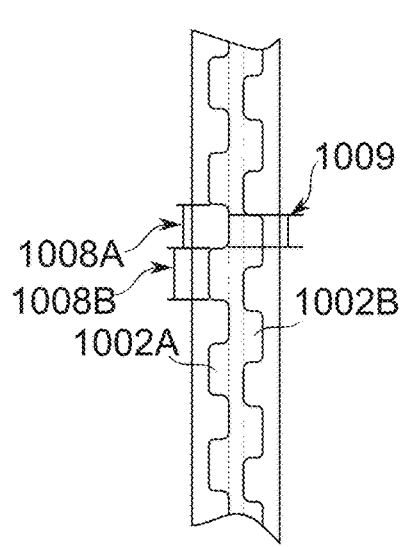
FIG. 10A  FIG. 10B  FIG. 10C
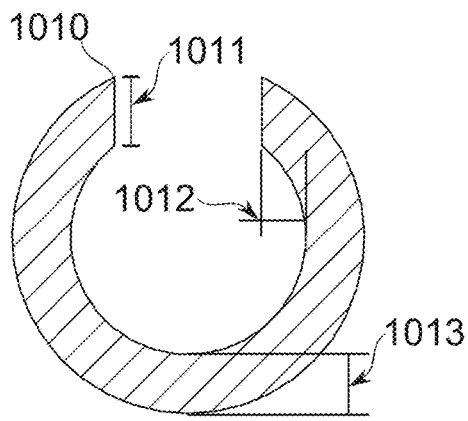
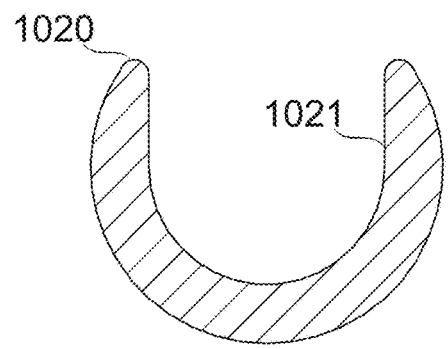
FIG. 10D  FIG. 10E
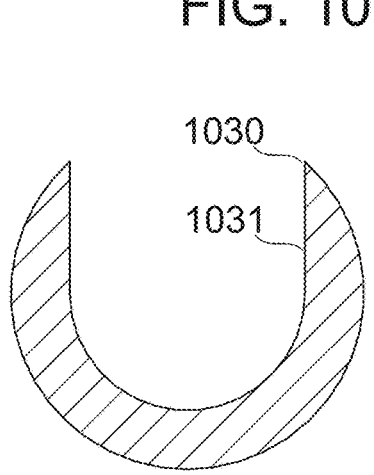
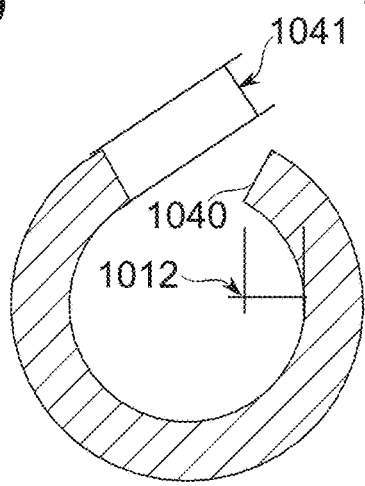
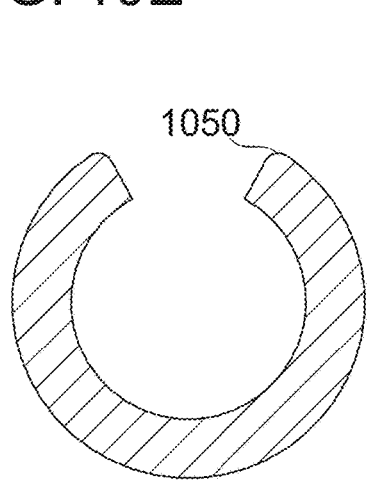
FIG. 10F  FIG. 10G  FIG. 10H

ENDOLUMINAL SLEEVE GASTROPLASTY

RELATED APPLICATIONS

This application is a continuation of U.S. patent application Ser. No. 15/028,428 filed on Apr. 10, 2016, which is a National Phase of PCT Patent Application No. PCT/IL2014/050893 having International Filing Date of Oct. 8, 2014, which claims the benefit of priority under 35 USC § 119(e) of U.S. Provisional Patent Application No. 61/889,099 filed on Oct. 10, 2013. The contents of the above applications are all incorporated by reference as it fully set forth herein in their entirety.

FIELD AND BACKGROUND OF THE INVENTION

The present invention, in some embodiments thereof, relates to the field of bariatric surgery and more particularly, to the endoluminal formation of gastric sleeves.

Obesity and related pathologies such as type 2 diabetes are of growing concern worldwide. Gastrointestinal weight-loss surgery (bariatric surgery) has been shown to be effective in achieving sustained weight loss and amelioration of type 2 diabetes. Gastric volume reductions via open surgical- or laparoscopic sleeve-gastrectomy have proven to be one of the most effective forms of treatment.

Any surgical approach, however, no matter how minimally invasive, will still struggle to meet demand due to the magnitude of this pandemic. Moderately obese patients, as well as vulnerable patients (children, for instance) are underserved patient populations. Procedural cost—which can reach tens of thousands of dollars in the US, for example—is also prohibitive in places worldwide.

Furthermore, surgical procedures themselves are not without risks. Complications such as procedure-related leak, severity of co-morbidities, and surgeon learning curve are but a few of the factors that have been, and will be, limiting extensive adoption of this approach.

In addition to being a relatively non-invasive form of gastric volume reduction procedure, endoluminal gastric sleeve formation carries the potential for reduced risk of leakage from the stomach. Because the stomach itself is optionally left intact, another potential advantage of an endoluminal technique over sleeve formation by surgical resection is reversibility, for example, in case of complications. Devices and methods for endoluminal gastric sleeve formation are described, for example, in: U.S. Patent Publication 2008/0249404 by Mikkaichi et al. filed Dec. 27, 2007; U.S. Pat. No. 6,558,400 to Deem et al. filed May 30, 2001; U.S. Pat. No. 7,896,890 to Ortiz et al. filed Mar. 1, 2011; and U.S. Pat. No. 7,083,629 to Weller et al. filed Aug. 1, 2006.

SUMMARY OF THE INVENTION

There is provided in accordance with some embodiments of the invention a bougie for shaping a stomach portion to receive sutures, comprising:

(a) a flexible wall sized and shaped to define a gastric passageway for food;

(b) a plurality of spaced wall fenestrations longitudinally distributed along the flexible wall, wherein a geometry of at least some of said fenestrations is modifiable while said bougie is in a stomach to receive a thickness of gastric muscle for suturing.

In some exemplary embodiments of the invention, said fenestrations are arranged so that a first fenestration receives tissue from one side of the stomach and a second fenestration receives tissue from a facing side of the stomach, when vacuum is applied to said first and second fenestrations. Optionally or alternatively, said wall defines a lumen, is sized for transoral insertion to a stomach, and is stiff enough to withstanding a vacuum pressure sufficient to collapse tissue of the stomach onto the flexible wall.

In some exemplary embodiments of the invention, said plurality comprises at least 8 fenestrations.

In some exemplary embodiments of the invention, said fenestrations are arranged in pairs at same axial locations.

In some exemplary embodiments of the invention, said fenestrations are arranged in alternating order on either side of a lien along said bougie.

In some exemplary embodiments of the invention, said fenestrations are defined as cutouts from said wall.

In some exemplary embodiments of the invention, said fenestrations each define a collar for guiding tissue ingress. Optionally, said collar extends radially away from a surface of said wall.

In some exemplary embodiments of the invention, said fenestrations are configured to receive an amount of gastric tissue suitable for non-penetrating suturing by maintaining at least an outside layer of said gastric tissue outside of an axial lumen defined by said wall.

In some exemplary embodiments of the invention, the bougie comprises a blocker, wherein said blocker, extends along the flexible wall such that it diminishes open area within at least one fenestration, and wherein said blocker is moveable to increase the open area of at least one selected fenestration and wherein the fenestrations are being sized and shaped, when said open area is increased, to admit a predetermined thickness of a gastric wall of said stomach for suturing. Optionally, said blocker bisects said open area into a plurality of open areas, each acting as a fenestration. Optionally, a first open area of said plurality of areas is positioned to receive a portion of said stomach tissue from a first portion of the gastric wall, and a second open area of said plurality of areas is positioned to receive a portion of said stomach tissue from a second portion of the gastric wall; the first and second portions of the gastric wall being connected through a band of gastric wall wrapping around the bougie.

In some exemplary embodiments of the invention, the blocker is moveable to selectively open said selected fenestration in an order from a more distal cutout region to a more proximal cutout region. Optionally, said blocker is configured to be so movable after suturing so as to release itself from gastric tissue sutured around it. Optionally, said blocker is in the form of a strip or a cylinder.

In an exemplary embodiment of the invention, the bougie comprises at least one fenestration having its entire area blocked by the blocker, the blocker being moveable to at least partially open the blocked area. Optionally, said blocker is moveable to increase the at least partially open blocked area to admit a predetermined thickness of a gastric wall of said stomach for suturing.

In some exemplary embodiments of the invention, said predetermined thickness allows insertion of a needle into said gastric wall to within a selected range of tissue depths.

In some exemplary embodiments of the invention, said fenestrations are arranged to guide uniform suturing along said stomach.

In some exemplary embodiments of the invention, said selected range of tissue depths is between 2 mm and 6 mm.

In some exemplary embodiments of the invention, said predetermined thickness is predetermined by a geometry of said fenestration.

In some exemplary embodiments of the invention, said fenestrations comprise periodic widenings of a cut away portion of the flexible wall along a longitudinal axis of the bougie. Optionally, said periodic widenings occur between every cm to 2.5 cm.

In some exemplary embodiments of the invention, said blocker occupies at least 20% of the width of the fenestrations it crosses.

In some exemplary embodiments of the invention, different ones of said fenestrations have different sizes when unblocked.

In some exemplary embodiments of the invention, an angular distance between a pair of fenestrations is between 20 and 50 degrees, a width of each of said pair is between 6 and 8 mm and said predetermined depth is between 1 and 2.2 mm, while leaving at least a serosa layer out of said bougie and a distance between the centers of axially separated fenestrations is between 0.7 and 1.2 mm.

In some exemplary embodiments of the invention, the bougie has a curved longitudinal axis in a resting state thereof.

In some exemplary embodiments of the invention, said fenestrations are arranged axially such that a longitudinally advancing needle can suture tissue in said fenestrations to each other and form a gastric sleeve therefrom.

In some exemplary embodiments of the invention, the bougie comprises at least two inflatable elements, one on either end of said bougie and configured to expand an amount sufficient to seal a stomach enclosing said bougie.

In some exemplary embodiments of the invention, the bougie comprises at least one shaping element radially extending away form said bougie and arranging a collapse of said stomach when vacuum is applied to said bougie. Optionally, said shaping element extends to a portion of said stomach opposite said bougie and applies a pushing force thereagainst.

In some exemplary embodiments of the invention, said bougie has an interior lumen large enough to allow the insertion of a 7 mm diameter videoscope for imaging said predetermined thickness of tissue.

In some exemplary embodiments of the invention, said blocker is transparent for optical imaging therethrough.

In some exemplary embodiments of the invention, the bougie is provided as a system including a suturing needle. Optionally, said needle is helical.

In some exemplary embodiments of the invention, the bougie is provided as a system including at least one non-thread suture.

In some exemplary embodiments of the invention, the bougie is provided as a system including at least axially retracting suture applicator.

In some exemplary embodiments of the invention, the bougie is provided as a system including a connection to a vacuum source and a leak indicator.

There is provided in accordance with some embodiments of the invention a bougie for shaping a stomach portion to receive sutures, comprising:

(a) a flexible wall sized and shaped to define a gastric passageway for food;

(b) a plurality of at least four spaced wall fenestrations longitudinally distributed along the flexible wall, wherein said plurality of fenestrations have a geometry adapted to guide a predetermined thickness of gastric muscle for suturing to be sucked into said fenestrations and held thereby.

There is provided in accordance with some embodiments of the invention a system for gastric reshaping including:

a bougie for shaping a stomach portion to receive sutures, comprising a flexible wall sized and shaped to define a gastric passageway for food; and a proximal expandable element and a distal expandable element spaced apart a distance suitable for sealing said stomach while vacuum is applied to said stomach via a fenestration in said bougie to collapse said stomach on said bougie. Optionally, the system comprises at least one sensor and circuitry receiving a signal from said sensor and configured to generate an alert when a leak in said stomach is indicated by said sensor. Optionally, said sensor detects a change in vacuum pressure in said bougie.

There is provided in accordance with some embodiments of the invention a bougie for shaping a stomach portion to receive sutures, comprising:

(a) a flexible wall sized and shaped to define a gastric passageway for food;

(b) a plurality of spaced wall fenestrations longitudinally distributed along the flexible wall and configured to receive a thickness of gastric muscle, from opposing stomach walls, for suturing; and (c) a tissue arranger positioned to control a collapse of said stomach when vacuum is applied to said fenestrations. Optionally, said arranger extends to a wall of said stomach opposite said bougie. Optionally or alternatively, said arranger arranges tissue near said fenestrations.

There is provided in accordance with some embodiments of the invention a method of gastric sleeve creation, comprising:

inserting bougie into a stomach;

applying a vacuum to collapse said stomach on said bougie; and detecting a penetration through said stomach wall, based on a change in one or more property of said vacuum. Optionally, applying comprises applying through a plurality of fenestrations in said bougie and also comprising receiving gastric wall tissue in said fenestrations and piecing said tissue n a non-penetrating manner which does not exit said stomach. Optionally or alternatively, said detecting comprises detecting change in said vacuum. Optionally or alternatively, the method comprises sealing said stomach using at least one sealing balloon.

There is provided in accordance with some embodiments of the invention a method of intralumenally suturing a gastric sleeve, comprising:

inserting into a stomach a bougie having a wall comprising a plurality of separated fenestrations;

drawing vacuum through said bougie, such that stomach tissue from opposing sides of the stomach is drawn to the bougie wall, wrapping around it, and partially intruding into said fenestrations, one such side in each portion of the bisected cutaway regions; and suturing the drawn tissue from two sides to each other, wherein a geometry of said fenestrations is modified before, during or after said suturing. In some exemplary embodiments of the invention, said fenestrations are separated by a strip and said suturing is around said strip and comprising withdrawing the blocker strip, freeing the sutured tissue. Optionally or alternatively, said fenestrations are selected to have a circumferential width of between about twice the combined thickness of a muscosa layer and a muscular layer and about twice the combined thickness of a muscosa layer, a muscular layer and serosa layer. Optionally or alternatively, the method comprises sequentially:

removing the partial block on said partially blocked cutaway regions such that the tissue from the two sides of the stomach wall intrudes more deeply into the bougie lumen, and suturing the more deeply intruding tissue from the two sides of the stomach wall together. Optionally or alternatively, said modifying comprises increasing a size of said fenestrations such that the tissue from the two sides of the stomach wall intrudes more deeply into the bougie lumen, prior to said suturing.

In some exemplary embodiments of the invention, the method comprises viewing said tissue from within said bougie prior to said suturing.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon. Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system.

In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings:

FIGS. 4D-4E schematically illustrate cutaway side-views of suturing from within a bougie, according to some exemplary embodiments of the invention;

FIGS. 7A-7D schematically illustrate a bougie configured with a blocker slider shaped to allow either full or partial blockage of positioning/suture windows, according to some exemplary embodiments of the invention;

FIGS. 10A-10M schematically illustrate, different dimensions of fenestrations, having different effects on function, according to some exemplary embodiments of the invention;

DESCRIPTION OF SPECIFIC EMBODIMENTS OF THE INVENTION

Figure 1A:
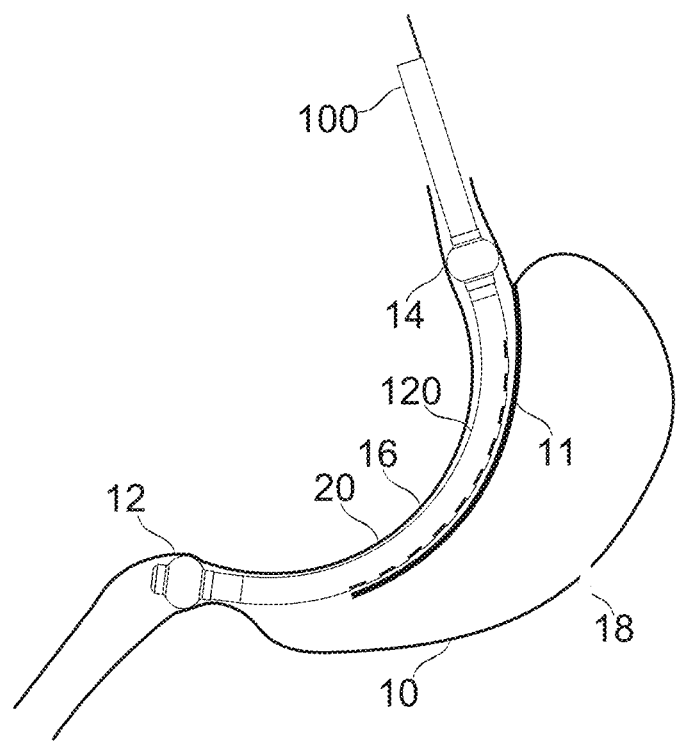
FIGS. 1A-1B schematically illustrate bougie-templated surgical formation of a gastric sleeve with partially isolated gastric pocket, according to some exemplary embodiments of the invention.

The present invention, in some embodiments thereof, relates to the field of bariatric surgery and more particularly, to the endoluminal formation of gastric sleeves.

Overview

A broad aspect of some embodiments of the current invention relates to devices and methods for the endoluminal formation of a gastric sleeve, for the control of patient weight and related health issues, optionally in a fast and/or reliable manner.

In some cases, for a method of endoluminal formation of a gastric sleeve to reach wide availability, it should be both rapid and reliable. Some proposed automated and semi-automated solutions for rapid formation envision "blind" formation of a gastric sleeve, where tissue is formed by vacuum to a putatively known location, so that a securing device can be driven through it along a predetermined pathway. Potential drawbacks of such approaches arise in the context of variable anatomy, incorrect initial positioning (in cases where this is difficult to verify), and/or movement during the procedure, even if positioning is initially correct. Some or all of these drawbacks may be avoided or mitigated using some embodiments of the invention.

The fine manipulations often associated with (thread-type) suturing suggest a potential for slowness and/or technical difficulty, given the confined space in which an endoluminal gastric sleeve must be created. A typical gastric sleeve diameter, for example, has a nominal diameter of about 12.5 mm, up to about 20 mm. In part to obviate the need for such suturing, attachment means alternative to surgical suture have been proposed for formation of a gastric sleeve, including surgical staples, helical wires, clips, and attachment cups.

One alternative is barbed ("knotless") sutures (whose resistance to breakage becomes more dependable). Barbed sutures potentially are more rapidly placed than traditional sutures, since the need for knotting is removed or reduced. Barbed sutures distribute stress more evenly along their length, potentially reducing the occurrence of focal tearing of tissue. Barbed sutures are more easily placed in confined surgical situations. In some cases it may be desirable for a practitioner to be able to clearly visualize the work area, for example by the use of an endoscope (typically, a video scope-type endo scope).

Another suturing solution exists in the form of endoscope-mounted suturing machines. However, the endoscope itself can be more than 1 cm in diameter, for example, to allow repositioning thereof and a suturing machine adds further bulk.

In an exemplary embodiment of the invention, there is provided methods and/or apparatus for endoluminal sleeve gastroplasty, for creating controllable, well-defined, and/or verifiable conditions for the guidance of sleeve formation that are also optionally consistent with providing enough space for the use of sutures and suture-like attachment technologies, though it is noted that some embodiments do not use sutures. It should be understood that one or more of the elements of control, definition and verification are optionally used with other forms of attachment, such as staples, pins, clips, helical inserts, tissue adhesives, and/or other devices. Except where features relating specifically to suturing as such are described herein, it is to be understood that references to suturing are exemplary and not limiting, and include reference also other forms of tissue connection as well.

An aspect of some embodiments of the current invention relates to the provision of adaptable fenestrations, and methods for the use thereof, which allow and/or support controlled, optionally variable, gastric wall intrusion into a bougie adapted to form a template for a gastric sleeve.

In some embodiments, a bougie (e.g., a form of medical device comprising a hollow body which is generally cylindrical), with a size and flexibility appropriate for insertion transorally into the gastric cavity, is adapted for use as a template for the formation of a gastric sleeve, for example, based on its size, shape and/or other properties, including dynamic properties, as described herein. Bougie-templating is used in different forms of gastric reduction, including sleeve formation by gastrectomy. Some embodiments of the invention comprise bougie modifications which add new functions to this common element of gastric reduction.

In some embodiments, the bougie is provided with one or more openings to which vacuum is applied (for example from outside the stomach), causing the stomach walls to collapse around it. Optionally, if the Bougie is cylindrical, the collapse is generally cylindrical, at least over most of a circumference of the bougie. Optionally, the bougie includes one or more elements to seal some or all of the stomach so the vacuum does not "escape" via other parts of the GI system and/or other openings in the stomach.

In some embodiments, endoluminal access to the walls is provided through specialized apertures, related to herein as fenestrations.

In some embodiments, fenestrations are configurable in geometry (e.g., cross-sectional shape, connectivity and/or size and/or geometrical relation between two or more fenestrations) during formation of a gastric sleeve to select among at least two states. In some embodiments, a wall positioning state of a fenestration holds gastric wall tissue in a position consistent with "gastric sleeve templating", but prevents it from materially interfering with manipulation and/or visualization of tissue distal to it. A suture presentation state, in some embodiments, allows tissue to intrude into the bougie to a distance which presents a profile for suturing. In some embodiments, suturing or other attachment ties the bougie together with the tissue of the stomach in a suture presentation state, while entry into a third and/or alternative state, a suture-freeing state, breaks this connection, freeing the bougie from connection with the stomach. In some embodiments, the position of the blocker is the same for two or more states (for example, the positioning state and the suture presentation state are the same). In some embodiments, the transition among states, and/or configuration of the state itself is gradually selectable; for example, a fenestration size is gradually adjustable from a fixation/positioning state to select a desired tissue penetration depth for presentation of tissue for suturing in a suture presentation state. In some embodiments, a tissue exclusion state entirely prevents the intrusion of gastric wall tissue to the bougie at the level of a fenestration, until a selected stage of the sleeve formation procedure. In an exemplary embodiment of the invention, fenestration geometry (e.g., in a circumferential direction and/or axial direction) for presentation for suturing is between 2*(ML+GM) and 2*(ML+GM+SL), where ML is a thickness of the muscosa layer, GM is a thickness of the gastric muscle layer and SL is a thickness of the serosa layer. The geometry may be different, for example, be up to 20% greater or smaller (or more), for example, if a collar surrounds the fenestration.

In some embodiments, the transition between states is accomplished by the movement of a blocker device, which selectively blocks and unblocks portions of the fenestrations. In some embodiments, the blocker device—alternatively or additionally-divides fenestrations into two or more parts, creating an effective reduction of size which also serves as a form of blocking. In some embodiments, there are two modes of state transition—transition of size, in which fenestrations are made larger or smaller, and "topological" transition, wherein two or more separated fenestrations merge, or a single fenestration aperture is divided. In some embodiments, only one of these modes is used. In some embodiments, transition involves compound movements and transitions—for example, merging two windows across a short slit opening to free a suture by passing it through the slit, then re-dividing the windows for exclusion of tissue from the bougie lumen.

A blocker device, in some embodiments, comprises, for example, a strip, tube, helix, and/or other part, attachedly insertable with, and also suitable for movement relative to the body of the bougie. The blocker optionally comprises a single piece, or two, three, or more pieces capable of such relative motion. A blocker is moved, for example, by axial translation along the bougie, and/or a form of lateral movement, such as rotational movement within or around the bougie.

In some embodiments, a blocker device is initially positioned to convert an array (for example an axially distributed row) of fenestrations to vacuum ports, suitable for grabbing and positioning portions of the gastric wall near to one another in preparation for suturing. In some embodiments, the ports in vacuum-port mode prevent intrusion of tissue into the bougie lumen, the prevention being to the extent necessary to allow visualization of portions more distal, while still forming a vacuum connection.

In some embodiments, a blocker device is re-positionable to convert fenestrations (for example, a pair of divided fenestrations at a time) into a suture-presenting mode. In a suture-presenting mode, a fenestration allows entry of tissue, for example under vacuum pressure, such that a depth of tissue is presented into which a suture needle or other attachment device can be reliably inserted to within a selected range of tissue depths.

In some embodiments, suture-presenting mode and vacuum-port mode are the same for a fenestration pair, the blocked fenestration dimensions being sized and shaped for correctly measured intake of tissue for suturing while the blocker is in place (rather than afterward). This can be for all fenestrations of the bougie, or with some fenestrations being differently seized, e.g., being properly sized for presentation of tissue for suturing upon blocker removal. Additionally or alternatively, the suture-presenting and vacuum-port modes can be the same for some fenestrations/usage scenarios (for example, in patients and/or locations where gastric wall tissue is relatively thin), and separately selectable for others (for example, in patients/locations where gastric wall tissue is relatively thick).

In some embodiments of the invention, removal of a blocker comprises entry into a suture-freeing mode. Optionally, a blocker is left in place during suturing, such that a suture joins two parts of stomach wall around the blocker itself. For example, that the suture is placed between the blocker and another portion of the bougie to which it joins, temporarily locking stomach and bougie together. In some embodiments, removal of the blocker by sliding through the sutured region frees the bougie from the sutured stomach.

It is noted that in some embodiments, at a single time, different fenestrations can be in different states, for example, due to partial retraction of the blocker.

In some embodiments, the fenestrations are not in parallel pairs. For example, here may be alternating pairs and/or pairs with only partial, or no axial overlap. In some embodiments, the fenestrations are arranged along a line, but the line is curved and/or is not in a single plane. This may allow not cylindrical sleeves to be created. Optionally or alternatively, the bougie itself is curved, optionally in more than one direction and/or its axis does not lie in a single plane.

An aspect of some embodiments of the invention relates to fenestration geometry which encourages a correct penetration depth. In some embodiments, the selected presentation depth is configured (e.g., by design and/or manipulation during use and/or selection from a range of bougies and/or bougie inserts such as in the shape of a thin slotted cylinder) to be dependably within a range which both assures access to the relatively tough muscular layers of the gastric wall (normally buried under 1-3 mm or more of mucosa and submucosa), and helps avoid penetration of a needle (or other suturing tool) past the muscular layer and/or serosa to perforate the gastric wall. It should be understood that the muscular layers themselves are typically only 1-3 mm thick themselves, so the degree of tissue intrusion allowed is potentially a critical parameter for reliable success.

In some embodiments, proper positioning comprises selection of one or more of fenestration size, bougie wall diameter, bougie wall thickness, and/or blocker size, according to a working level along the bougie axis. Typically, the anatomy of the stomach wall is variable along this dimension, being often thickest near the cardia, and growing thinner near the pylorus. In some embodiments of the invention template dimensions which vary as a function of this anatomy, such that reliable suturing can be performed to reduce risk of tearing (too shallow a suture) and/or perforation (too deep a suture). In some embodiments, presentation is controlled by not allowing penetration to be too deep, due to tissue exclusion from the bougie. In some embodiments, presentation is controlled by allowing tissue depths to be judged, for example, according to landmarks and/or scaling indications visible on the bougie in the working region of the tissue. In some embodiments, presentation is controlled by adding channels and/or restrictions to the positioning of a needle or other attachment device. For example, a channel is cut into a portion of the fenestration wall into which a needle or other fastening device is slotted so that it passes across the fenestration at a defined position, angle, and/or depth. Additionally or alternatively, an eye or lumen (optionally having a broken circumference to allow thread release) is provided for passage of needle therethrough. In some embodiments, a guide channel is continuous along the bougie and/or continuous between fenestration levels; for example, a spiral track passing from level to level along a portion of the length of the bougie. Such a track optionally is broken across a fenestration, but self-aligned so that it is easily found again upon crossing from one side to the other. In some embodiments, provision is made so that a needle or other leading edge of a fastening member can be driven continuously along such a track. Optionally, driving along the track is performed under endoscopic visualization, such that positioning of tissue at each fenestration is potentially verifiable before suturing occurs.

In some embodiments, an overall fenestration width is, for example, 6-8, 8-10 mm, 9-13 mm, 11-15 mm, 14-17 mm, or another greater, larger, or intermediate width. In some embodiments, fenestrations are axially joined to one another through a joining aperture, having a width of, for example, 1-2 mm, 2-4 mm, 3-5 mm, or another greater, larger, or intermediate width. Optionally, the fenestrations are defined by widenings occurring between such joining apertures. In some embodiments, fenestrations are separated axially. In some embodiments, fenestrations are separated axially by, for example, 4-10 mm, 9-13 mm, 11-15 mm, 14-17 mm, or another greater, larger, or intermediate length. In some embodiments, the axial length of fenestrations is, for example, about 4-9 mm, 8-10 mm, 9-13 mm, 11-15 mm, 14-17 mm, or another greater, larger, or intermediate axial length. In some embodiments, the lateral (most separated) fenestration boundaries are separated, for example, by at an angle of about 20°-30°, 25°-40°, 30°-45°, 40°-60°, 50°-80°, 75°-90°, or another greater, smaller and/or intermediate angle.

A consideration which potentially constrains, in some embodiments of the invention, the period between fenestrations is the interval for suturing. In a gastric sleeve where a non-food filling pocket is to be retained afterward, the sutures need be close enough together to prevent the passage of stomach contents, such that the sleeve forms a distinct compartment. A spacing of about 2 cm is generally sufficient to ensure this, though a different spacing is also used in some embodiments: for example, 1-1.3 cm, 1.3-1.5 cm, 1.5-2.5 cm, 2.3-3.0 cm, 1.0-2.5 cm, or another larger, smaller, or intermediate suture spacing. In some embodiments, an upper or lower region of the stomach is left unsutured, which, for example, allows secretions of the isolated stomach pocket to continue to enter the lower digestive tract and/or otherwise leave the stomach, even though the isolated region is kept substantially empty of food contents. A potential benefit of a lower opening is that it may prevent undesired food ingress into the pocket and/or may support stomach peristalsis. Optionally or alternatively, it may allow food to exit such a pocket by gravity and/or peristalsis. The provision of an opening may allow reversing of the operation, if desired.

In some embodiments, notionally single-aperture fenestrations having dimensions, for example, as just listed, are divided into two apertures during some portion of gastric sleeve formation by a blocker device, for example a blocker comprising a strip running through the center of the fenestration. In some embodiments, the blocker is just wide enough to comprise a stable divider, for example, 1 mm wide, or potentially less. Potentially, such a fine divider serves primarily to resist filling of a single fenestration by only one of the two gastric walls which are to be approximated. In some embodiments, the blocker is wider: for example, 2 mm, 3 mm, 4 mm, 5 mm, or another greater, smaller, or intermediate width. Wider blockers serve, for example, to prevent deep intrusion of tissue into the bougie during a portion of the gastric sleeve formation procedure. In some embodiments, a blocker width varies along the axis of the bougie, for example through a width difference of up to 2 mm, 3 mm, 4 mm, or another greater, smaller, or intermediate range of variability. A potential advantage of variable width is to allow adjustment to different thickness and/or convolution of the gastric wall along the axial extent of the bougie. In some embodiments, the blocker extends across at least 20% of the total width of a fenestration that it obstructs. In some embodiments, it extends across, for example, at least 30%, 40%, 50%, 75%, 90%, or another greater, smaller, or intermediate fraction of the width of a fenestration it crosses. In some embodiments, a blocker entirely blocks a fenestration it crosses. In some embodiments, a blocker defines the angle of arc separating two fenestrations. For example, fenestration medial sides (on either side of a blocker) are separated by an angle (measured from the center of the bougie lumen, for example) of from about 0°-10°, 5°-20°, 10°-25°, 20°-30°, or another greater, smaller and/or intermediate angle.

A potential problem for suturing through fenestrations of a bougie is management of the topological issue of "sewing in" the bougie to the suture line or locking by another connection means. In some embodiments, a blocker device is removable from a fenestration, either before suturing (which prevents the problem in the first instance), or after suturing (for example, by sliding the blocker device axially out of a suture in which it was originally involved). A potential advantage of the suture-then-remove approach is that the blocker device, while it remains in place, assists in stabilization of the suture line, even if the vacuum pressure should be deliberately or accidentally released. Potentially, it allows positioning and/or presentation for suture to be determined and set simultaneously, before suturing begins.

In some embodiments, for example as mentioned herein, a fenestration mode is provided, wherein a fenestration is entirely blocked by a blocker during a portion of the procedure. This is a potential advantage, for example, to reduce the period of time spent under high vacuum by portions of tissue which are to be sutured. Another potential advantage is to allow positioning to be adapted over the course of the procedure, by gradually "zipping up" the stomach wall from an initial start point. In some instances, this is potentially an easier way of capturing the stomach wall than following an initial requirement to capture the whole extent of the two opposing walls at once before suturing begins. Potentially, the choice between the two types of procedure is made at the onset of the surgery, and/or the choice can be to compromise between them—for example, to capture first a portion of each wall, then "zip up" the rest of the way once a stable base is established.

A potential advantage of some embodiments of the invention is when the device and/or method to be adaptable to variable conditions of the stomach of different patients, and/or the preferences and/or experience level of different practitioners. It is also envisioned that the techniques of endoluminal sleeve gastroplasty will continue to evolve over time, and it is a potential advantage for use of a device to be adaptable according to the specific requirements of a sleeve formation method.

In some embodiments, positioning of the stomach and/or the bougie is aided by the use of one or more positioning braces, configured to be inserted through and extendable from the bougie body. In some embodiments, the positioning brace comprises a preformed nitinol (or other super elastic or shape memory material) strip, inserted through a channel in the bougie, which returns to its preformed shape once inside the stomach, to push on it so that the gastric sleeve channel is properly formed upon application of vacuum, and/or so that the bougie ends are properly positioned laterally within the stomach.

In some embodiments, a bougie is provided with inflatable balloons on one or both ends, which convert the gastric lumen into a vacuum-sealed compartment when inflated. In some embodiments, one balloon inserts into the pylorus, or an adjacent region, such that suction does not bring any gas or fluid back from the intestines. In some embodiments, a balloon inserts into the region of the esophagus, and/or the cardia, such that suction does not bring any gas down through the esophagus. In some embodiments, the amount of (gauge pressure) vacuum applied to secure the gastric wall tissue, and/or to pull an appropriate measured amount of gastric wall tissue into the fenestrations of the bougie is about 0.1-0.2 bar, about 0.2-0.4 bar, about 0.3-0.5 bar, about 0.4-0.6 bar, or another range of pressures having the same, larger, smaller, and/or intermediate bounds. In some embodiments, pressure is stabilized to within a range of about ±0.05 bar once sealing is applied. In some embodiments, pressure is stabilized to within a range of about ±0.01 bar, ±0.03 bar, ±0.08 bar, ±0.1 bar, or another range of larger, greater, or intermediate pressures.

An aspect of some embodiments of the invention relates to a method of detecting inadvertent tissue penetration during an endoluminal gastroplasty procedure.

In some embodiments, a bougie provided with both pyloric region and esophageal/cardia region sealing stabilizes the vacuum pressure within a bougie to such a degree that even a small leak (and/or a sudden change in pressure/flow) is detectable (e.g., using a pressure sensor coupled to the vacuum source and/or line to bougie and a controller and/or using an alert system, for example an audio or visual alarm to alert a practitioner. Optionally, vacuum pressure is monitored during a procedure, and a change in pressure alerted to a practitioner as a potential leak. In some embodiments, pressure is maintained by feedback, and a change in flow through a vacuum-maintaining apparatus detected, triggering an alert.

A potential advantage of the method is to allow immediate and/or at-will detection of leakage conditions during a gastroplasty procedure, such that corrective measures can be undertaken. In particular, it is a potential advantage to have such information available as each suturing movement occurs, as this may be more likely to allow rapid localization of the problem for corrective action. In some embodiments, detection of pressure change is sensitive to leakage to within a range of about ±0.001 bar, ±0.005 bar, ±0.01 bar, ±0.05 bar, or another range of larger, greater, or intermediate pressures.

An aspect of some embodiments of the invention relates to the provision of a linear array of attachment points for defining the attachment line of a gastric sleeve.

In some embodiments, a flexible chain of links is provided, with attachment means (for example hooks) provided along the chain of links. In some embodiments, the chain (in one or two parts) is attached along either side of the prospective attachment line between the two walls of the planned gastric sleeve. In some embodiments, the two gastric wall sides are attached by impaling a portion of the gastric wall on hooks or barbs presented by the linear array device. In some embodiments, the linear array of attachment points presented comprises defined suturing holes, or another surface for receiving an attachment device such as a hook, helix, clip and/or staple.

In some embodiments, the two parts of the linear array are configured to self-attach along the attachment line that closes the gastric sleeve. For example, the device comprises complementary attachment mechanisms along the sleeve, wherein each link is attachable to a corresponding link on the opposite wall of the sleeve. In some embodiments, attachment is formed by pulling two ends of the attached device together, with the attachment forming automatically by interlocking. It is a potential advantage for the device to be self-locking, since this allows the device to be positioned so that it ends up on the outside of the gastric sleeve, away from the process of food digestion.

An aspect of some embodiments of the invention relates to the provision of a self-attaching clip or staple, which is naturally "closed", but which is held open until both walls of the stomach are put into position. Optionally, the clip is formed of nitinol, or another shape memory material. In some embodiments, a row of clips is provided, held in an open position by a clip holder device. Optionally, vacuum is applied to apertures of the clip holder, which tends to draw tissue close to the clip ends. Optionally, the clip ends are sharpened and/or barbed, to promote attachment to tissue which is drawn over them. In some embodiments, the clips, once attached to each gastric wall, are allowed to bend to their natural position, securing the wall. A potential advantage of self-securing clips is that the force of final closure need not be brought to bear externally, which is appropriate to the cramped conditions of gastric sleeve formation.

An aspect of some embodiments of the invention relates to the provision of a suturing device configured to drive a needle in a predefined path around a helical pathway, the pathway being partially interrupted at intervals for the infilling of gastric wall tissue. In some embodiments, infilling of gastric wall tissue is promoted by the application of vacuum, for example, via apertures of the helical pathway.

In some embodiments, the needle is driven by interacting along its length with a ratchet mechanism, which presses on one or more protrusions from the needle to drive it around the helical pathway. In some embodiments, the needle comprises a length which is relatively short compared to the length of the helical pathway it traverses. For example, the length of the needle is sized to follow two circuits of the helical pathway, one circuit, half a circuit, a third of a circuit, a quarter of a circuit, or another greater, lesser, or intermediate length. In some embodiments, the needle is driven by interactions at a plurality of regions along its length, such that it can continue to be driven from behind the entrance side of tissue it enters until a portion of the needle exits the tissue. At the exit side, the needle is picked up for advancement by interaction of the drive mechanism with the exiting portion of the needle, so that needle is advanced from in front of the tissue, while the back portion of the needle continues the passage through the tissue. In some embodiments, the needle is attached to a suture line, which is drawn by the needle along the course of its helical path. In some embodiments, parts of the suturing device are withdrawn from within the suture line, and the suture line tightened in order to form the final suture line of the gastric sleeve.

An aspect of some embodiments of the invention relates to a bougie having an array of fenestrations on each side of a line therealong and also including a removable element which extends away from the bougie to help manage the stomach collapse towards the fenestrations. In some embodiments, the removable element comprises one or more baffles, optionally mounted on a movable blocker such as described herein and optionally arranged to guide stomach tissue that is near the fenestrations to be on one side of the line or another. Optionally or alternatively, the movable element comprises an elongate element which extends away from the bougie in a curved manner to engage a distant part of the stomach and push it away from the bougie.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Bougie with Mutable Fenestrations

Figure 1B:
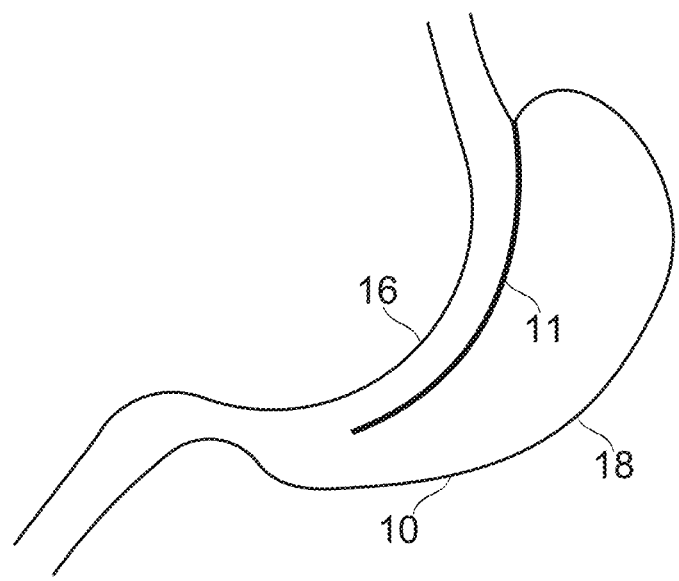
Figure 1C:
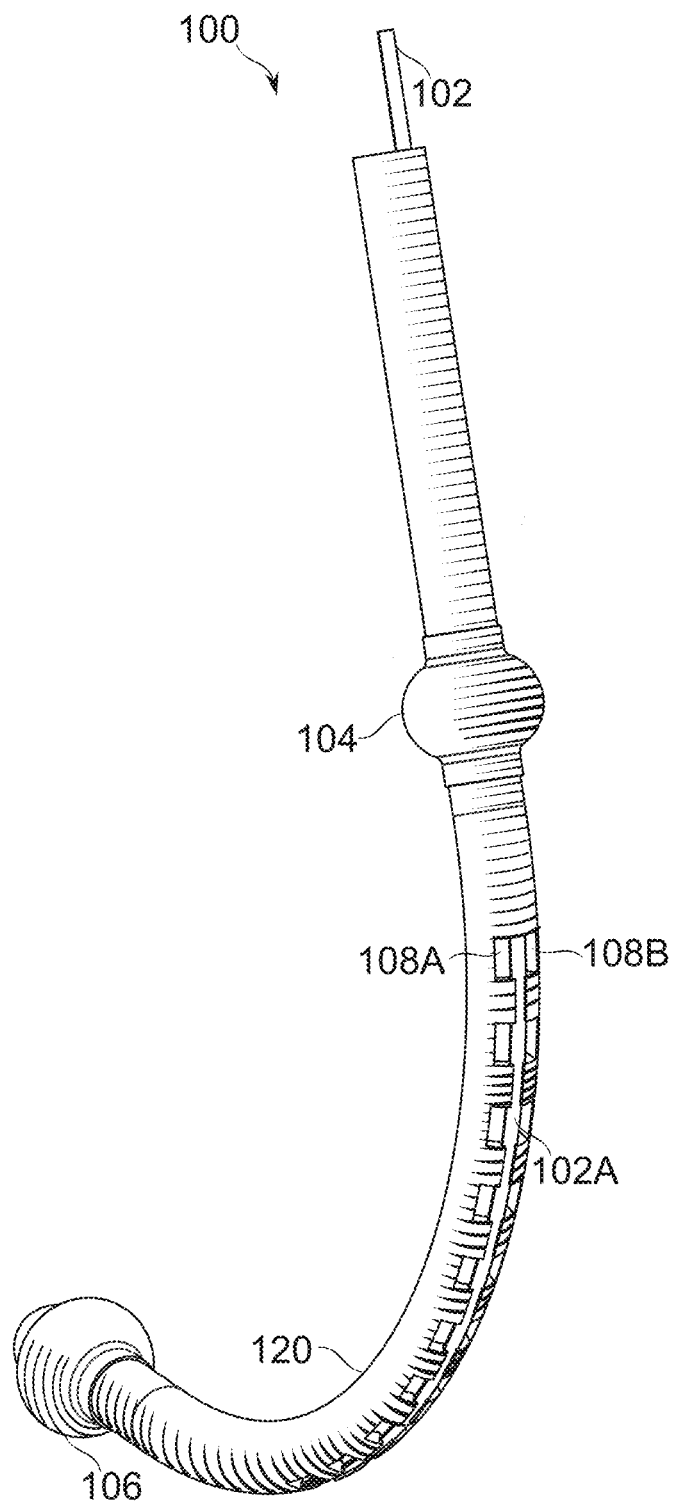
FIG. 1C schematically illustrates an exemplary bougie for use in creating a gastric sleeve, according to some exemplary embodiments of the invention.

Reference is now made to FIGS. 1A-1B, which schematically illustrate bougie-templated surgical formation of a gastric sleeve 16 with partially isolated gastric pocket 18, according to some exemplary embodiments of the invention. Reference is also made to FIG. 1C, which schematically illustrates an exemplary bougie 100 comprising mutable fenestrations 108A, 108B, according to some exemplary embodiments of the invention.

In some embodiments, fenestrations 108A, 108B are selectably mutable to perform various functions during the creation of a gastric sleeve 16. The functions include, for example, securing and/or releasing gastric wall tissue 20; and/or controlling gastric wall tissue exposure to suturing tools within the bougie, for creation of a gastric sleeve. In some embodiments, fenestrations 108A, 108B comprise fenestrations having width, height, thickness, and/or spacing selected and/or selectable to expose a chosen thickness of gastric wall tissue within the bougie (in particular, under application of vacuum to the bougie), according to the requirements of a particular stage and/or position of gastric sleeve formation. In some embodiments, fenestration dimensions are changeable, for example by the movement of a blocker 102 or other spacing structure. In some embodiments, fenestration topology/connectedness is changeable by the movement of a blocker 102 or other framing structure. In some embodiments, different fenestrations are sized, spaced, and/or adjustable differently. This provides a potential advantage to adapt, for example, to variations in thickness and other anatomical features of the gastric wall along the length (the longitudinal axis) of the bougie 100.

In some embodiments of the invention, a bougie 100, sized for esophageal insertion (for example, 11-20 mm in diameter), is inserted into a stomach 10. In some embodiments, the bougie assumes a curve through its body 120 which follows the curving anatomy of stomach 10 extending from the cardia at the base of the esophagus 14 to the region of the pylorus 12. Vacuum is applied to wrap bougie 100 within the portion of stomach wall which is to form a gastric sleeve 16. Optionally, wrapping brings the walls together at approximation line 11. In some embodiments, attachment along approximation line 11 is performed to make a gastric sleeve; for example, by suturing. In some embodiments, bougie 100 is comprised of a polymer allowing sufficient flexibility for insertion. In some embodiments, the polymer is transparent, providing a potential advantage for visualization during positioning and/or suturing. Exemplary materials for construction include, for example, polyethylene, cyclic olefin copolymer, polycarbonate, polyolefin, polyurethane, fluorinated ethylene propylene, polyethylene and/or terephthalate. In some embodiments, the flexibility of the bougie body is about 50-60 Shore A, about 55-65 Shore A, about 50-80 Shore A or another range of flexibilities having the same, larger, smaller, and/or intermediate bounds. In some embodiments, different sections of the body have different flexibilities; for example, short regions can be stiffer if separated by more flexible regions allowing transoral passage of the bougie. In some embodiments, the bougie comprises links of two or more materials, for example, metal regions (which offer the potential advantage of added resistance to collapse under vacuum pressure), and plastic and/or rubber regions (providing flexibility). In some embodiments of the invention, the bougie comprises extruded polymer material.

In some embodiments, bougie 100 comprises fenestrations 108A, 108B distributed along a side of bougie body 120 away from the inner curve of the stomach 10. Fenestrations 108A, 108B comprise, when inserted to the stomach, avenues of communication between the walls of the stomach and a working lumen of the bougie. In particular: fenestrations 108A, 108B provide one or more functions simultaneously and/or at different times during formation of a gastric sleeve. These functions are first described in general outline; other specifics are described in relation to the particular embodiments presented herein.

1. Fenestrations, in some embodiments, optionally function as ports through which suction, exerted upon the lumen of the bougie, can be applied for positioning and/or fixation of portions of the gastric wall. In particular, in some embodiments, there are two rows of fenestrations 108A, 108B located alongside each other on the outer curve of the bougie body 120. Optionally, the fenestrations define an approximation line 11 to which a portion of each of the two opposite walls of the stomach 10 is brought in preparation for more permanent attachment, for example by suturing. In some embodiments, other fenestrations (located, for example, around the body of the bougie 100) also serve as vacuum ports. In some embodiments, balloons 106, 104 are located along the body of the bougie 100 at places such that can be inflated to seal against the entry of gasses from the pylorus 12 (balloon 106) and/or the esophagus 14 (balloon 104) when vacuum is pulled. Potentially, this prevents leakage, stabilizing the vacuum. Potentially, this in turn helps stabilize the positioning of tissue pulled against the fenestrations 108A, 108B of the bougie 100 by vacuum.

2. Fenestrations optionally function as view ports, allowing the observation and/or alignment of the arrangement of stomach walls against the bougie. For example, a crease line formed where two gastric walls approximate to each other is observed through the fenestrations. In some embodiments, at least a portion of the bougie wall is transparent, so that visualization is not limited to through the fenestrations. Nevertheless, the fenestrations optionally serve as alignment guides, particularly insofar as a usual goal during positioning is to move and/or verify the crease defining the line of approximation to lay between the two rows of fenestrations 108A, 108B, such that one wall is drawn to the fenestrations of the left row, and the other to the right.

3. Fenestrations, in some embodiments, optionally function (for example, according to their size and/or shape) to limit the lumenal intrusion of tissue sucked to the bougie upon application of vacuum, for as long as this limitation is needed. In some conditions, gastric wall pulled into apposition with a fenestration by suction is prevented from intruding (or from intruding deeply) to the lumen of the bougie by the small size (in at least one dimension) of the fenestration. This is a potential advantage for preserving clear endoscopic access through the bougie, for example, to sites at the distal end of the bougie for inspection, manipulation, and/or suturing. In some embodiments, the restriction of intrusion is reversible during surgery, for example, upon withdrawal of a blocker device 102.

4. Fenestrations, in some embodiments, optionally function to admit tissue (for example, under suction) to a depth which is appropriate for the application of a permanent attachment means. In some embodiments, fenestrations are sized to admit enough tissue that a muscular layer 22 (FIG. 3B) of the stomach is accessible to penetration—for example by an endoscopically guided suture needle—but not so much tissue that penetration is likely to pass through the gastric wall entirely. It should be noted that a (healthy and normally distended) gastric wall typically comprises about 1.5-3 mm of mucosal and submucosal layers 24 overlying another 1-3 mm of the muscular layers 22 (or, for example 2-4 mm, or another thickness, depending on patient, stomach location, and/or degree of distension). Permanent suturing which passes into muscle specifically is preferable, to provide sufficient strength and durability of long-term attachment. Actually penetrating the gastric wall is preferably avoided, however, due, for example, to adverse effects caused by leaking stomach secretions.

5. Fenestrations, in some embodiments, optionally function as ports for the passage of needle and/or suture thread (and/or other attachment means and/or equipment involved in forming attachment) from the lumen of the bougie into the gastric wall. In some embodiments, suturing takes place entirely within the bougie lumen. However, in other embodiments, suturing involves passing a needle or other penetrating member and/or suturing equipment at least partially, or even entirely, outside the bougie, and/or within the thickness defined by its walls.

6. Fenestrations, in some embodiments, optionally function to temporarily stabilize gastric wall tissue by involvement in the suture itself. For example, in some embodiments, a suture thread is passed out of one fenestration, then back into another (optionally a plurality of times). This optionally temporarily ties the frame defining the fenestrations (the bougie) up with the gastric wall itself. In some embodiments, the bougie is configured so that the topology of the fenestrations can be changed to release them from this involvement, without cutting the suture thread. For example, a strip, guide, or insert is configured to be removable from the bougie. Additionally or alternatively, framework separating fenestrations comprises gaps (permanent and/or openable) through which suturing work can be passed by suitable manipulation. In some embodiments, temporary suturing to the bougie is used, optionally with penetration only to the mucosa, to stabilize and/or position the gastric wall to receive more stable primary suturing. Optionally, stabilization by bougie-sewn sutures is left in place to the end of a procedure. Optionally, stabilization is focused around a working region of the growing suture line, with sutured regions being allowed to come free from fixation as the working region moves away from them.

7. Fenestrations optionally function to temporarily stabilize gastric wall tissue by another means. In some embodiments, for example, fenestrations can change shape to help grip and/or clamp gastric wall tissue, potentially even in the absence and/or reduction of vacuum pressure. In some embodiments, a temporary securing device is applied to tissue intruding into the bougie through a fenestration, for example a pin and/or clamp. Optionally, the temporary securing device is itself sized and/or shaped so that it cannot pass the frame of the fenestration, thus securing the tissue in place. Optionally, fixation is applied either distal or proximal to a working region of the suture line (or both). Optionally, stabilization is iteratively added near the moving working region (region currently receiving suturing). Optionally, stabilization away from the working region is removed and/or relaxed before the end of the procedure.

Herein, bougie 100 is referred to in descriptions relating generally to a bougie comprising fenestrations according to some embodiments of the present invention. It should be understood that, insofar as particulars are applicable, such references also include other bougie embodiments comprising fenestrations for gastric wall suturing (including but not limited to bougies 300, 400, 500, and/or bougie embodiments including one or more of the detail variants also described herein).

Defining the Gastric Sleeve

Figure 1D:
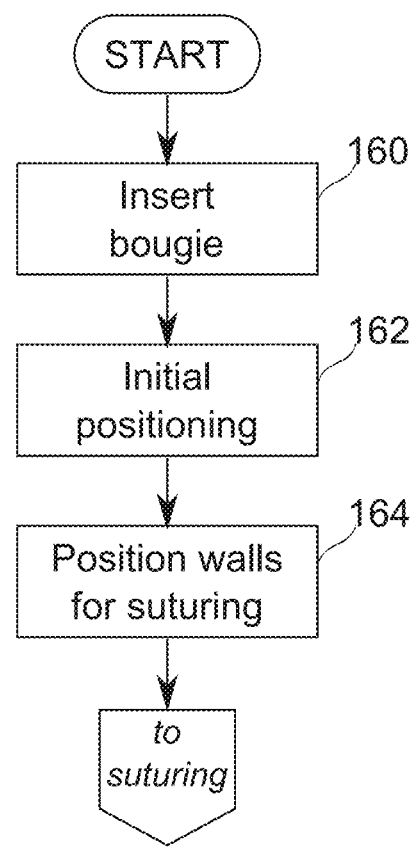
FIG. 1D is a schematic flowchart of a process of positioning a bougie in preparation for suturing, according to some exemplary embodiments of the invention.

Reference is now made to FIG. 1D, which is a schematic flowchart of a process of positioning a bougie in preparation for suturing, according to some exemplary embodiments of the invention.

At block 160, in some embodiments, a bougie, such as bougie 100 or another bougie, for example as described in relation to one or more figures herein, is inserted to the stomach 10 through the esophagus 14. In some embodiments, the bougie diameter is between 32-60 Fr (about 11-20 mm), or another diameter appropriate to esophageal insertion to the stomach.

At block 162, in some embodiments, the bougie 100 is brought into its initial position. For example, in some embodiments, balloon sections 104, 106 are placed where appropriate for balloon inflation, and/or the curve of bougie 100 is made and/or brought into alignment with the inner curve of the stomach 10, for example as shown in FIG. 1A.

Figure 1E:
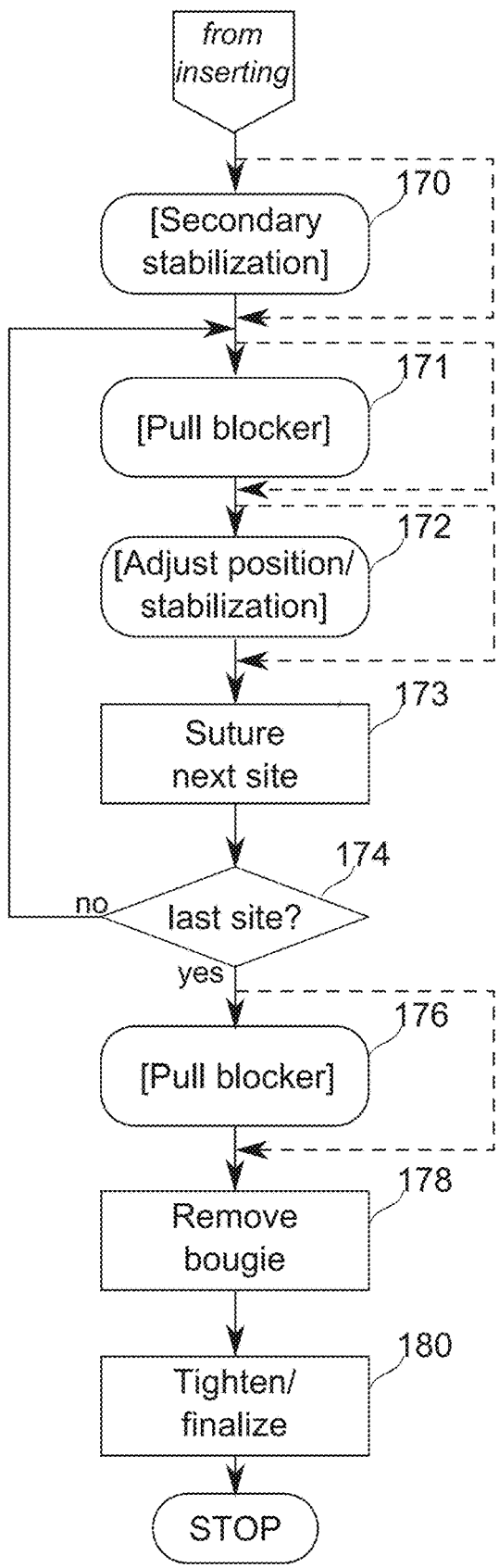
FIG. 1E is a schematic flowchart of a process of suturing gastric walls together using a bougie, according to some exemplary embodiments of the invention.
Figure 1F:
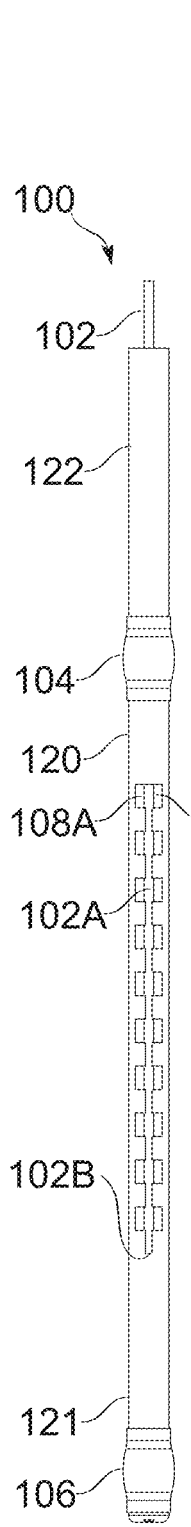
FIGS. 1F-1G schematically illustrate conversion of bougie gastric compartment sealing balloons from a deflated to an inflated state, according to some exemplary embodiments of the invention.
Figure 1G:
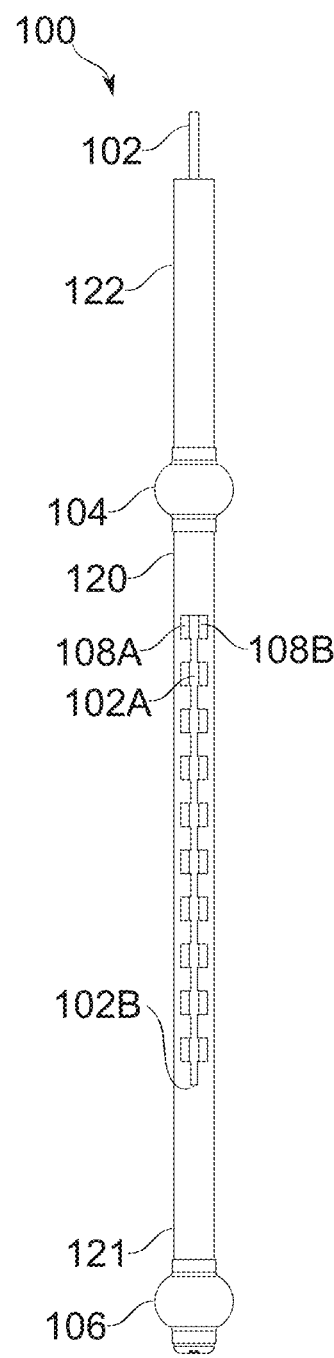
Figure 6A:
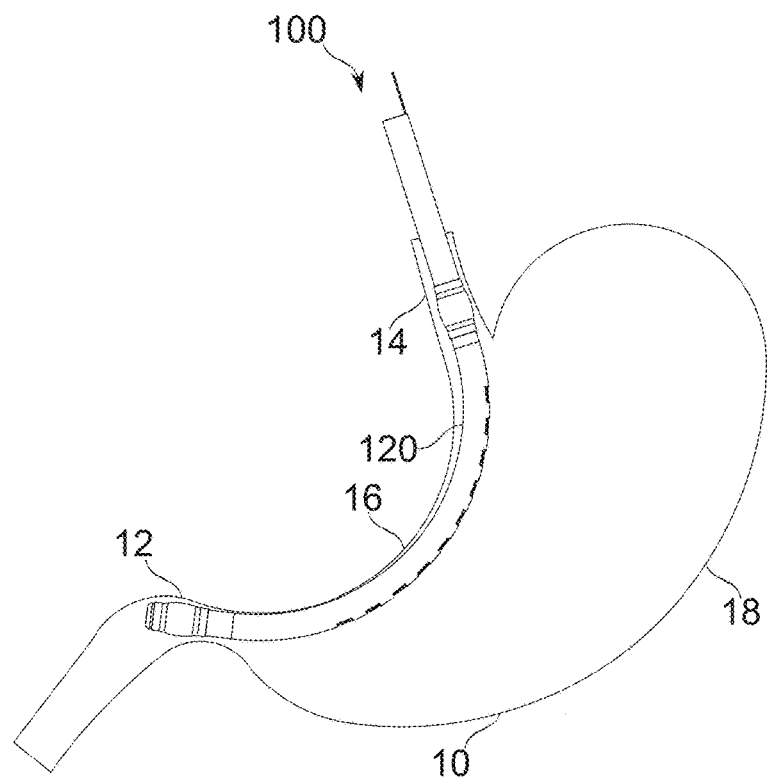
FIGS. 6A-6C schematically illustrate conversion of balloons from a deflated to an inflated state while in position within a stomach, according to some exemplary embodiments of the invention.
Figures 6B, 6C:
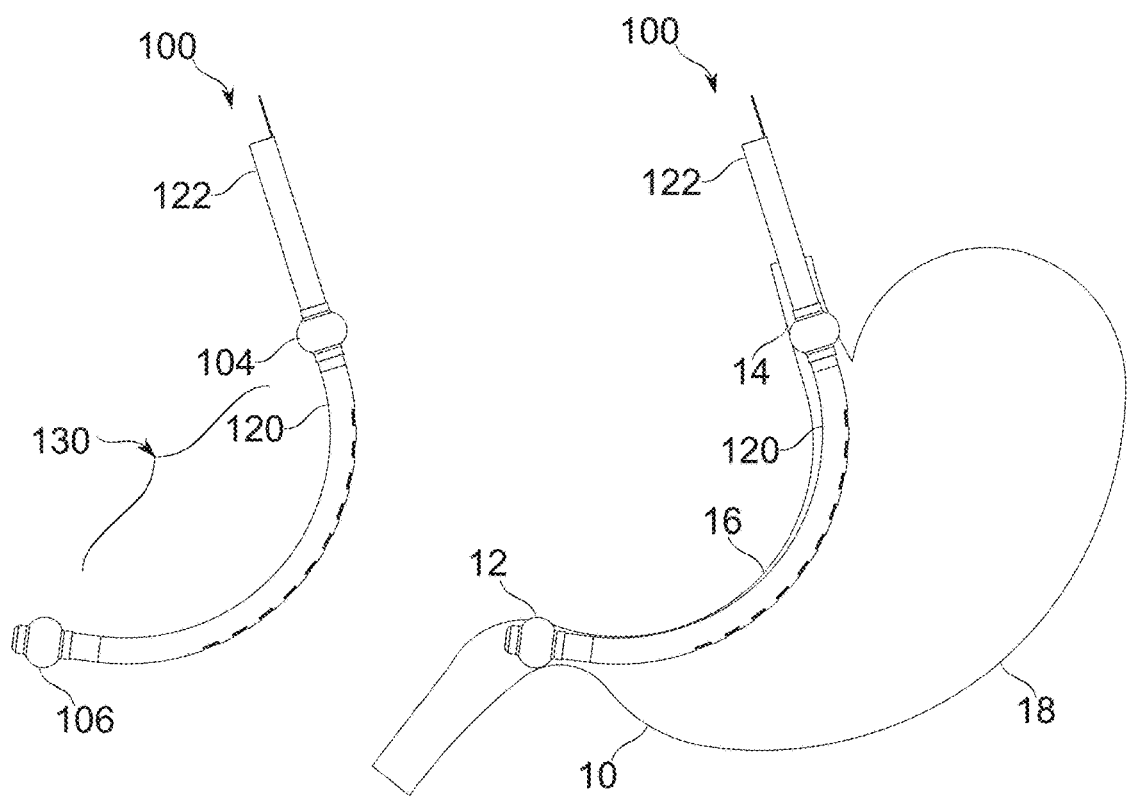

Reference is now made to FIGS. 1F-1G, which schematically illustrate conversion of balloons 104, 106 from a deflated to an inflated state, according to some exemplary embodiments of the invention. Reference is also made to FIGS. 6A-6C, which schematically illustrate conversion of balloons 104, 106 from a deflated to an inflated state, in position within a stomach, according to some exemplary embodiments of the invention.

In some embodiments of the invention, the distal end 121 of the bougie 100 is inserted into the stomach so that it reaches to the region of the pylorus 12. Optionally the bougie is anchored by inflation of a balloon 106. Optionally, the balloon 106 is situated in the pylorus 12, duodenum, and/or lower portion of the stomach 10 such that a seal resistant to vacuum is created when the balloon is inflated. Optionally, the bougie is anchored proximally by inflation of balloon 104. Optionally, the balloon 104 is situated in the esophagus 14, cardia, and/or upper portion of the stomach 10 such that a seal resistant to vacuum is created when the balloon is inflated. Resistance to vacuum is, for example, up to a vacuum gauge pressure of about 0.1 bar, 0.2 bar, 0.3 bar, 0.4 bar, 0.5 bar, 0.6 bar, or another greater, lesser or intermediate vacuum pressure.

A difference between FIGS. 1F and 1G (also shown straight and extended), and a difference also between corresponding FIGS. 6A and 6C (showing positioning of a curved bougie within a stomach 10) is the inflation of balloons 104, 106. In FIGS. 1F and 6A, balloons 104, 106 are deflated. The balloons 104, 106 are inflated in FIGS. 1G and 6B. FIGS. 6A and 6C also show the position of the bougie relative to features of the stomach 10 including the region whereat the gastric sleeve 16 is to be formed, and the outer curve of the stomach whereat a gastric pocket 18, to which the entrance of food will be largely restricted, is to be formed. The boundary between the two regions is according to the partition defined along approximation line 11 as illustrated in FIGS. 1A-1B. It should be understood that the gastric pocket configuration show in FIGS. 1A-1B is exemplary, and not limiting of the forms of gastric reduction to which embodiments of the current invention are applicable. For example, the final pattern, position, and/or length of gastric attachment is potentially different in different applications of some embodiments of the invention, according to the specifics of the procedure.

Some potential advantages of endoluminal gastroplasty as such are described hereinabove, and include, for example, reduced risk of leakage, lowered invasiveness of the procedure, and/or reduced recovery time. Potentially, the risk of interruptions to the blood supply of remaining functional parts of the stomach/pylorus is reduced by avoiding wholesale resection. Optionally or alternatively, electrical blockages and/or arrhythmias are avoided.

Nevertheless, as an exemplar of the range of possible procedures contemplated: an initial gastroplastic formation of a gastric sleeve serves as a first phase of a series of procedures leading to gastrectomy. Initial gastroplasty is performed all the way between esophagus and the pylorus, and follow up of the patency of the result performed, for example, by measuring the transfer of a trace material from the sleeve to the isolated pocket. Upon determination, for example, that a good seal has been formed, gastrectomy is performed to remove the pocket region, making the procedure permanent.

In some embodiments an opening to the pocket (e.g., near the pylorus) serves to allow gastric flow out of the pocket and/or avoid interruption of blood flow, electricity and/or peristaltic waves.

FIG. 6B shows the bougie 100 in bent form without the stomach 10, where curve 130 conforms to the curve of the stomach near inner curve 16. In some embodiments, the bougie 100 is naturally straight (when unconstrained), and bends to conform to the curve upon insertion. In some embodiments, bougie 100 is naturally curved (when unconstrained), but can be straightened sufficiently to pass through the esophagus 14 and into the stomach 10. Within the stomach, a pre-curved bougie 100 tends to re-assume its curved shape, potentially assisting positioning.

At block 164, in some embodiments, the bougie and/or the gastric walls are manipulated so as to bring the walls into approximation, such that a seam line forms along or about along the rows of fenestrations 108A, 108B on body 120 of bougie 100.

Optionally, manipulation comprises application of vacuum (for example, to a level of about 0.5 bar gauge, or a greater or lesser vacuum). Optionally, collapse upon application of vacuum is uniform and symmetric around the bougie, such that the two walls naturally collapsed to meet in the region of the fenestration rows. Optionally, a first wall is captured, and then a second wall. Optionally vacuum is turned on and off during capture, as the walls are coaxed into position (one at a time, simultaneously, or alternately), before a desired configuration is reached.

In some embodiments of the invention, vacuum ports are positioned to help guide a process of approximation around the bougie. Bougie 2100 of FIG. 21A, for example, provides an example of vacuum ports distributed around the circumference of a bougie, which potentially act to draw gastric wall continuously around the bougie from one side to where the two wall parts meet on the other. In some embodiments of bougie 100, such circumferentially distributed vacuum ports are provided.

In some embodiments, the material of at least a portion of bougie 100 is transparent. Optionally, this allows visualization through the bougie body 120 of the surrounding state of the gastric wall 20. Potentially, this helps guide positioning.

Upon completion of insertion (in the above-described, or another order of subtasks), one or more of the following has been accomplished:

The walls of a future gastric sleeve are defined by the wall portions which wrap around the bougie.

The seam along which opposite sleeve walls are to be attached is defined, and placed about along the line defined by the rows of fenestrations 108A, 108B.

Optionally, the gastric compartment is sealed against the entry of gas, allowing a stable vacuum to be provided.

Furthermore, in some embodiments, gastric wall tissue is pulled and held to fenestrations 108A, 108B of the bougie 100 by vacuum, but prevented at most or all of the fenestrations from deeply intruding into the lumen 40 of bougie 100 by a blocker 102.

Figure 2A:
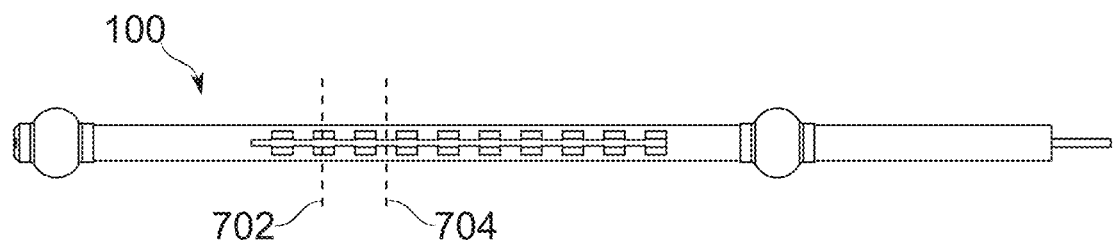
FIGS. 2A-2C schematically illustrate the position of gastric wall tissue around cross sections of a positioned bougie under vacuum, the wall tissue being prevented from free entry to the lumen of the bougie by a blocker, according to some exemplary embodiments of the invention.
Figure 2B:
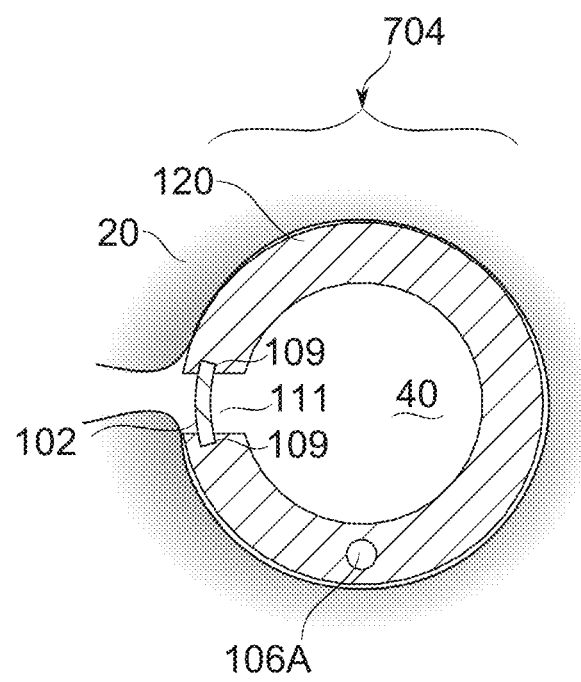
Figure 2C:
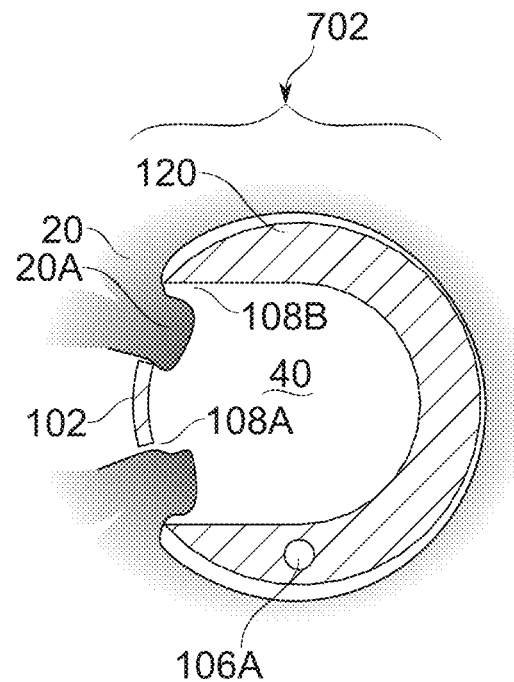

Reference is now made to FIGS. 2A-2C, which schematically illustrate the position of gastric wall tissue around cross sections of a positioned bougie 100 under vacuum, the wall tissue being prevented from free entry to the lumen 40 of the bougie by a blocker 102, according to some exemplary embodiments of the invention.

In some embodiments, blocker 102 comprises a strip extending along the fenestrated length of bougie 100. Optionally, the strip divides two rows of fenestrations; defining for each a medial limit. The strip is braced along the length of the bougie, for example by slots 109 and/or cavities through which a portion of the strip passes.

FIG. 2A shows the bougie 100 in a straight and extended configuration for clarity of illustration. FIGS. 2B and 2C show cross-sections 704 and 702, respectively. Cross-section 704 is at a level of bougie body 120 where there is no open fenestration. Blocker 102 entirely covers any gap in region 111 which might otherwise exist in the bougie 100 at this level. Accordingly, gastric wall 20 is not forced into close approximation here.

Cross-section 704 is at a level of bougie body 120 where open fenestrations 108A and 108B are found. The two fenestrations are prevented from directly merging at this level by the inter-spaced position of blocker 102. Due, for example, to vacuum, gastric wall 20 comprises intrusions 20A through the fenestrations, but the depth of the protrusion is shallow enough that lumen 40 remains substantially open.

In FIG. 2B, blocker 102 is shown as bridging a gap in the wall of the bougie body 120. In some embodiments, the wall of the bougie body continuously crosses a region between fenestrations in the same row, and the blocker 102 passes within or through the wall in these regions.

In some embodiments, the same blocker 102 or another blocking structure comprises regions which run along the lateral boundaries of the fenestration rows, limiting fenestration width. Optionally, a blocker portion comprises portions that reduce fenestration size as measured along the length of the bougie 100. In an example including blocking arrangements for restricting the size of each side of the fenestrations, a sliding blocker comprises three long vertical strips, cross-linked by horizontal strips at intervals corresponding to the period of the fenestrations.

A second lumen 106A contained within the sidewall of bougie body 120 is also shown in FIGS. 2B and 2C. In some embodiments, this comprises an inflation fluid conduit leading to balloon 106.

Figure 5:
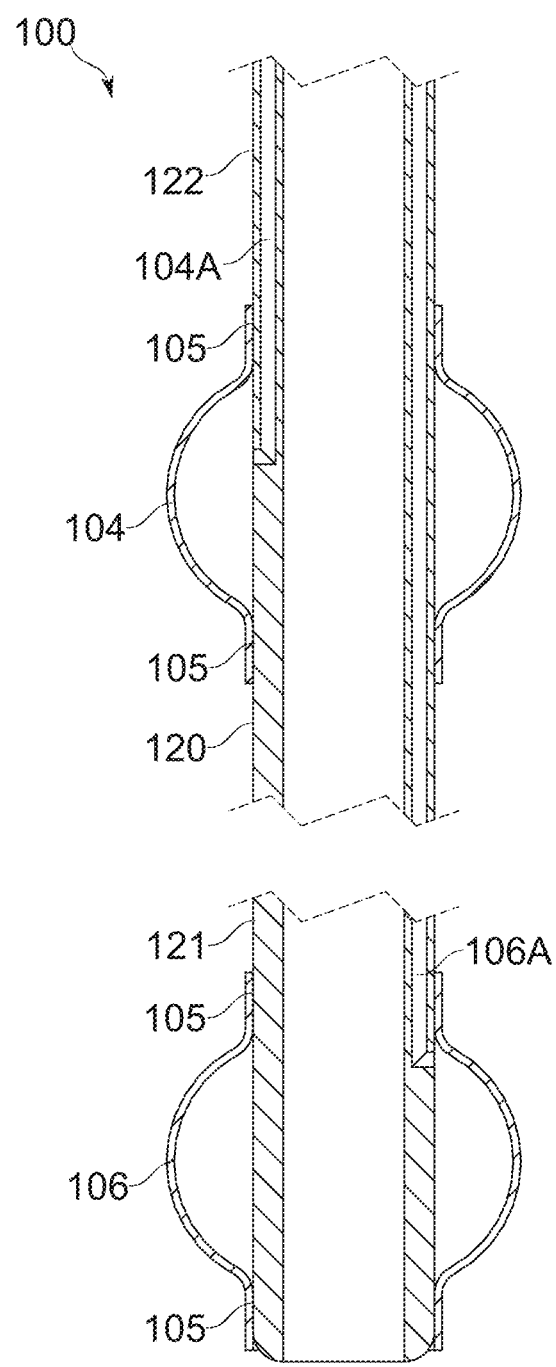
FIG. 5 schematically illustrates the configuration of inflatable bougie anchoring balloons, according to some exemplary embodiments of the invention.

Reference is now made to FIG. 5, which schematically illustrates the configuration of inflatable bougie anchoring balloons 104, 106 and their inflation lumens 104A, 106A, according to some exemplary embodiments of the invention.

In some embodiments, the inflation states of balloons 104, 106 are managed by the movement of an inflation fluid (gas such as air or $CO_2$; or liquid such as saline) through their respective inflation fluid conduits 104A, 106A. Optionally, a single conduit serves both balloons. In some embodiments, balloons 104, 106 comprise flexible (optionally, elastic) membranes attached to the body 120 of a bougie 100, for example, around rings 105.

Suturing the Gastric Sleeve

Reference is now made to FIG. 1E, which is a schematic flowchart of a process of suturing gastric walls together using a bougie 100, according to some exemplary embodiments of the invention.

It is envisioned that several variations of the suturing procedure are enabled by embodiments of the present invention. In some cases, multiple variations can be carried out by various use of a single embodiment. Optionally, variation is within a single procedure. In some cases, variations are carried out by different embodiments of the invention. Variably carried-out operations are indicated in FIG. 1E by the use of dotted-line bypasses, and round-cornered blocks, where appropriate. Also where appropriate, it should be understood that other orders of operations, reversals, and repetitions are to be carried out as necessary during an actual surgical procedure.

In some embodiments, suturing is with surgical suture thread and needle, performed under endoscopic guidance. Optionally, the suture used is a barbed or "knotless" suture. In some embodiments, suturing is performed with the use of an automatic or semi-automatic suturing device.

After insertion and positioning of bougie 100, at block 170, in some embodiments, secondary stabilization optionally occurs. In some embodiments, (particularly for example, if it is found to be difficult to sealingly secure one or both of balloons 104, 106, due, for example, to irregularities of the patient anatomy), vacuum stabilization is immediately supplemented with another stabilizing method. Optionally, for example, barbed suture is passed between the two gastric wall sections at one or more places along the body 120 of the bougie 100, regardless of whether or not the more stable muscle layers are surgically accessible at this stage.

Figures 4A, 4B:
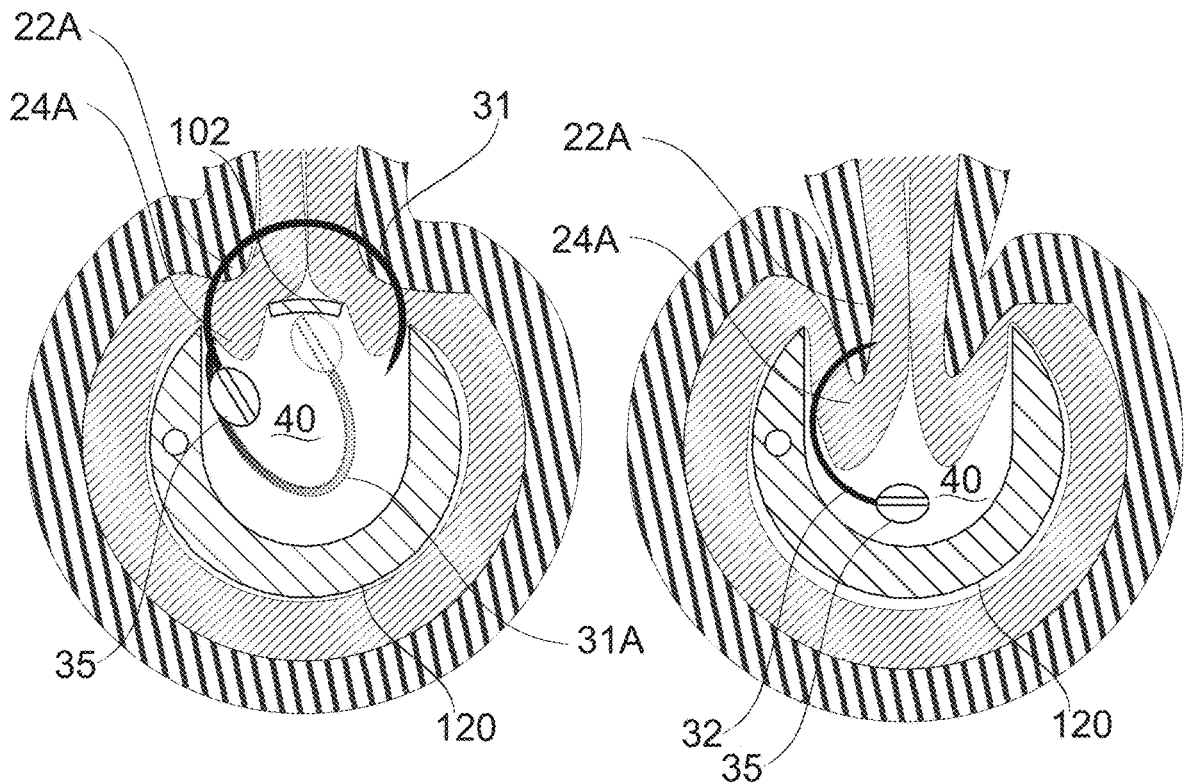
FIGS. 4A-4B schematically illustrate alternative suturing situations, according to some exemplary embodiments of the invention.
Figure 4C:
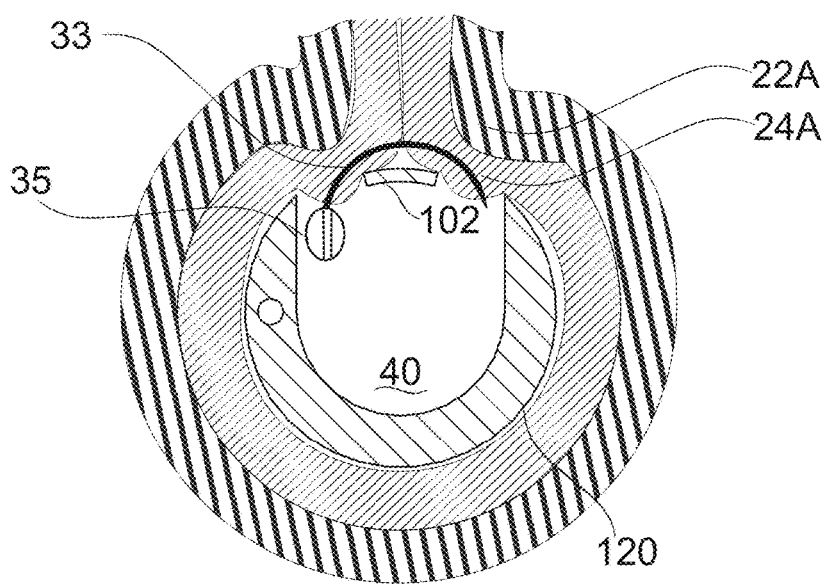
FIG. 4C schematically illustrates penetration by a needle under the control of a needle holder into superficial regions of gastric wall tissue, according to some exemplary embodiments of the invention.

Reference is now made to FIG. 4C, which schematically illustrates penetration by a needle 33 under the control of a needle holder 35 into superficial regions 24A of gastric wall tissue, according to some exemplary embodiments of the invention. In some embodiments, motions of the needle and/or needle holder are monitored under visualization, for example, endoscopically or radiographically monitored. Optionally, the bougie is provided with one or more radioopaque markers, for example, near fenestrations thereof, at its ends and/or in the sealing balloons (if any).

In some embodiments, this relatively insecure form of suturing is used to provide (optionally temporary) stability against fluctuations in vacuum, either accidental, or during position adjustment. Potentially, such sutures are relative fast and easy to perform; since, for example: there is relatively free maneuvering room (less tissue filling) within the lumen 40 bougie body 120, the tissue 24A to be penetrated is relatively less tough than the more muscular deep layers 22A, and/or because the depth of penetration required is relatively low. Optionally, only a portion of the suture points which will be finally secured are attached with stabilizing sutures. It should be noted that the stabilization comes from suturing blocker 102 to the tissue. The ability to later slide the blocker out of position prevents this from becoming a permanent situation.

Alternatively or additionally, secondary stabilization comprises one or more pins driven horizontally or vertically through short tissue intrusions into the bougie lumen. For example, a pin is driven vertically down one or both rows of tissue intrusions. Additionally or alternatively, tissue intrusions are stabilized by horizontally arranged piercing needles. For the speed of the procedure, it is a potential advantage to operate such piercing needles as a unit. For example, a row of arc-shaped needles is optionally mounted on a common driving mechanism (such as a shaft or partial tube), allowing them to be driven around the inner circumference of the bougie to skewer tissue intrusions from the side. Optionally, secondary stabilizations are individually controllable, and in particular, individually removable as needed; for example: by removal of a vertical pin one intrusion at a time, or, for example, by removal of horizontal piercing needles one needle at a time. Other examples of secondary stabilization means include helical inserts (corkscrews that screw into the gastric wall) and/or clamps.

Secondary stabilization means of whatever type are optionally applied, for example, in the case where it is found necessary to reduce vacuum and/or readjust the wall positions in another portion of the bougie. In general, however, it has been observed by the inventors that good initial positioning of the stomach walls within the fenestration rows of the bougie under vacuum can be readily achieved, and that the stabilization of vacuum provided by the balloons allows suturing to be completed without a need for readjustment or reliance on secondary stabilization.

At block 171, in some embodiments, blocker 102 is (optionally) partially pulled in a proximal direction from its previous blocking position. Optionally, blocker 102 is pulled far enough to merge one pair of fenestrations 108A, 108B into a single merged fenestration 110. Optionally, movement of blocker 102 otherwise opens the fenestrations for the admission of additional gastric wall tissue. For example, moving the blocker removes constraints on the fenestration size from the lateral sides, top, and/or bottom of the fenestrations. Additionally or alternatively, the blocker masks a thinner medial portion (part of the bougie wall, or another moveable blocker); such that the fenestrations 108A, 108B remain separate, while admitting additional tissue (for example, under the force of vacuum pressure).

Figure 1H:
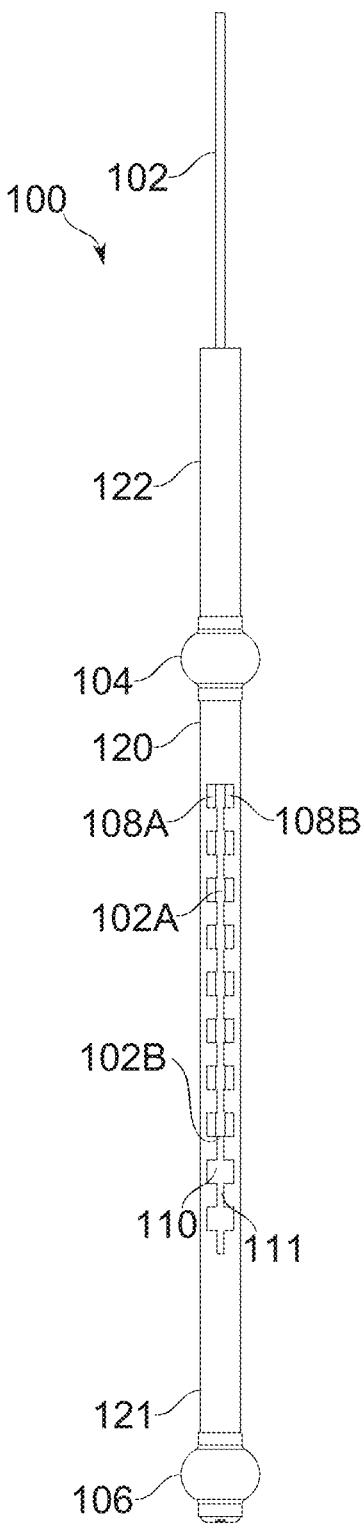
FIGS. 1H-1I schematically illustrate bougie with blocker partially withdrawn to merge a portion of its paired fenestration rows, according to some exemplary embodiments of the invention.
Figure 1I:
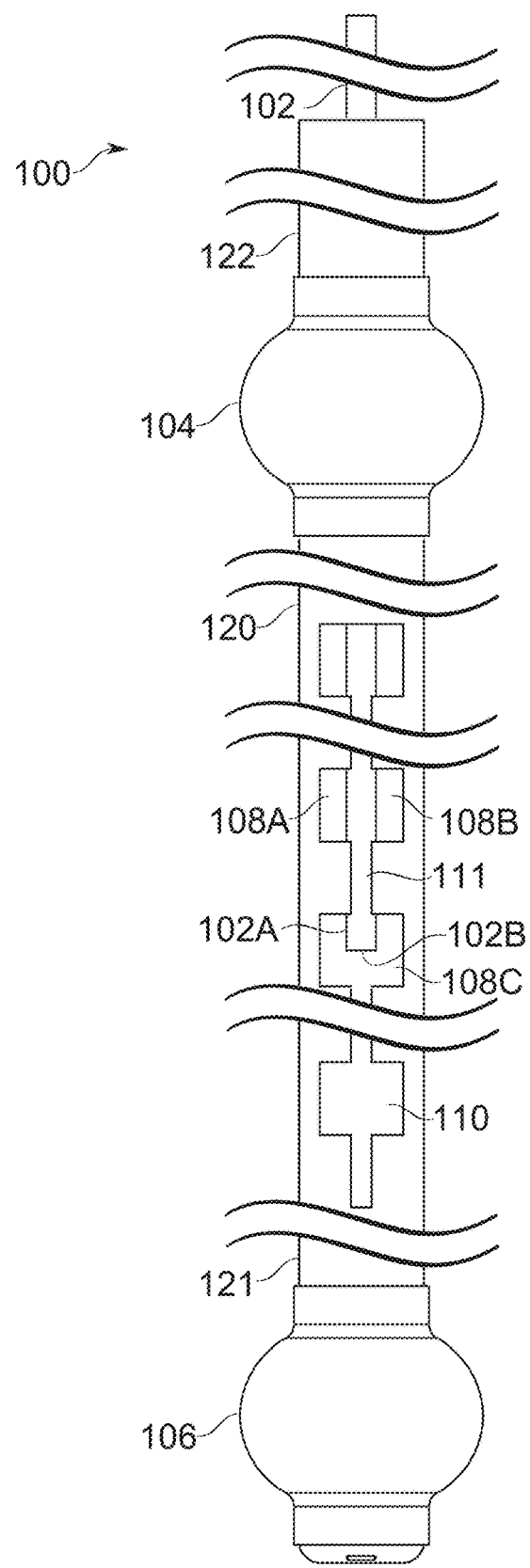

Reference is now made to FIGS. 1H-1I, which schematically illustrate bougie 100 with blocker 102 partially withdrawn to merge a portion of its paired fenestration rows, according to some exemplary embodiments of the invention. FIG. 1I shows magnified versions of several of the same details as FIG. 1H, with intervening sections elided. Also, FIG. 1I shows the terminal end 102B of blocker 102 in a different position relative to a partially unblocked fenestration 108C than is shown in FIG. 1H.

In some embodiments, blocking portion 102A of blocker 102 separates rows of fenestrations 108A, 108B until it is at least partially withdrawn proximally via the proximal end 122 of the bougie 100. Distal blocker end 102B of blocker 102 marks the most distal point which remains fully separated. In some embodiments, withdrawal of blocker 102 merges the fenestration rows, one pair at a time, to form merged fenestrations 110. In some embodiments, withdrawal also exposes a region 111 which comprises a gap connecting fenestrations adjacent along the length of the bougie body 120. Alternatively, region 111 comprises a bridging portion across bougie body 120, which blocker 102 crosses, but does not open when it is withdrawn.

In some embodiments, the widths (around the circumference), heights (along the length), and intervals of and/or between (unblocked) fenestrations are about 1 cm. Such distances provide about a 2 cm suturing pitch, which provides a reasonable balance between preventing substantial leakage across the gastric sleeve to the semi-isolated gastric pocket, and avoiding a need for making an excessive number of suturing passes through the tissue, extending the length and/or difficulty of the procedure. In some cases a different stitch pitch is provided, for example, between 0.8 and 2 cm, for example, about 1 cm or 1.2 cm.

In an exemplary embodiment of the invention, each fenestration receives a single pitch. In some embodiments, two or more stitches may be provided for at least some fenestrations. In some embodiments, the stitches are tight, for example, to prevent leakage and/or encourage tissue adhesion. Optionally, a tissue adhesion material is provided between the stomach walls, for example, by elution or injection via blocker 102. Optionally or alternatively, an adhesive encouraging element, such as a mesh is implanted between the stomach walls, for example, being originally mounted on blocker 102 and more tightly held by the sutures than blocker 102, so it can separate therefrom.

In an exemplary embodiment of the invention, if there is no penetration of stomach outer layer, some leakage into the pocket, for example, of between 10% and 40% (or more) of the food entering the sleeve may be tolerated. In other embodiments, it is desired that at least between eth stitches leakage is less than, for example, 10%, 5% or 1% and the stitches are pitched closely enough together and/or tightly enough.

Blocked, the fenestration widths are reduced, for example, to about 3 mm, with the blocker 102 being about 3 mm wide. These can be related to typical gastric wall thicknesses (single thickness) of 2-5 mm. In some healthy patients, gastric wall thicknesses up to about 7 mm are reported. Still thicker gastric wall thicknesses can occur, for example, in a stomach having neoplasia, and/or a stomach where full distension has not been achieved. In some embodiments, portions of up to 4 wall thicknesses (two walls, each partially doubled over) are drawn to the bougie for their mutual attachment. It should also be understood that other dimensions compatible with the surgical conditions of tube insertion to the stomach through the esophagus are possible, including dimensions which are different for each of these measurements, and/or among different fenestrations. Dimensions of fenestrations of various embodiments are also described, for example, in relation to FIGS. 10A-10H hereinbelow.

Figure 3A:
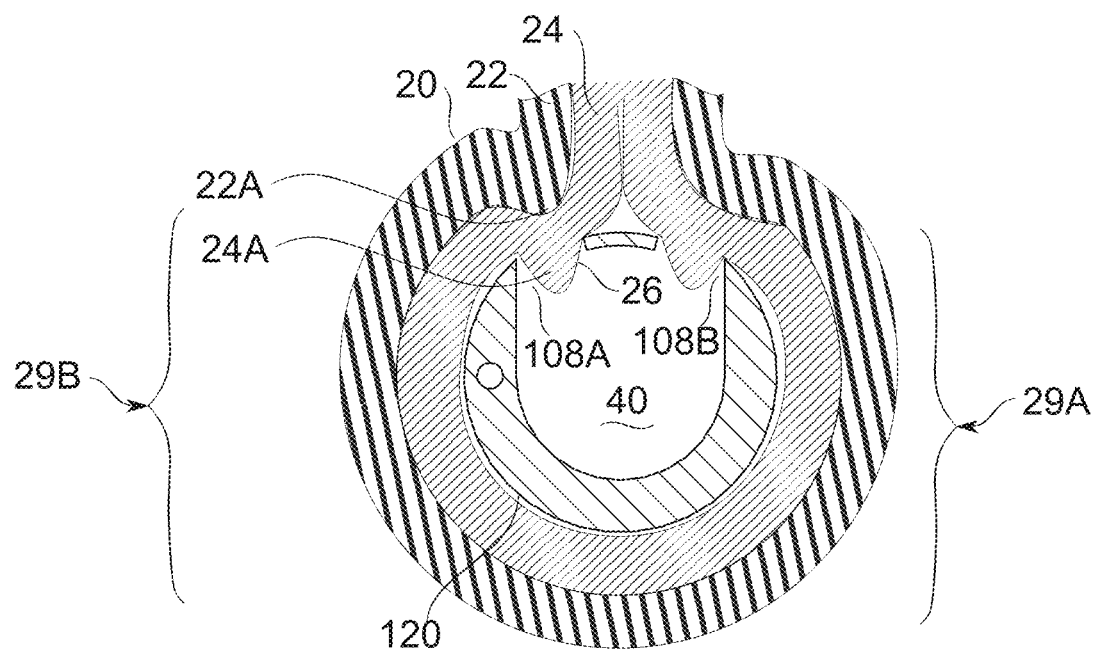
FIG. 3A schematically illustrates the invagination of gastric wall tissue to a bougie upon application of vacuum, according to some exemplary embodiments of the invention.
Figure 3B:
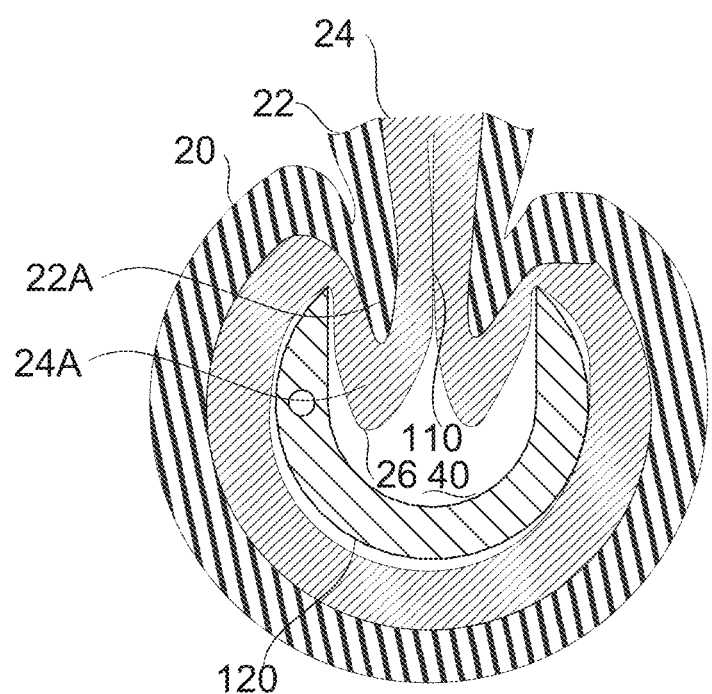
FIG. 3B schematically illustrates the further invagination of gastric wall tissue into a bougie upon removal of strip while vacuum continues to be applied, according to some exemplary embodiments of the invention.

Reference is now made to FIG. 3A, which schematically illustrates the vacuum invagination of gastric wall tissue to a bougie 100 with intrusion-limiting fenestrations, according to some exemplary embodiments of the invention. Reference is also made to FIG. 3B, which schematically illustrates the further invagination of gastric wall tissue 20 into a bougie 100 upon removal of blocker 102 while vacuum continues to be applied, according to some exemplary embodiments of the invention. Considered sequentially, FIGS. 3A-3B illustrate the effects on tissue position within a cross-section of bougie lumen 40 upon the withdrawal of blocker 102 from a pair of fenestrations 108A, 108B.

In FIG. 3A, the two opposing portions 29A, 29B of gastric wall 20 are shown drawn around the body 120 of a bougie 100, for example as they are positioned after proper positioning of the bougie for beginning suturing. With vacuum applied to the bougie, portions 26 of the more superficial gastric wall layers 24 are drawn into bougie lumen 40. The superficial layer 24 includes, for example, portions of the mucosa and/or submucosa. Because the fenestrations 108A, 108B are relatively narrow in at least one dimension, the amount of tissue drawn is relatively small, and lumen 40 remains relatively open.

However, upon withdrawal of blocker 102, a wider merged fenestration 110 is formed (FIG. 3B). Portions 26 are then able to invaginate more fully into the lumen 40 of the bougie body 120. This results in the deeper layers 22 of the gastric wall 20 becoming more accessible from the side of the lumen. Optionally, the deeper layers comprise, for example, the muscular layers of the gastric wall. The muscular layers are, in some embodiments, a preferred target for suturing due to greater toughness in supporting sutures. It can be understood that another change which widens fenestrations 108A, 108B would also allow the admission of additional tissue for suturing. For example, in some embodiments, widening of the fenestrations comprises removal of a laterally situated blocker and/or blocking which is above and/or below the plane of the FIG. 3B. Likewise, merging of fenestrations 108A, 108B to a single fenestration 110 is a feature of some but not all embodiments of the invention. Merging fenestrations confers the potential advantage of allowing opposite walls to be sutured together without suturing the frame of the bougie itself into place. Another potential advantage is simply that the blocker 102 is removed from a position where it could interfere with the act of suturing.

Nevertheless, it is possible, in some embodiments, to leave blocker 102 in place at this stage of the suturing, and remove it (freeing the bougie) at a later stage, for example as described in relation to block 176.

At block 172, in some embodiments, the position and/or stabilization of the bougie is optionally adjusted. In some embodiments, the gastric walls are fully positioned before suturing begins (for example, at block 164), and vacuum is maintained fully throughout the suturing procedure. Potentially, this configuration is sufficiently stable that no additional position adjustment is required. In some embodiments, initial configuration comprises grabbing and positioning only a portion of the eventual line of approximation, so that movement of blocker 102 changes the tissue which is available to be secured. In some embodiments, a region of wall newly exposed to vacuum is adjusted into place, for example by iterative raising and lowering of vacuum, coaxing motions (wigging) of the bougie, or another method.

At block 173, in some embodiments, suturing of the next site of tissue intrusion along the bougie 100 is performed.

Reference is now made to FIGS. 4A-4B, which schematically illustrate alternative suturing situations, according to some exemplary embodiments of the invention. Reference is also made to FIGS. 4D-4E, which schematically illustrate cutaway side-views of suturing from within bougie 100, according to some exemplary embodiments of the invention. Further reference is made to FIGS. 4F-4G, which schematically illustrate the potential for interference of proximal tissue intrusions on the suturing of more distal tissue intrusions within bougie 100, according to some exemplary embodiments of the invention. Reference also is made to FIG. 4H, which schematically illustrates suturing at a level of the bougie with a blocker in place, according to some exemplary embodiments of the invention.

In some embodiments of the invention, it is a potential advantage to suture sites beginning from the distal portion of the bougie and working more proximally from site to site. Proximally-directed removal of blocker 102 causes distal sites to deeply invaginate first, while more proximal sites continue to be restrained from intrusion to the lumen 40. If all sites were deeply invaginated to the lumen 40 from the beginning of the procedure, it would be potentially more difficult to reach the distal end of the bougie. In FIG. 4B, in some embodiments, a situation of suturing to a site of a removed blocker is schematically illustrated. The needle holder 35 is shown passing a needle 32 into the deep (muscular) layers 22A of the gastric wall, in a portion of lumen 40 which is largely filled by involuting tissue. An advantage of suturing in this configuration is the relatively high exposure of the muscular layer 22A. Potentially, the disadvantage of restricted space at the cross-section of the fenestration itself is overcome by suturing from an out of plane angle.

In some embodiments, however, blocker 102 is left substantially in place during suturing. Optionally, it removed instead after suturing, for example, at the end of the procedure. FIG. 4A illustrates suturing for this alternative form of the procedure. In this case, the exposure of the muscular tissue is potentially lower. As illustrated, the needle needs to pass substantially outside lumen 40 in order to reach the targeted muscle layer 22A. Potentially, this requires using a somewhat larger radius and/or longer needle 31, which potentially creates a different form of spatial restriction on the range of motions available for suturing. Needle 31 is also shown at an out-of-plane position 31A, which can potentially overcome such a spatial restriction.

FIG. 4H illustrates another suturing situation which blocker 102 remains in place until after placement of the suture, and suturing occurs within lumen 40 of a bougie body 120. In some embodiments, blocker 102 and fenestrations 108A, 108B are sized such that a portion of target tissue layer 22A is admitted to lumen 40 upon application of suction. In some embodiments, this allows needle holder 35 to pass needle 32 through the target layer, effectively sewing-in the bougie body 120 until bougie blocker 102 is removed, for example by sliding proximally along the longitudinal axis of the bougie until the suture region is freed.

In some embodiments, another form of blocker which allows post-suture freeing comprises a blocker having a longitudinal body, located alongside the fenestrations, and along which "L" shaped projections are attached at intervals corresponding, for example, to the fenestration period. The horizontal bars of the "L" shapes of the blocker project between fenestrations, while the rising bars of the "L" shapes project longitudinally between the fenestrations (in either longitudinal direction; or if in both, the shape is a sideways "T"). A sufficient gap is optionally left between each projection to allow release of a suture and/or of sutured tissue as the gap passes across it. Release, in such embodiments, comprises moving the blocker proximally or distally (depending on the orientation of the "L") for a sufficient fraction of the inter-fenestration space that release occurs. This potentially allows simultaneous release of sutured-in fenestrations. Potentially, this allows simultaneous adjustment of the penetration depth of the tissue along the length of the bougie, since, as the gap crosses over the fenestration region, the deepest penetration achieved by the tissue along the fenestration is liable to increase.

In some embodiments of the invention, the L- or T-projection blocker is rotatable around the axis of the bougie. Optionally, this motion is used during capture of the gastric walls. Optionally, the blocker is first rotated to move the vertically projecting bars into place over one of the sets of fenestrations, ensuring that all tissue captured during an approach to one of the walls falls onto a single side of the fenestration rows. Upon sufficient capture of the first wall, the bars are rotated toward the middle to push the captured wall out of the way, and the second wall sought and captured.

FIGS. 4D-4E show views from orthogonal angles of a needle 34 being inserted through intruding gastric wall tissue layers 24A, 22A.

In some embodiments of the invention, suturing is by means of an automated or semi-automated stitching device, for example, a device mounted at the end of an endoscope. Such a device and/or the endoscope tip on which it is mounted typically occupies a 1 cm diameter cylinder or larger. Potentially, this largely fills the bougie lumen 40, leaving little space for maneuvering. In some suturing devices, moreover, there is a distally protruding part, and a more proximal part, between which tissue to be sutured must be positioned. In such embodiments, it is a potential advantage to move the suturing device into position before withdrawing the blocker, allowing tissue to infill between the distally protruding part and the more proximal part, so that suturing can occur. FIG. 10C illustrates an embodiment potentially useful in such a situation, where fenestrations 1002A, 1002B of the two rows (corresponding to the two walls) are alternately arranged (mutually offset by a distance 1009) along the bougie length. Thus offset, they can be alternately opened as a blocker 102 is withdrawn, allowing the suturing device to be moved into position for one tissue protrusion at a time, and for each such protrusion.

Figure 4F:
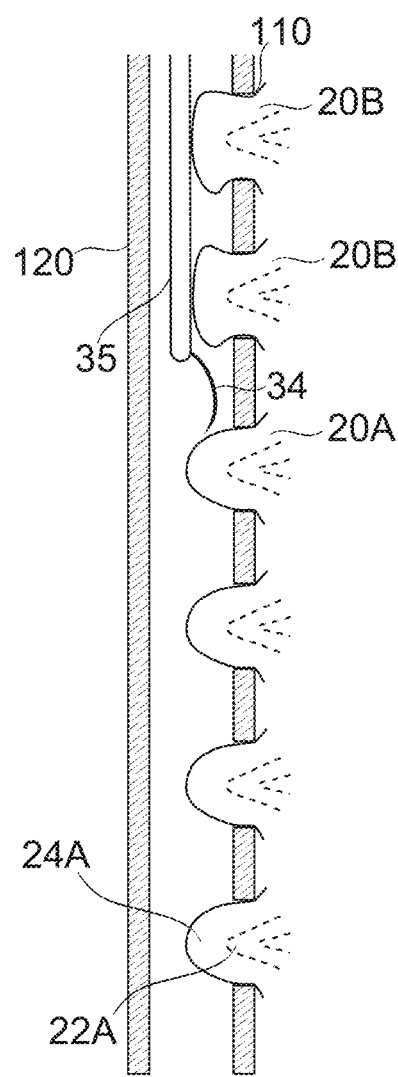
FIGS. 4F-4G schematically illustrate the potential for interference of proximal tissue intrusions on the suturing of more distal tissue intrusions within a bougie, according to some exemplary embodiments of the invention.
Figure 4G:
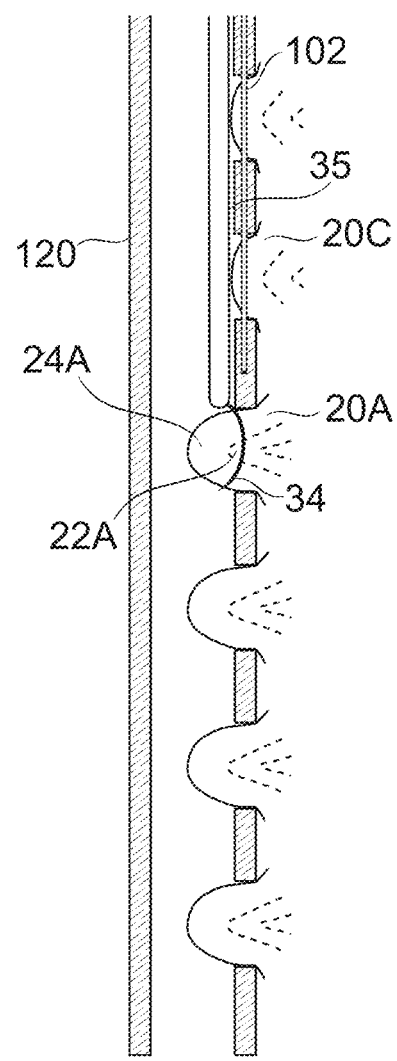
Figure 4H:
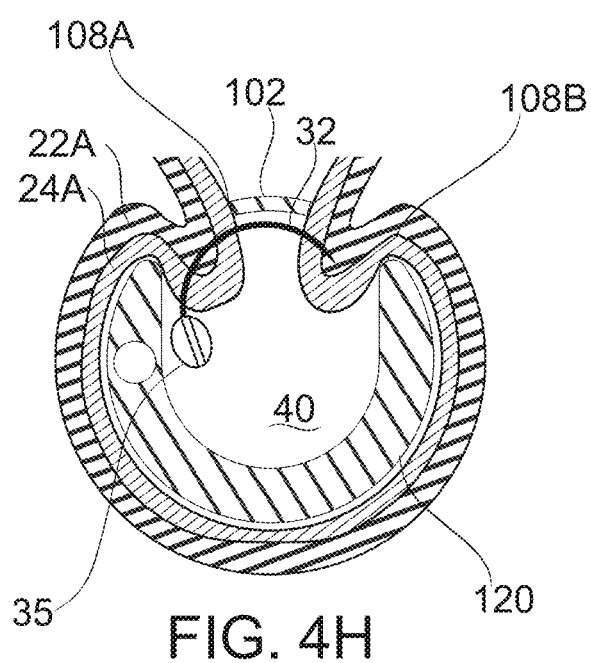
FIG. 4H schematically illustrates suturing at a level of the bougie with a blocker in place, according to some exemplary embodiments of the invention.

In FIGS. 4F-4G, a relatively thin needle holder 35 is shown attempting to insert a needle 34 into a tissue protrusion comprising tissue layers 22A, 24A.

More distal protrusions 20B of FIG. 4F fill lumen 40 sufficiently to interfere visualization and/or positioning of needle 34 and/or needle holder 35. More distal protrusions 20C of FIG. 4G, however, remain restrained by a blocker 102, permitting more freedom of visualization and/or positioning of needle 34 and/or needle holder 35.

Figure 12A:
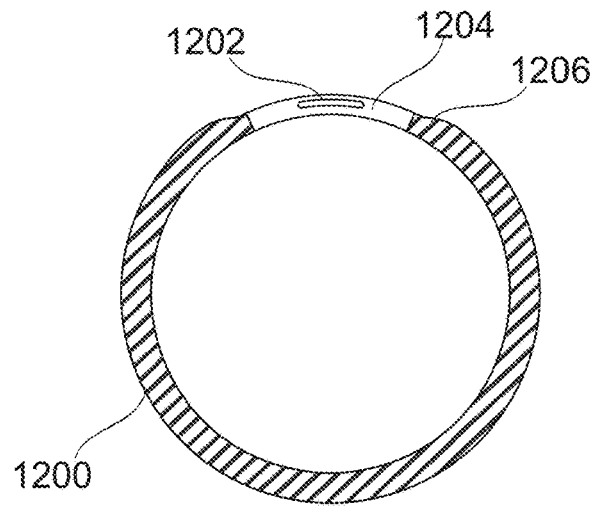
FIGS. 12A-12D schematically illustrate different shapes of bougie bodies, according to some exemplary embodiments of the invention.
Figure 12B:
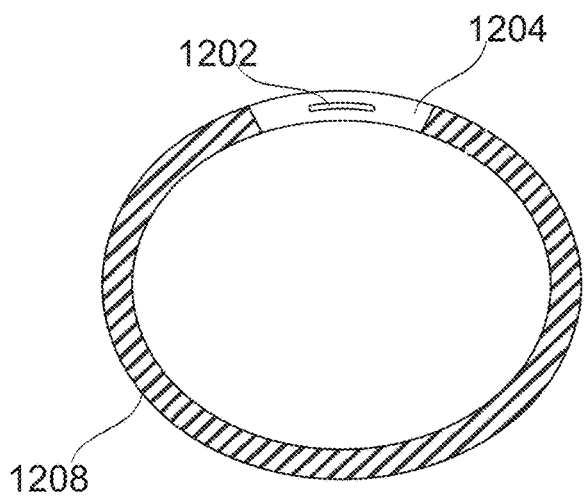
Figure 12C:
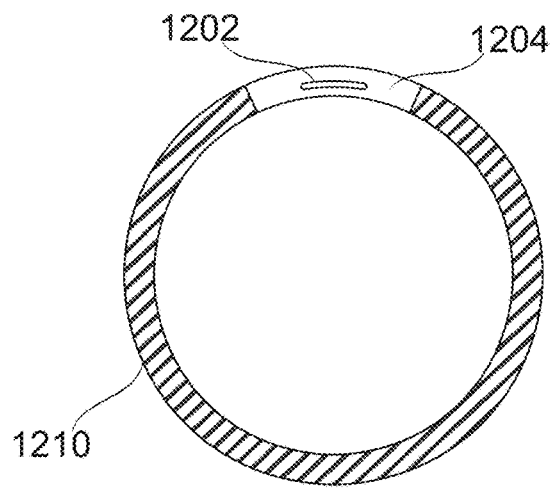
Figure 12D:
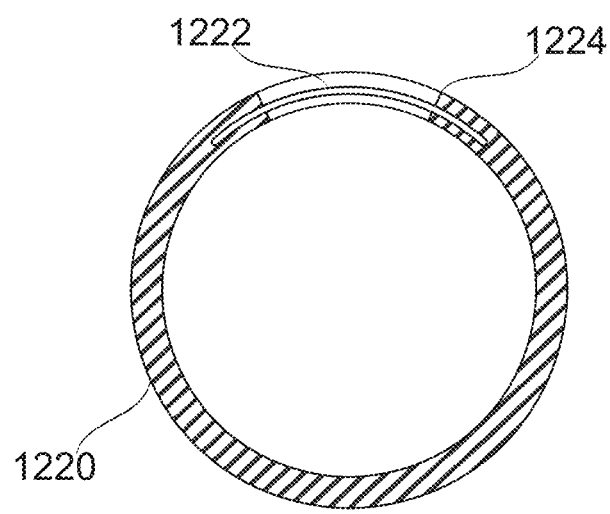
Figure 12E:
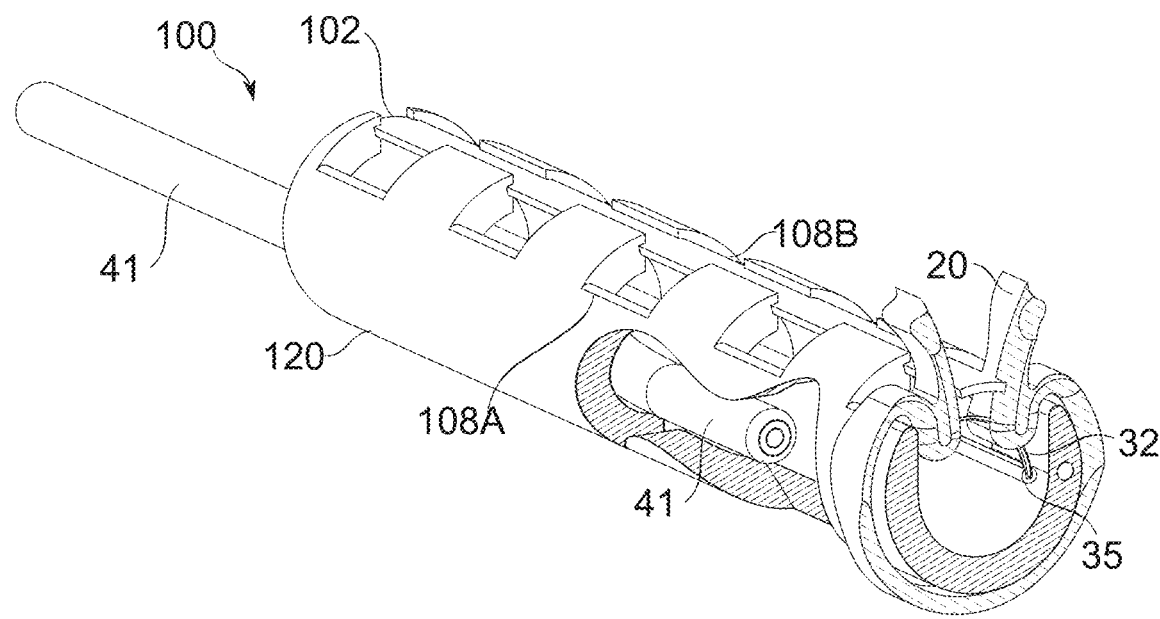
FIG. 12E is a schematic perspective illustration of a fenestrated bougie, wherein suturing by a needle held by a holder is carried out under observation by an endoscope, according to some exemplary embodiments of the invention.

Reference is now made to FIG. 12E, which is a schematic perspective illustration of a fenestrated bougie 100, wherein suturing by a needle 32 held by a holder 35 is carried out under observation by an endoscope 41, according to some exemplary embodiments of the invention.

FIG. 12E shows an exemplary instance of constraints within a bougie 100 during operations for suturing a gastric sleeve. A section of tissue 20 is shown wrapped around the body of the bougie 120, with fenestrations 108A, 108B separated by a blocker 102. Needle holder 35 and endoscope 41 are inserted in parallel to the bougie 100, and separately operated to allow suturing under visual observation.

In some embodiments, a separate needle holder 35 is omitted, and an attachment assisting apparatus (such as an automatic suturing or stapling device) is attached to the end of endoscope 41 and used for forming attachments between opposite gastric wall portions.

Figure 12F:
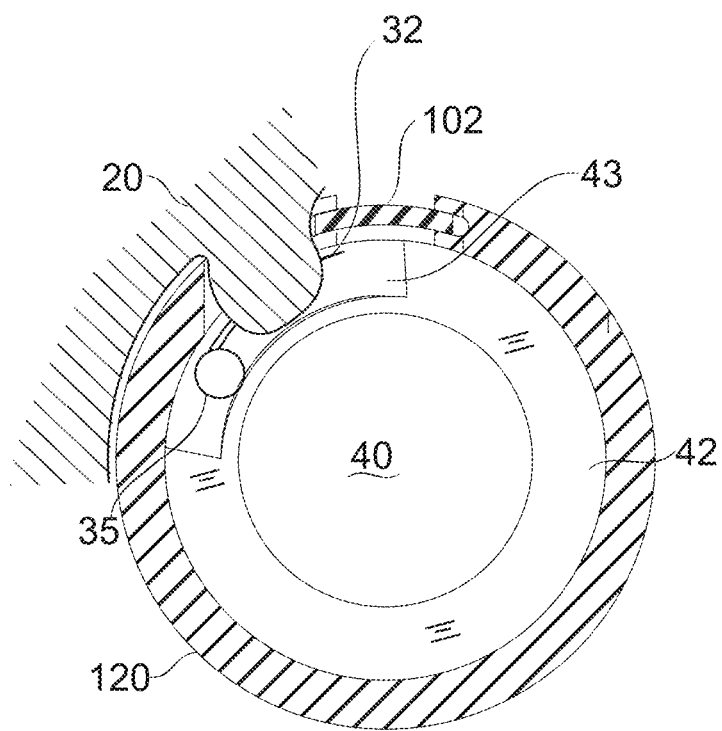
FIG. 12F is schematic cross section of a bougie body having a slot region for assisting positioning of a needle, according to some exemplary embodiments of the invention.

Reference is now made to FIG. 12F, which is schematic cross section of a bougie body 120, having a slot region 43 for assisting positioning of a needle 32, according to some exemplary embodiments of the invention.

In some embodiments of the invention, the lumen 40 of bougie body 120 comprises one or more partial rings 42, each ring 42 comprising a slot region 43 sized for the passage of a needle holder 35 thereinto (e.g., from a longitudinal direction), and therealong (e.g., around the circumference of the bougie). Optionally, the central region of lumen 40 is left open, for example allow passage of an observation device therethrough. Optionally slot region 43 enforces guidance of the movement of needle holder 35, such that the needle 32 is passed into the targeted level of tissue 20.

Returning now to FIG. 1E, at block 174, in some embodiments, a determination is made as to whether or not the last site has been sutured. If not, flow continues, in some embodiments, at block 171. Alternatively, flow returns to block 172 for adjustment of secondary stabilization, or directly to suturing of the next site.

Otherwise, optionally at block 176, the blocker 102 is withdrawn, if it has not been withdrawn during the previous course of suturing. In some embodiments, this frees bougie 100 from suturing-in that has occurred around a blocker left in place during the surgery. At block 178, in some embodiments, the bougie is withdrawn, including, for example, release of vacuum, any maneuvering of the bougie required to release it from sutures and/or remaining intrusions by the wall, and/or deflation of anchoring balloons 104, 106.

At block 180, in some embodiments, finalization of the gastric sleeve is performed. This can include, for example, final tightening of sutures, inspection of the results, and/or supplementary suturing as required (the sleeve itself having already been substantially formed). Supplementary suturing is optionally performed, for example, to reduce gaps of excessive size which may be noted between sutures (which might allow food to pass), and/or to extend the sleeve section to reach closer to an end of the stomach (the end of pylorus or the esophagus). Here the description of the flow chart of FIG. 1E ends.

Blocker and Fenestration Features and Parameters

Figure 7E:
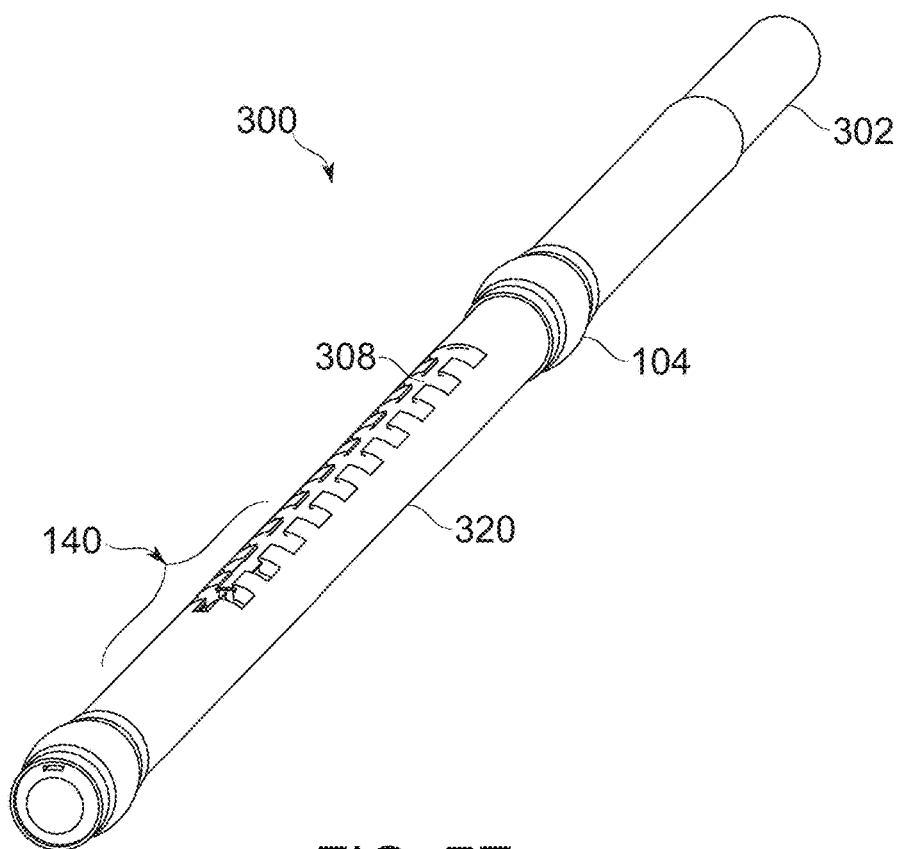
FIGS. 7E-7F schematically illustrate perspective and perspective detail views of a bougie, according to some exemplary embodiments of the invention.
Figure 7F:
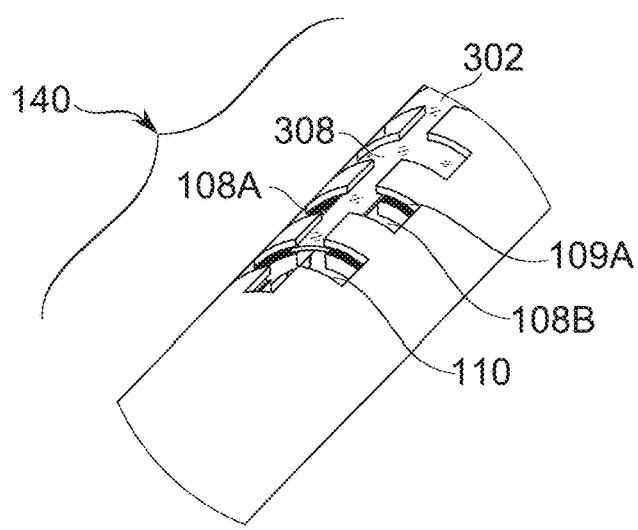
Figures 7G, 7H, 7I, 7J:
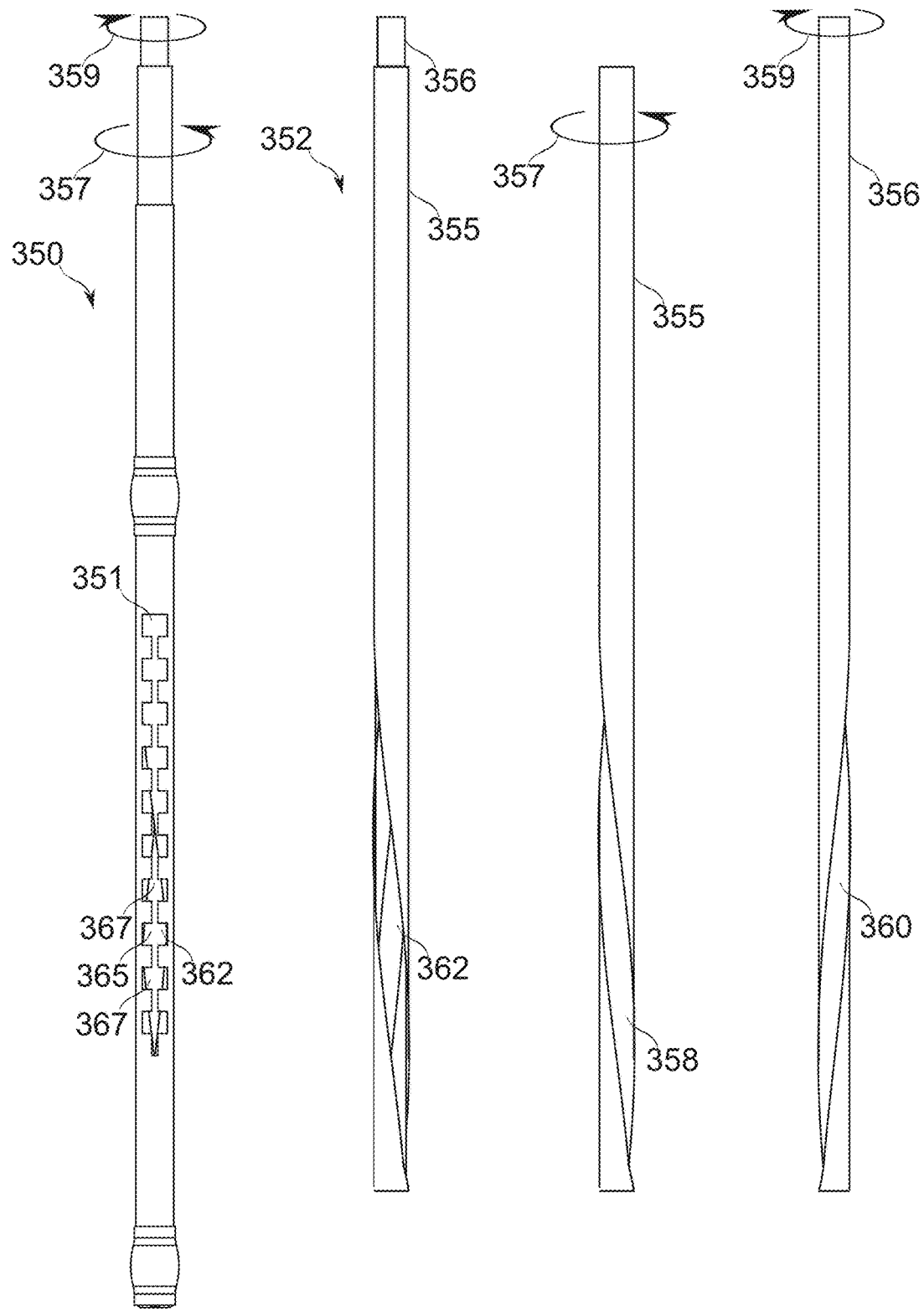
FIGS. 7G-7J schematically illustrate a bougie comprising a blocker for which the size and/or position of the blocking region is controlled by helical motion, according to some exemplary embodiments of the invention.

Reference is now made to FIGS. 7A-7D, which schematically illustrate a bougie 300 configured with a blocker slider 302 shaped to allow both full and partial blockage of positioning/suture fenestrations 108A, 108B, 110, according to some exemplary embodiments of the invention. Reference is also made to FIGS. 7E-7F, which schematically illustrate perspective and perspective detail views of bougie 300, according to some exemplary embodiments of the invention. FIG. 7F shows a detailed view of region 140 of bougie 300 of FIG. 7E.

In some embodiments, a bougie 300 comprises a blocker 302 extending through a portion of bougie body 320, wherein the blocker 302 is positionable to block one or more fenestrations 308 entirely.

In some embodiments, blocker 302 extends laterally, for a portion 302A of its length, across a sufficient lateral arc of the circumference of the bougie 300 to block the whole width of fenestrations 108A, 108B. Optionally, the blocker 302 comprises through a part of this length a whole tube that fits within or around bougie 300. In some embodiments, when blocker 302 is not an entire tube, a slot 109A is provided of sufficient width to hold the wide blocker 302.

In some embodiments, blocker 302 comprises a thin section 302C, which is sufficiently narrow that fenestrations 108A 108B are partially open when section 302C is positioned (for example, by proximal withdrawal of blocker 302) at their level along the length of the bougie 300. In some embodiments, being partially open allows suction of gastric wall tissue 20 into the fenestrations 108A 108B for stabilization, without deep intrusion that interferes with suturing activity. In some embodiments, further withdrawal of the distal end 302B of blocker 302 past a fenestration pair 108A, 108B allows the fenestrations to merge to a single fenestration 110.

In some embodiments, variation of fenestration exposure is controlled by motion of a blocker (102, 302, or another blocker) along the distal-proximal axis. Additionally or alternatively, rotation of a blocker changes fenestration exposure. For example, a tube-like blocker optionally comprises an open region with at least one diagonally oriented (helical) side. The degree and/or position of fenestration opening is then controllable at least in part by the rotational position of the blocker.

Reference is now made to FIGS. 7G-7J, which schematically illustrate a bougie 350 comprising a blocker 352 for which the size and/or position of the blocking region is controlled by helical motion, according to some exemplary embodiments of the invention.

In some embodiments, a blocker 352 comprises at least one blocker portion 355 having a helical slit 358. According to the pitch and width of the slit 358, as blocker portion 355 is rotated (for example in direction 357), the region which faces the fenestrations 351 of the bougie 350 moves along the length of the bougie. In this fashion, a bougie fenestration 351 can be moved to become a fully open fenestration 365 or a partially open fenestration 367, according to the size and position of opening 362. Optionally, a second blocker portion 356 having an opening 360 is used, which optionally comprises a pitch and/or width different than that of opening 358. In some embodiments, the pitches run in opposite directions, allowing the definition of a clear hole 362 between them which can be controlled to move along the length of the bougie 350 according to rotations with or against the directions of arrows 357, 359. Additionally or alternatively, the exposure of opening 362 to the bougie fenestrations 351 is made larger or smaller by different relative motions of the blocker portions 355, 356.

A potential advantage of this method of controlling fenestration opening is to allow gradual movement of gastric wall tissue 20 in and out of selected bougie fenestrations 351, according to the current position of the working region. Optionally, the two blocker portions 355, 356 are worked against each other and/or the walls of the fenestrations themselves in order to pinch gastric wall tissue 20 into place. Additionally or alternatively, the blocker portions 355, 356 can be rotated to "lever" tissue out of the bougie. Optionally, the ability to set the lateral size of the bougie fenestration opening is used to dynamically adjust to the conditions of the tissue wall—for example, opening a larger fenestration where the muscle layer is buried under a thicker layer of mucosa/submucosa, and/or a thinner fenestration where there is more danger of penetrating the wall entirely.

It is to be understood that the helical slots shown need not have perfectly helical edges; optionally, the walls comprise indentations, for example, to better match the shapes of the fenestrations. Additionally or alternatively, by adding horizontal protrusions of blocker material across the slots 358, 360, for example, regions which are never unblocked are defined in some embodiments.

Furthermore, it can be understood that blockers having a "slider" configuration (such as blocker 102), are optionally used together with one or more rotating slot blockers. A vertically slotted blocker, for example, is provided in some embodiments, and optionally rotated to differentially control the penetration depth of one of the two gastric walls relative to the other.

In general, it should be understood that blockers can be provided as more or less tube-like or strip like, in nested and/or adjoining sets, with the slotting and/or width of each blocker portion set to the shapes of the same or different "masks", such that a required type and/or specificity of control over the localization, depth, and extent of gastric wall tissue penetration into the bougie is obtained. Potentially, the provision of greater control allows a practitioner greater ability to adjust suturing depth to patient- and region-specific variations in conditions like gastric wall thickness. On the other hand, in some embodiments, a simpler blocker configuration is chosen, such as only a single blocker, to obtain maximal maneuvering room, efficiency of operation, reproducibility, or another factor.

Figure 8A:
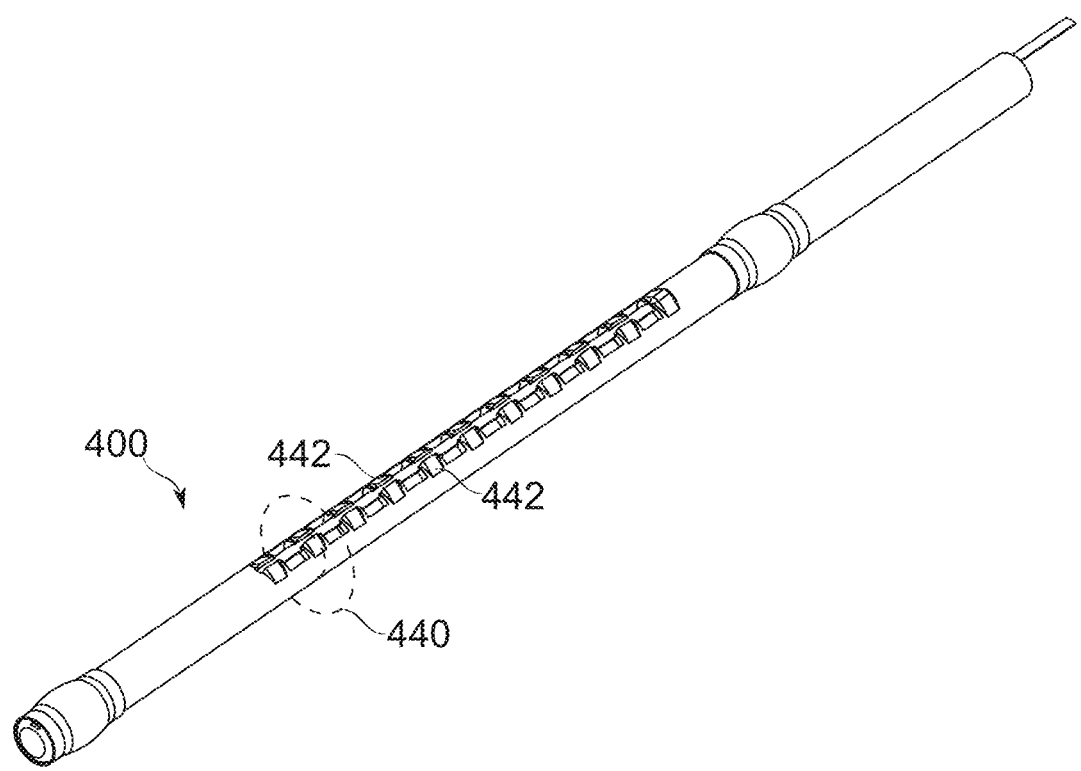
FIGS. 8A-8B schematically illustrate a bougie comprising fenestrations wherein depth of tissue penetration is adjusted by regions of varied wall thickness, according to some exemplary embodiments of the invention.
Figure 8B:
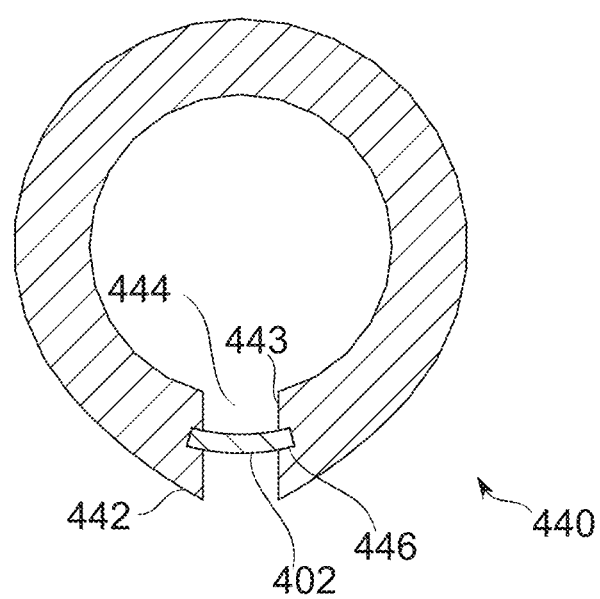
Figure 9A:
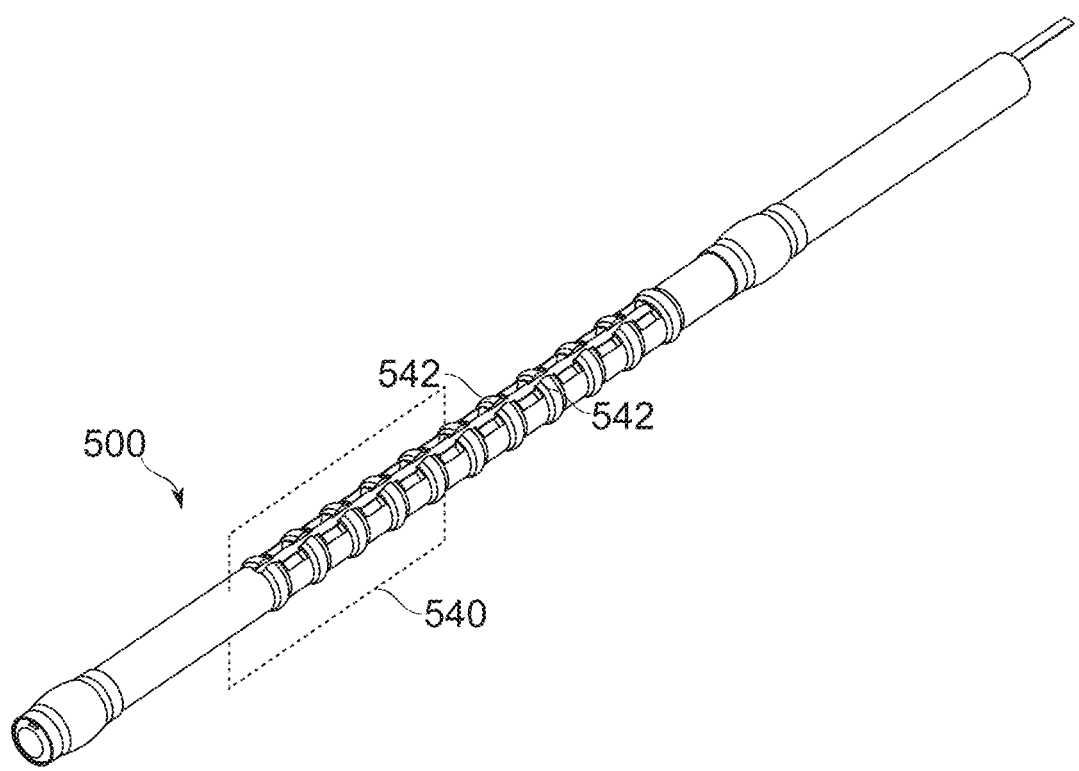
FIGS. 9A-9B schematically illustrate a bougie comprising fenestrations wherein depth of tissue penetration is adjusted by regions of varied wall thickness, according to some exemplary embodiments of the invention.
Figure 9B:
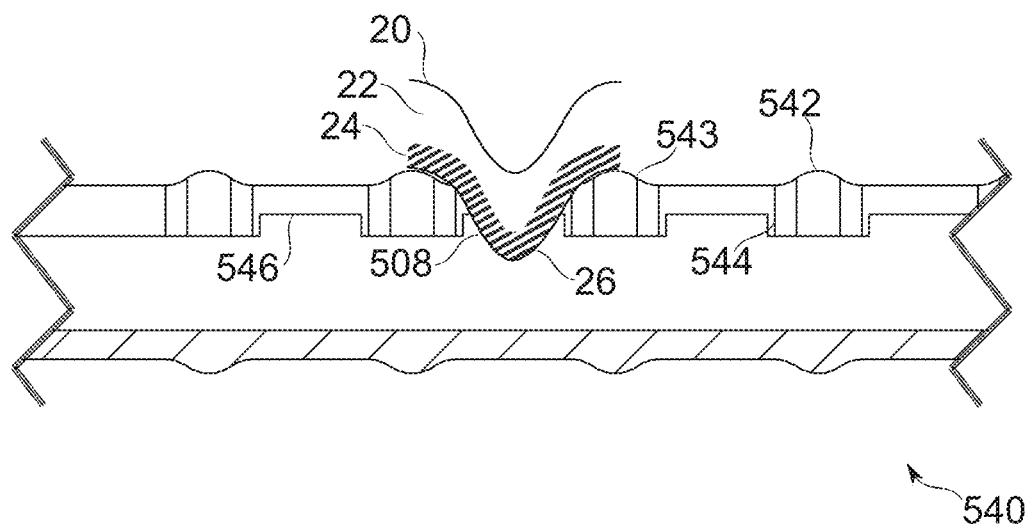
Figure 10I:
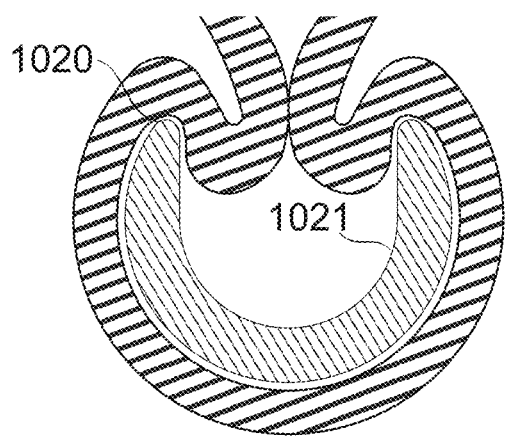
Figure 10J:
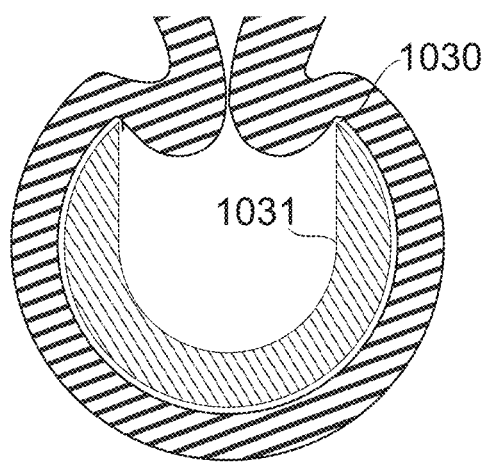
Figure 10K:
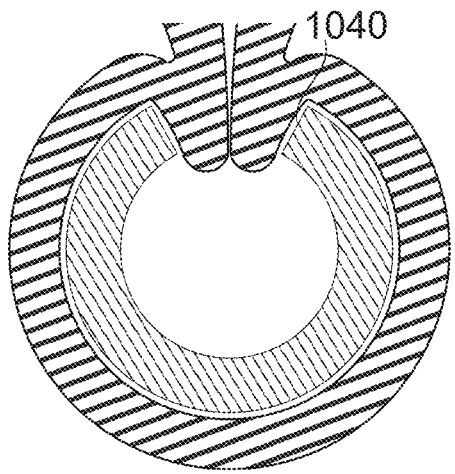
Figure 10L:
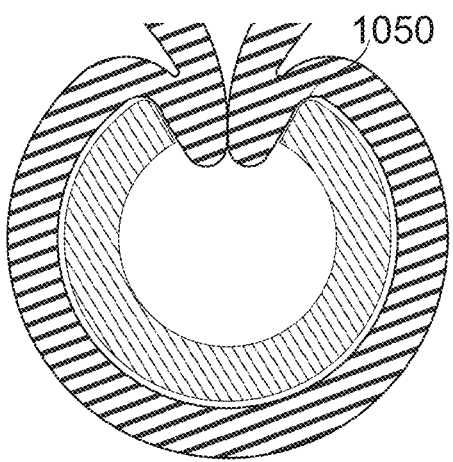
Figure 10M:
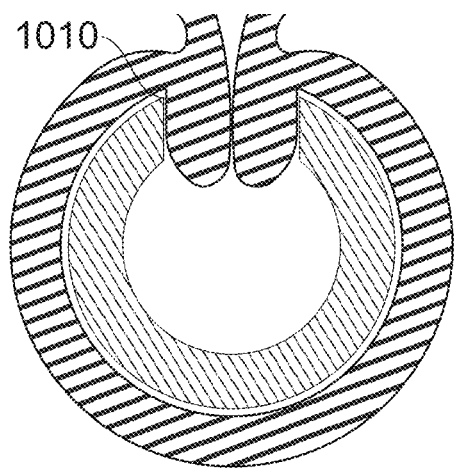

Reference is now made to FIGS. 8A-8B, which schematically illustrate a bougie 400 comprising fenestrations wherein depth of tissue penetration is adjusted by regions of varied wall thickness, according to some exemplary embodiments of the invention. FIG. 8B illustrates a cross-section from region 440 of bougie 400. Reference is also made to FIGS. 9A-9B, which schematically illustrate a bougie 500 comprising fenestrations wherein depth of tissue penetration is adjusted by regions of varied wall thickness, according to some exemplary embodiments of the invention FIG. 9B illustrates a cross-section from region 540 of bougie 500.

In some embodiments, the dimensions of the material defining the fenestrations of the bougie is configured to select the depth of tissue penetration. In FIG. 8A, a bougie 400 is shown having raised regions 442 along its length. The raised regions tend to increase the wall thickness 443 around the fenestration, such that a lesser thickness of gastric wall 20 is exposed to suturing. In particular, a depth of tissue intrusion in the region between suturing fenestrations is reduced, while maintaining the power to participate in vacuum fixation. The raised portion 442 of the wall adds, for example, 1 mm, 2 mm, 3 mm, or another greater, lesser, or intermediate thickness to the wall portion adjoining a fenestration 444. In some embodiments, the thickened wall allows providing greater support to a blocker 402, for example by allowing a larger and/or more robust slot 446 to be cut into the wall at that point. This is a potential advantage for a bougie which needs to withstand, for example, about 0.5 bar gauge of vacuum pressure.

In FIGS. 9A-8B, the raised sections 542 extend for a greater distance round the circumference of the bougie, showing another shape which is possible. Another option is to change the height of the raised sections at various positions along the bougie; for example, such that less penetration is allowed at portions of the stomach wall which are thinner, and thus more liable to accidental penetration by a needle. FIG. 9B also shows again the relative depth of tissue penetration into a bougie. The relatively thick rings 542 (the thickness being defined, for example, by wall edge 544 and/or by thicker regions near the middle of the ring) potentially allow the intervening portions 546 to be built relatively thinner, and still be sufficiently able to stand the vacuum pressure. This potentially allows greater room for maneuvering at the level of the suturing area and/or allows greater exposure of muscle layer 22, without requiring correspondingly deeper penetration of the mucosal/submucosal layer 24 and the inner surface 26.

In some embodiments, slope 543 is adjusted so that the tissue sloping inward from the point of maximum stand-off of protrusion 542 is guided to an angle allowing the best penetration across the length of the fenestration 508.

Reference is now made to FIGS. 10A-10M, which schematically illustrate different dimensions and shapes of fenestrations and supporting wall, having different effects on function, according to some exemplary embodiments of the invention.

In general the fenestrations 108A, 108B, related to as comprising two rows, can also be considered as a single row of fenestrations 110 separated by a blocker 102. FIG. 10A illustrates this by labeling two fenestration halves 1000A, 1000B, above another fenestration labeled overall as 1000. Fenestrations 1000 are optionally joined by a thinner region 1000C; in the limit, region 1000C is so thin that it disappears, and the fenestrations are entirely separate. Dimensions affecting these relationships include:

overall fenestration width 1003 (which is, for example, 8-10 mm, 9-13 mm, 11-15 mm, 14-17 mm, or another greater, larger, or intermediate width);

joining region width 1004 (which is, for example, 0 mm, 1-2 mm, 2-4 mm, 3-5 mm, or another greater, larger, or intermediate width);

joining region length 1006 (which is, for example, 8-10 mm, 9-13 mm, 11-15 mm, 14-17 mm, or another greater, larger, or intermediate width);

and fenestration length 1005 (which is, for example, 8-10 mm, 9-13 mm, 11-15 mm, 14-17 mm, or another greater, larger, or intermediate width).

One possible consideration constraining the period between fenestrations is the interval for suturing. In a gastric sleeve where a non-filling pocket is to be retained afterward, the sutures need be close enough together to prevent the passage of stomach contents, such that the sleeve forms a distinct compartment. A spacing of about 2 cm is generally sufficient to ensure this, though a different spacing is also used in some embodiments: for example, 1-1.3 cm, 1.3-1.5 cm, 1.5-2.5 cm, 2.3-3.0 cm, or another larger, smaller, or intermediate suture spacing. The distance chosen determines the sum of the distances 1005 and 1006.

As already described, a main consideration affecting the maximum size of a fenestration opening is the thickness of the tissue to be passed through by a suturing needle. Preferably, at least 3-5 mm of tissue are admitted to the bougie lumen, to allow the muscular layer to pass beyond the boundary of the bougie's inner wall. The wall itself may be 2-3 mm or more thick, adding to the thickness that must be admitted beyond the outer diameter of the bougie. Nevertheless, not much more tissue than this should be admitted, to avoid the danger of running a suture entirely out of the gastric wall, and potentially inducing a gastric leak.

Two doubled-over gastric walls comprise a typical thickness in the range of 12-20 mm (at least where they are sharply folded). A long enough fenestration which was at least that wide would potentially be able to admit tissue all the way to the other side of the bougie. This would, in general, be too much tissue, as it would potentially bring the outer surface of the gastric wall within the bougie. The bougie outer diameter itself is limited to about 20 mm (11-20 mm is a typical range), in order to pass the esophagus. Nevertheless, a maximally open 20 mm bougie having a wall thickness 1013 of 2 mm would fall right on the edge of the range that could admit the whole doubled-over thicknesses of the wall. It is preferably provided, in some embodiments, for the fenestration height 1005 to be small enough (for example, 8-10 mm, 9-12 mm, 11-14 mm, or another larger or smaller height) that the desired penetration range is not exceeded. In some embodiments, the fenestration is additionally or alternatively narrowed, allowing the curve of the bougie to decrease the admission aperture of the fenestration on each side by a distance 1012.

So long as sufficient tissue is admitted to the bougie, there is a potential advantage to admitting tissue to the bougie with a sharp angle, such that a needle is faced with a sharp "cliff" of tissue, rather than a gradual rise. During suturing, the needle itself, though itself quite thin, tends to be only a short distance in advance of a thicker holding means, which is more limited in maneuvering space. In view of this, the "cliff" is potentially most important on the side of the fenestration from which the needle approaches. However, subjecting the tissue to sharp bends also potentially reduces the tendency of the tissue to slide around, since it must pass through a sharper bend to do so.

Nevertheless, the acute angle that wall 1011 or 1031 makes with the outer diameter of the bougie tends to create a sharp edge 1010 or 1030 which is a potential source of unnecessary injury due to the level of vacuum pressure pulling on the gastric wall. In some embodiments, a rounded edge 1020, 1050 is instead provided, which potentially softens access to even a sharp-angling wall like wall 1021. Acute edges can also be reduced by changing the slope which the exposed wall 1040 makes with the circumference of the bougie. This can potentially also have the effect of changing the apparent thickness of the wall edge 1041.

In some embodiments, the change in slope also is used to control the amount of tissue admitted; for example, for the same distance 1012, a more acute external angle will potentially tend to exclude more tissue, but the tissue which does enter the bougie will potentially tend to do so in a more parallel configuration. It can, conversely, be understood that a more deeply chamfered edge potentially allows deeper penetration of tissue into the bougie lumen. The effect of the cutaway regions on bougie wall strength should also be taken into account, since the more wall material that is removed from the ideal "complete" shape, the more liable the wall is to collapse under vacuum.

A sharp fenestration corner is in general too confined to have a great effect on the admission of tissue, but also comprises a potential source of unwarranted injury. In some embodiments of the invention, fenestration corners 1007A, 1007B, 1007C, 1007D are rounded (with a radius of curvature of, for example, about 1 mm, 2 mm, 3 mm, or another larger, smaller, or intermediate radius). Optionally, the curves are different at different corners. For example, rounding can be greater on the edge away from the suturing tools, since a softer curve there is less likely to result in hindrance of access.

In some embodiments, the two fenestration halves are staggered from one another along the length of the bougie. The staggering distance is optionally any fraction of the fenestration period. A potential advantage of staggering the rows is to allow alternate exposure of left and right sides. Potentially, this leaves more maneuvering room at each level. In the case where a suturing machine is used, it can be useful to stagger, to allow more certainty that each wall side is being grabbed in alternation, and, where necessary, that the suturing device is properly fit around the tissue intrusion for suturing. The period of suturing (determined by the sum of the distances 1008A, 1008B) is variable, for example, as described in relation to the period determined by the sum of distances 1005, 1006.

Using an offset which is smaller than 50% of the period (for example, 30%, 40%, or another larger, smaller, or intermediate offset) has the potential advantage of easing the task of cinching the walls together after suturing is finished. For example, less relative motion is required, in such a case, to achieve the tightest suture closure.

In some embodiments of the invention, the slope leading from the outer wall of the bougie to the inner wall of the bougie, which is defined by the walls of the fenestrations running perpendicular to the bougie longitudinal axis, is selected according to one or more functional considerations.

For a reference embodiment, the slope can be considered as running perpendicular to the transverse plane of the bougie. If the slope of the more proximal fenestration wall runs distal-to-proximal (e.g., outer to inner), and/or if the slope of the more distal fenestration wall runs proximal to distal, the effect is of a more open interior, which potentially helps to promote access to tissue.

The more open interior is also potentially more difficult to force tissue out of. Potentially, open-inward fenestration walls allow the tissue more room to expand, and thus become lodged. This is a potential advantage for stability, and particularly so if a shearing or pinching force can be brought to bear (for example, by pulling and/or rotating on a blocker element). On the other hand, in some embodiments, it is potentially beneficial to allow tissue to be more easily coaxed out of the fenestrations. For example, an embodiment where a restricted window moves along the length of the bougie must be able to effectively push tissue back out of the fenestration in order to move more proximally. In some embodiments, the slope of one or both of the fenestration walls running perpendicular to the bougie length is set so that the fenestration becomes larger toward the outside of the bougie wall, which potentially assists this. In some embodiments, the slopes run in parallel directions, such that pressure from one side tends to result in "pinching", while pressure from the other side tends to result in elevation and extraction.

Figure 11A:
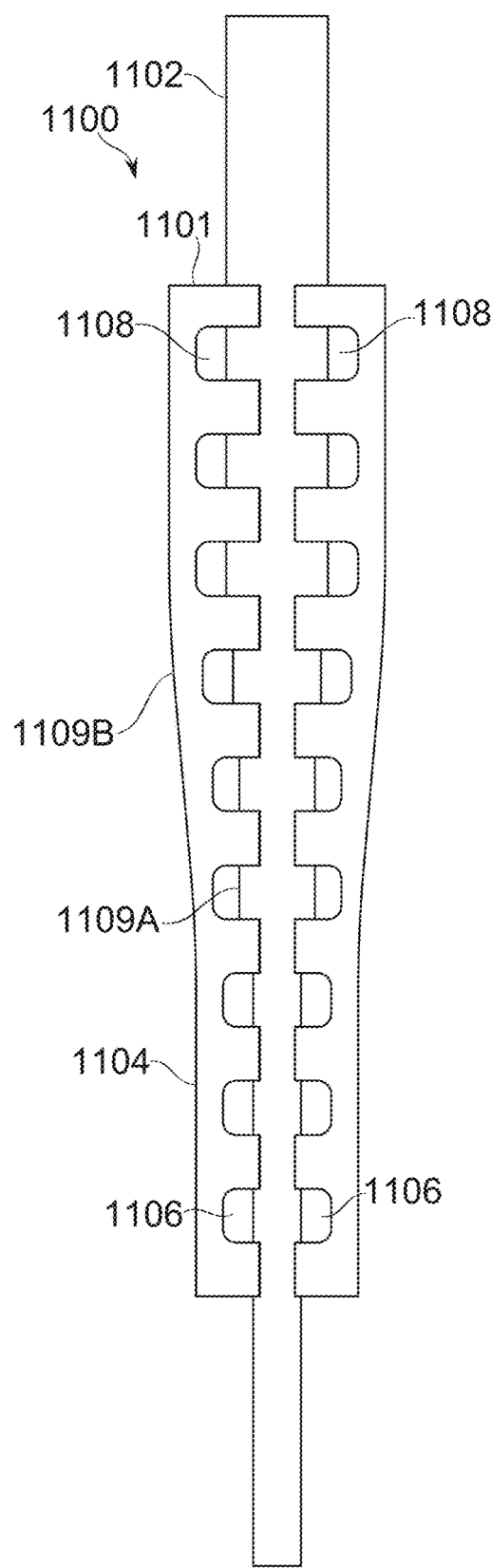
FIGS. 11A-11C schematically illustrate bougies having variable width, variable fenestration dimensions, and/or variable blocker dimensions, according to some exemplary embodiments of the invention.
Figure 11B:
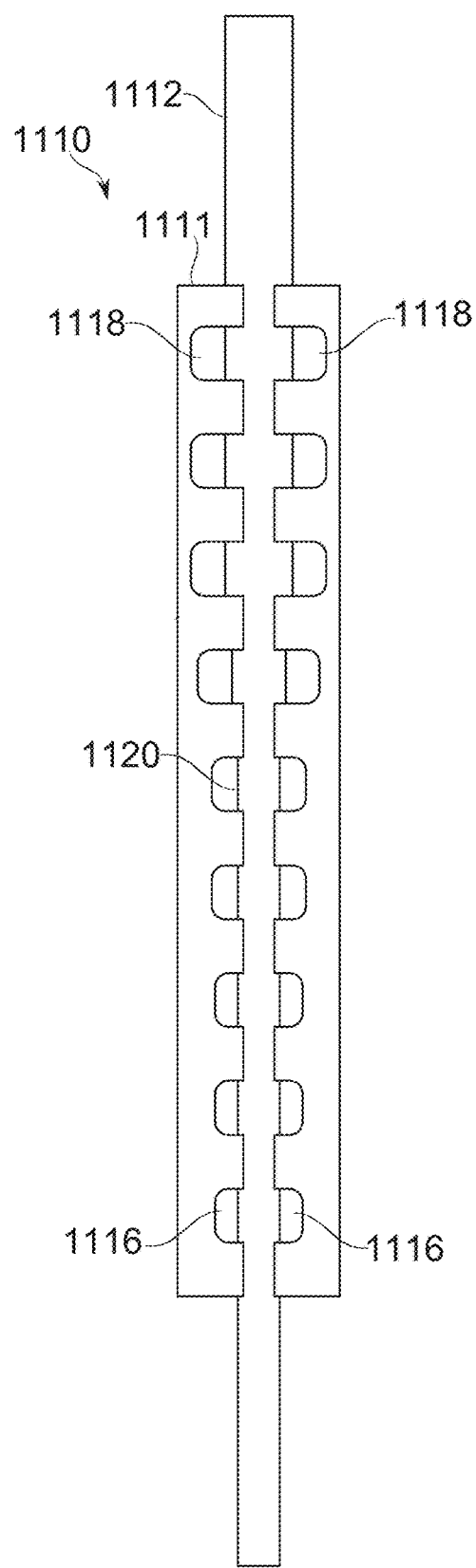
Figure 11C:
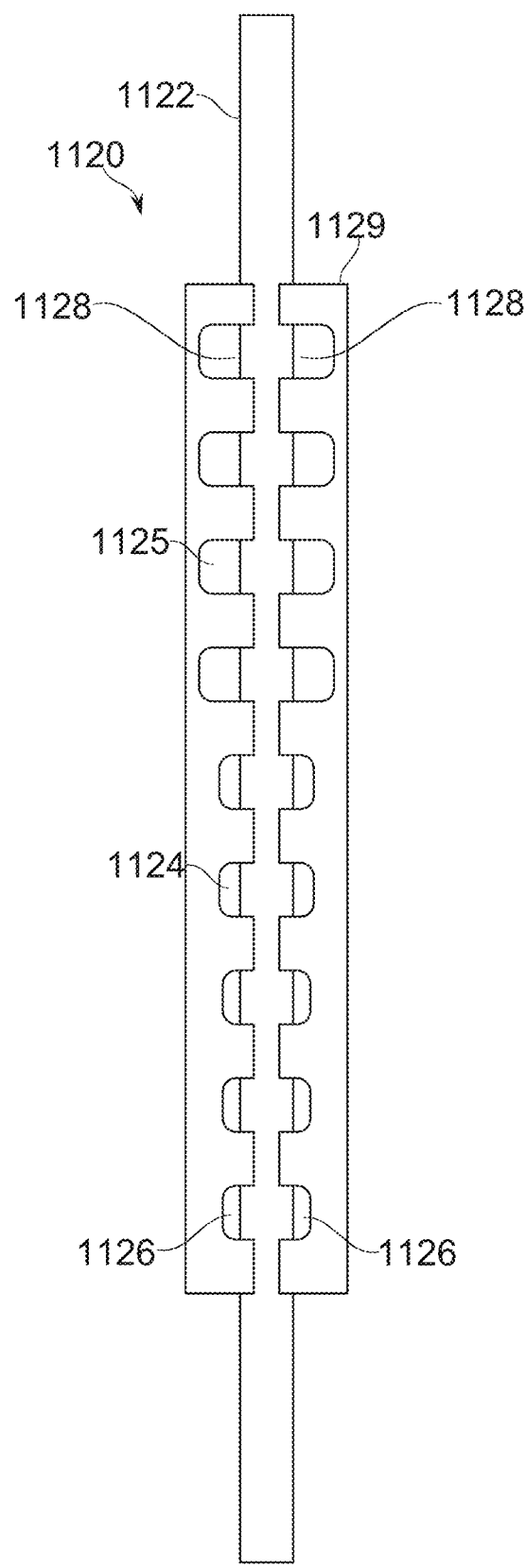
Figure 11D:
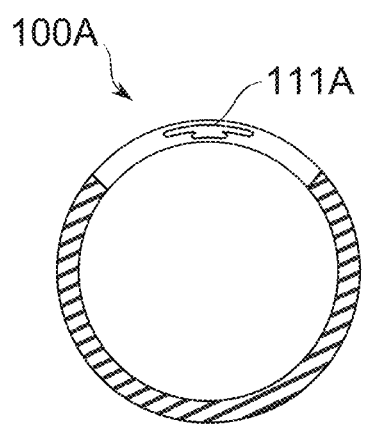
FIGS. 11D-11G show alternative arrangements of bougie blockers, and their mounting regions, according to some exemplary embodiments of the invention.
Figure 11E:
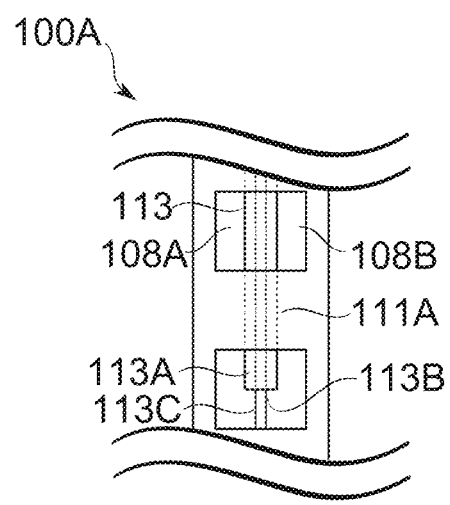
Figure 11F:
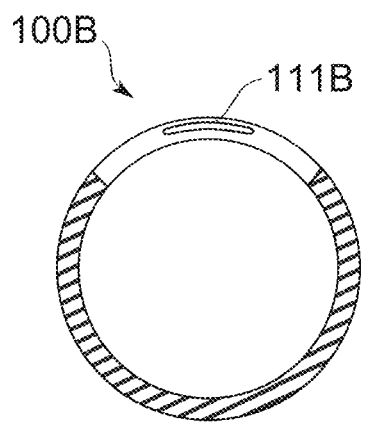
Figure 11G:
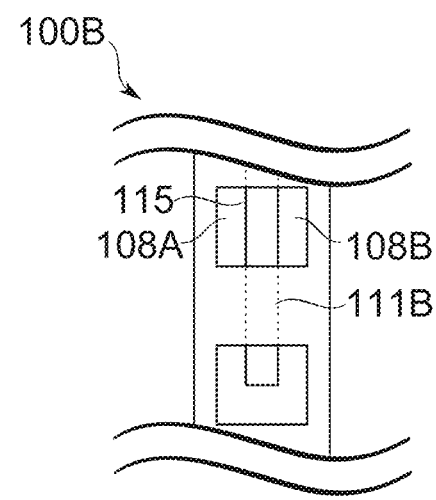

Reference is now made to FIGS. 11A-11C, which schematically illustrate bougies 1100, 1110, 1120 having variable width, variable fenestration dimensions, and/or variable blocker dimensions, according to some exemplary embodiments of the invention. It is to be understood that the horizontal and vertical dimensions are not necessarily shown to scale, in order to illustrate differences more clearly.

In some embodiments of the invention, a diameter of a bougie body 1101 is variable from a distal to a proximal direction, sloping wider through a region 1109B, for example, from a smaller diameter at distal end 1104 to a wider diameter. For a fixed fenestration size and position, this would potentially allow templating of a gastric sleeve with a larger lumen near the esophagus, narrowing distally. However, in the example shown, distal fenestrations 1106 are narrower in their maximum width than proximal fenestrations 1108. Potentially, this results in the circumference of the gastric tube being maintained as roughly equivalent along the tube, once sutures are cinched tight at the end of the procedure. It is to be understood that other intermediate results can occur, depending on the relative change in bougie diameter and fenestration width.

A potential advantage of this variability is to allow the bougie to be adapted to a typical anatomically observed situation, wherein gastric wall tissue near to the esophagus/cardia is relatively thick, growing thinner nearing the region of the pylorus. Furthermore, gastric wall convolutions are potentially deeper near regions of thicker mucosa/submucosa. By providing fenestrations adapted to this variability, a potential advantage is derived wherein the balance between deep-enough suturing (to reach muscle) and not-too-deep suturing (to avoid wall perforation) is separately selectable for each region of the gastric wall.

In some embodiments, blocker 1102 is also adapted to variations in width. For example, the blocker 1102 widens as the bougie/fenestrations widen, so that tissue intrusion is prevented to a similar degree along the bougie length. For example, the blocker region 1109A comprises a region of expanding blocker width.

Maximum differences in bougie width in general fall within the bounds set by a typical 11-20 mm bougie diameter. In some embodiments, variability falls within 1-9 mm of bougie outer diameter, or, for example, 1-3 mm, 2-4 mm, 3-6 mm, or another range of variability having the same, larger, smaller, and/or intermediate bounds. While width is shown in FIG. 11A as the particular fenestration dimension which varies, it should be understood that any of the fenestration dimensions described, for example, in relation to FIGS. 10A-10M, could also be varied as a function of length along the bougie.

Optionally, the variability of dimensions is in only one or two of the aspects of fenestration size, blocker size, and bougie body size. For example in FIG. 11B, the outer diameter of bougie body 1111 is constant. Proximal fenestrations 1118 are larger (wider, in the example) than distal fenestrations 1116. Region 1120 of blocker 1112 marks a region of blocker width transitioning from narrow near the distal fenestrations to wider near the proximal fenestrations. Optionally, only one of the aspects changes. For example, in FIG. 11C, blocker 1122 and bougie body 1129 have fixed widths, while proximal fenestrations 1128 are wider than distal fenestrations 1126, the fenestration width being shown transitioning progressively at, for example, fenestrations 1124 and 1125.

Reference is now made to FIGS. 11D-11G, which show alternative arrangements of bougie blockers 113, 115 and their mounting regions, according to some exemplary embodiments of the invention.

In some embodiments, a bougie 100A is configured with a two-part blocker 113. Optionally, the first part 113A is the wider part. The wider part, as it is withdrawn, has the role, for example, of transitioning the interaction of fenestrations 108A, 108B with gastric wall tissue from excluding-and-fixating, initially, to including-for-suturing. The narrower part, 113C, is optionally used to provide continued fixation of sutured regions to the bougie during the procedure, being broken and/or withdrawn only at the end of the procedure. In some embodiments, narrow blocker part 113C is narrow enough that it substantially allows the gastric wall tissue to pass by it, once the distal end 113B of the wider blocker part 113A is withdrawn from a fenestration pair. In some embodiments, the wall of the bougie 100A comprises a slot 111A, or pair of slots, shaped to support the blockers before removal. It is a potential advantage to leave the fenestrations fully un-joined (a bridge in the bougie wall around slot 111A), in order to provide additional support for the thinner blocker.

In some embodiments, a bougie 100B comprises a single sliding blocker 115 (optionally, a blocker much like blocker 102). The bougie body itself optionally fully separates the fenestration pairs from each other. Optionally, an aperture slot 111B holds the sliding blocker 115 in place until its removal.

Reference is now made to FIGS. 12A-12D, which schematically illustrate different shapes of bougie bodies 1200, 1208, 1210, 1220 according to some exemplary embodiments of the invention.

In some embodiments of the invention, a bougie body 1210 is substantially circular, except, for example, where interrupted by fenestration gaps 1204, and/or apertures or slots 1202 for a blocker.

In some embodiments, the walls of a bougie 1200 are thinned near the fenestration apertures 1204, for example at wall region 1206. Wall thinning near the apertures is also described in connection to wall thickening between apertures, for example, in relation to FIGS. 8A-9B, hereinabove.

In some embodiments, the overall bougie shape is non-circular. For example, bougie body 1208 is shown with an oval shape. A potential advantage of a non-circular shape is to allow a wider admission aperture at the fenestration opening, with the tradeoff of a narrower bougie depth (which, optionally, is not required for sufficient admission of tissue).

In another embodiment type, shown in FIG. 12D, a bougie body 1220 comprises a long slit 1222, sized to pass a wide blocker, and/or a blocker having a width variable over a large range. Optionally, the slit 1222 is wider than the fenestration aperture 1224, allowing full blockage of the fenestration by a sufficiently wide blocker, for example as described also in relation to FIGS. 7A-7F hereinabove.

Figures 13A, 13B:
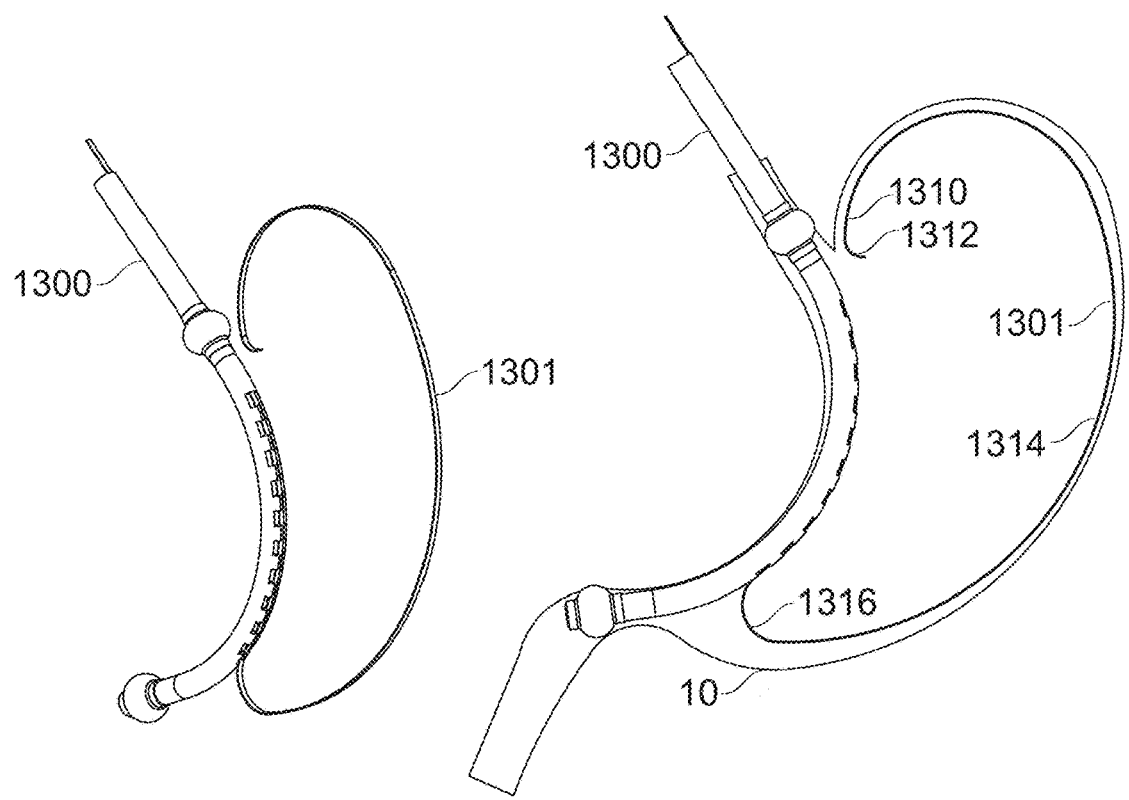
FIGS. 13A-13C show bougies, comprising stomach positioning/sizing extensions, according to some exemplary embodiments of the invention.
Figure 13C:
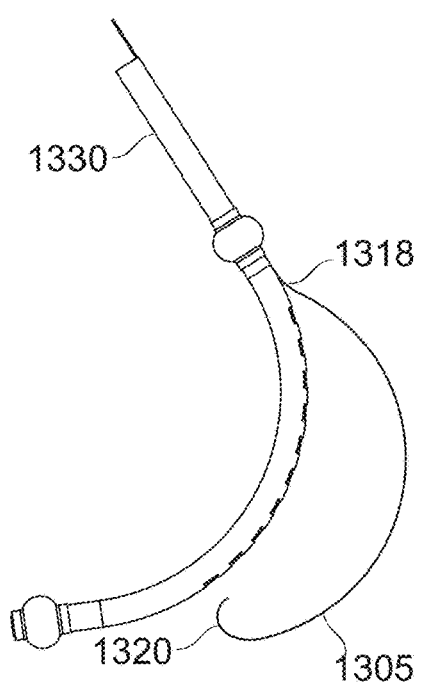

Reference is now made to FIGS. 13A-13C, which show bougies 1300, 1330 comprising stomach positioning/sizing extensions 1301, 1305, according to some exemplary embodiments of the invention.

In some embodiments of the invention, a bougie 1300, 1330 is provided with a sizing extension 1301, 1305, which helps to position the stomach in preparation for suturing.

In some embodiments, sizing extension 1301 comprises a strip of a formed material, for example, nitinol. Optionally, the extension strip is passed into the stomach along a slot within bougie 1300, extrudes from near the distal end of the bougie, and wraps around to form the final stomach-shaping brace. The stomach shaping brace comprises, for example, a narrower region at strip region 1316, where the stomach narrows before merging with the pylorus; a wider region 1314 at correspondingly wider regions of the stomach; a backward curve 1310 which reaches to the area of the cardia, and/or a protective termination 1312, which can be a tight curl of the strip, or simply comprise an atraumatic tip material such as silicone rubber or another soft material. It is a potential advantage to use nitinol, which has the ability to assume a straightened shape during passage through the bougie, while still returning fully to its natural formed shape once it is able to expand against the stomach wall. It should be understood that a sizing extension 1301 need not span the full extent of the stomach. In some embodiments, its role as a straightener is fulfilled by a relatively short extension outward from the bougie. In some embodiments, extension 1301 also serves as a wall separator, ensuring that the left and right gastric walls mate with the appropriate fenestration regions upon application of suction.

In some embodiments of the invention, bougie 1330 comprises a sizing extension 1305 which exits the bougie body at a more proximal point 1318, with a distal terminus 1320 at or near the region of the pylorus.

Figure 13D:
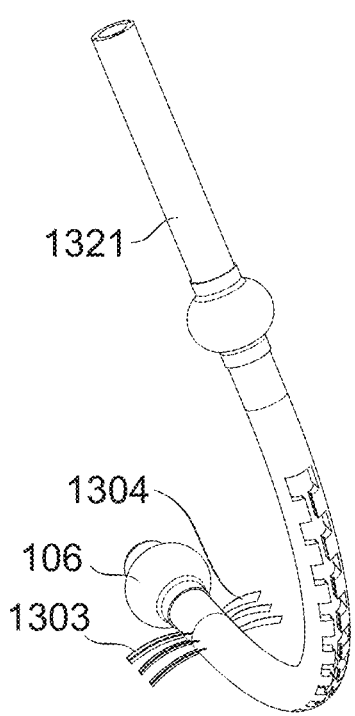
FIGS. 13D-13E show bougies, comprising pylorus positioning/sizing extensions, according to some exemplary embodiments of the invention.
Figure 13E:
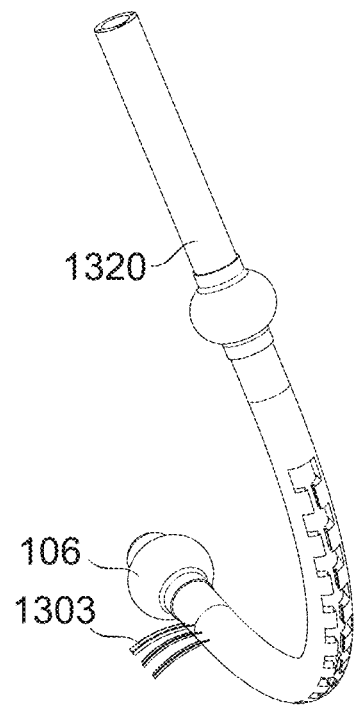

Reference is now made to FIGS. 13D-13E, which show bougies 1321, 1320, comprising pylorus positioning/sizing extensions 1303, 1304, according to some exemplary embodiments of the invention.

In some embodiments, positioning of a bougie 1321, 1320 is assisted in the region of the pylorus by the provision of bracing fins 1303, 1304. In some embodiments, bracing fins 1303 are provided only on one side, in view of gastric asymmetry in the region of the pylorus, and allowing the bougie to be urged toward the side of the stomach from which the pylorus issues. In some embodiments, bilateral fins 1303, 1304 are provided. Optionally, fins 1304 are somewhat weaker than fins 1303, so that they distance the bougie from the gastric wall, but still allow the bougie to be urged to the side of the stomach from which the pylorus issues. Optionally, the finds bend out of the way to allow insertion and extraction. Optionally, inflation of balloon 106 (or provision of presser via another inflation fluid pathway) drives fluid such that the fins 1303, 1304 are stiffened/erected by the inflation pressure. This is a potential advantage to allow easier insertion/removal. Optionally the fins are made of nitinol which can be driven out of/withdrawn into the bougie by the advancement/retraction of a controller member fixed to them, with the control located outside the bougie. Optionally, the fins are made of a polymer, sufficiently soft that it can collapse upon insertion/removal through the esophagus, but expanding when there is free room to help urge the bougie into the proper position.

Figure 14A:
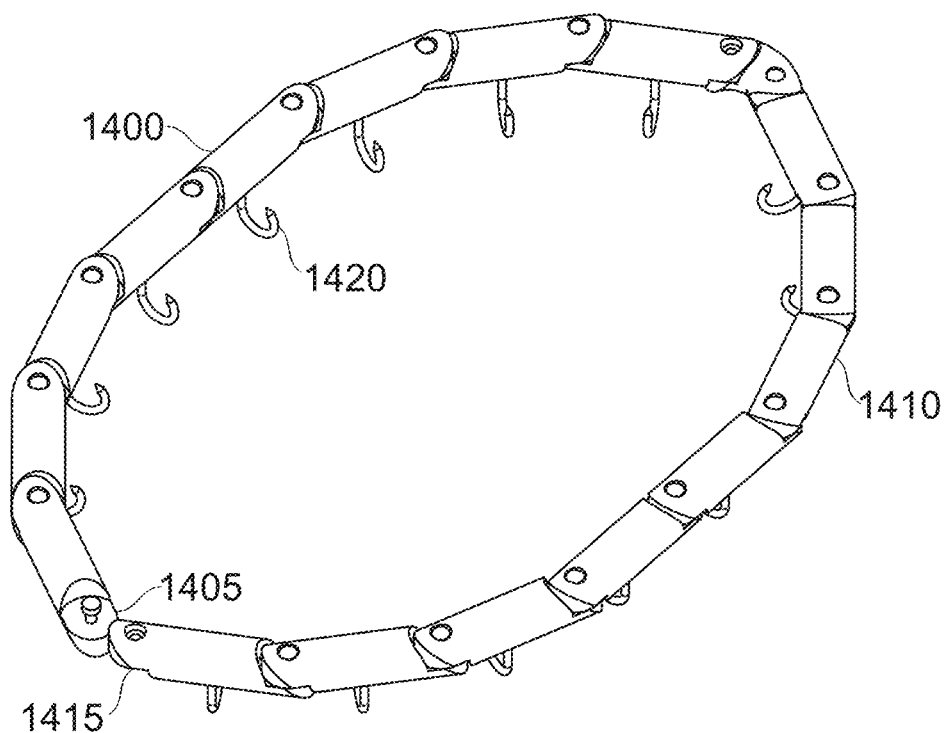
FIGS. 14A-14B show a multi-link gastric implant for forming an intra-gastric sleeve, according to some exemplary embodiments of the invention.
Figure 14B:
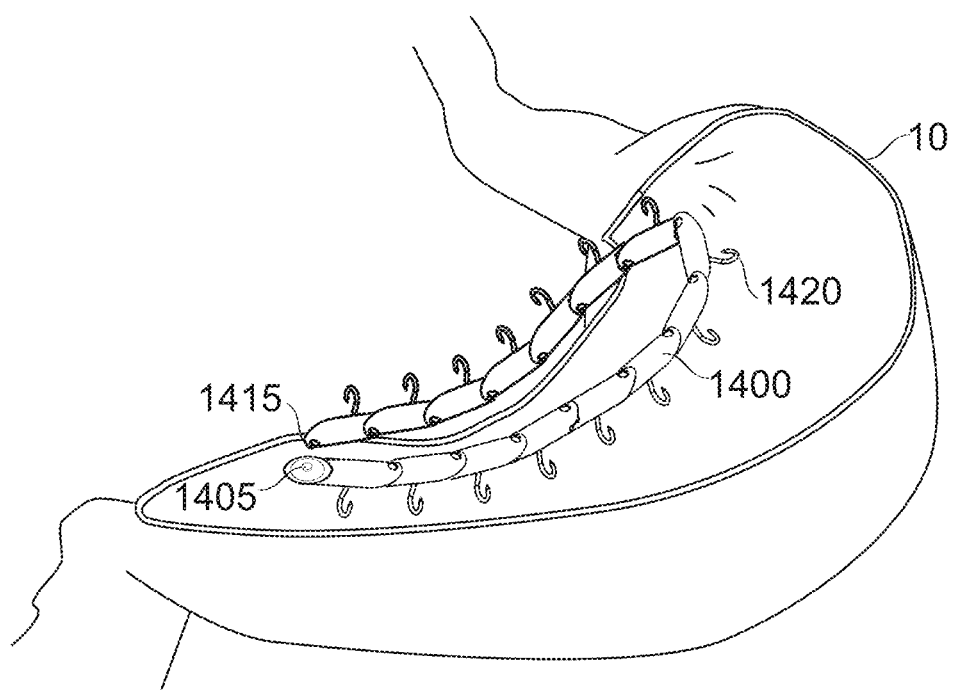
Figure 15:
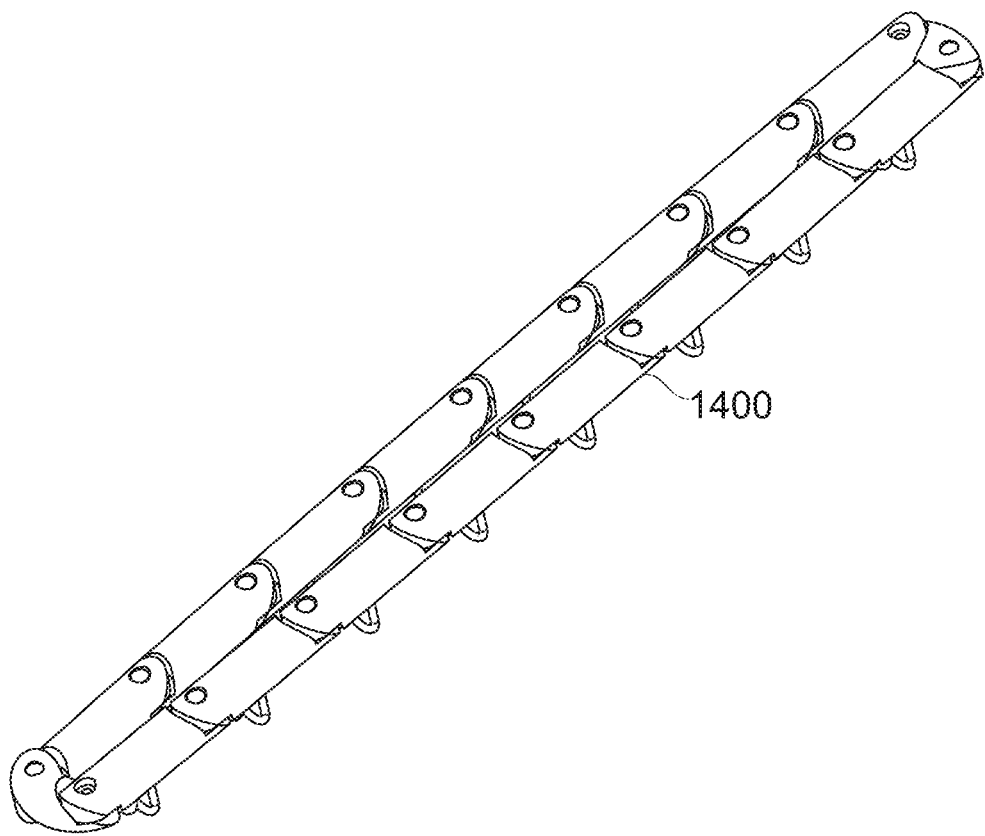
FIG. 15 shows the multi-link gastric implant of FIGS. 14A-14B, straightened according to some exemplary embodiments of the invention.
Figure 16:
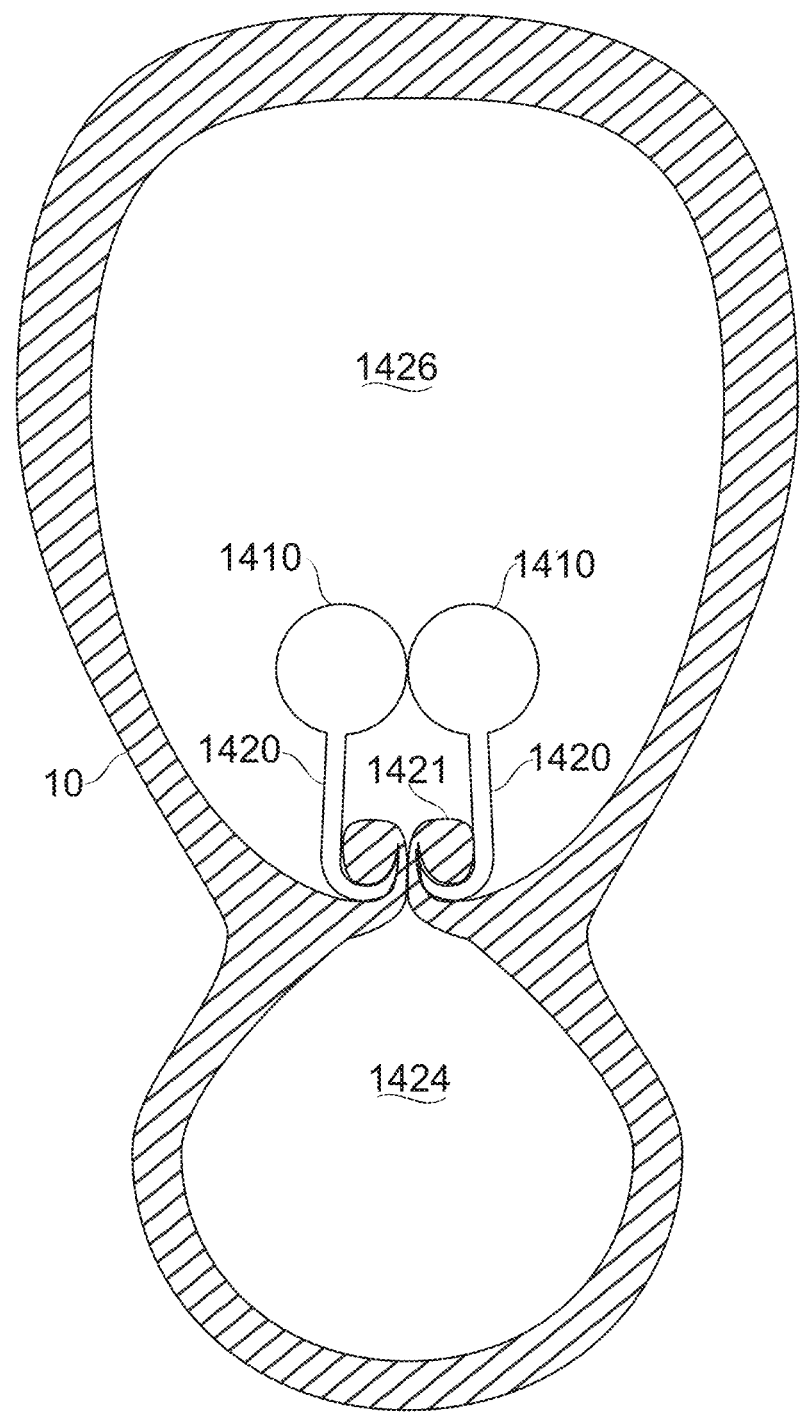
FIG. 16 shows a cross-section of a multi-link gastric implant having gastric wall tissue recruited to its hooks, according to some exemplary embodiments of the invention.

Reference is now made to FIGS. 14A-14B and FIG. 15, which show a multi-link gastric implant for forming an intra-gastric sleeve, according to some exemplary embodiments of the invention. Reference is also made to FIG. 16, which shows a cross-section of a multi-link gastric implant having gastric wall tissue recruited to its hooks, according to some exemplary embodiments of the invention.

In some embodiments, gastric implant 1400 comprises a multi-link implant having hooks 1420. The implant 1400 is inserted to the stomach 10, for example, through a gastroscope's working channel, in an open loop configuration. Optionally, hooks 1420 are collapsed against the sides of the links 1410 during insertion. The implant links are initially free to rotate next to one another, so that they can be positioned around the gastric wall (FIG. 14B). The free ends 1405, 1415 of the implant 1400 are positioned to be near one another, and the loop is closed after positioning. Hooks are deployed, and the gastric walls are harvested over the hook. To form the intra-gastric sleeve, the device is substantially straightened. Straightening is accompanied by locking of adjacent links to one another (FIG. 15). The result is a seam-like region. FIG. 16 shows a cross-section from this region. Links 1410 are mutually locked, with their hooks 1420 engaged with gastric tissue 1421 such that it is essentially captured along two rows—one for each side of the stomach. In some embodiments, the links occupy pouch 1426, leaving the gastric sleeve 1424 (through which food will continue to pass) unobstructed.

Figure 17A:
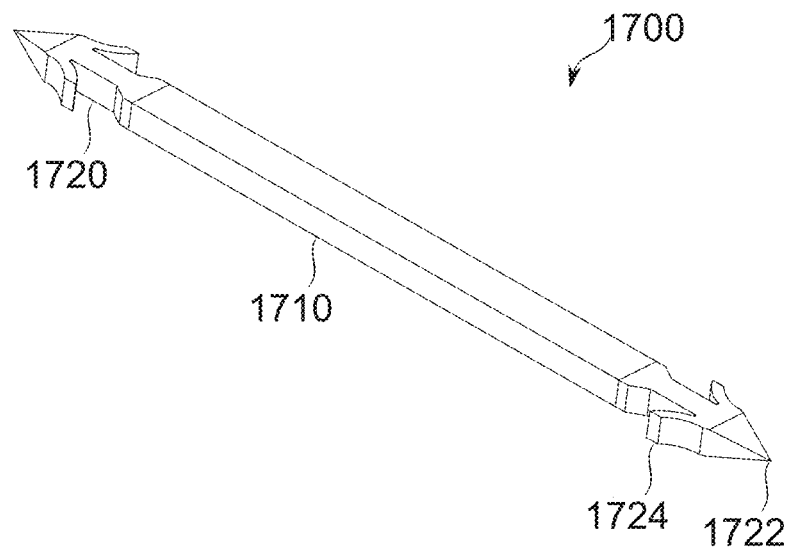
FIGS. 17A-17B show a self-securing clip for securing two gastric wall parts to one another, according to some exemplary embodiments of the invention.
Figure 17B:
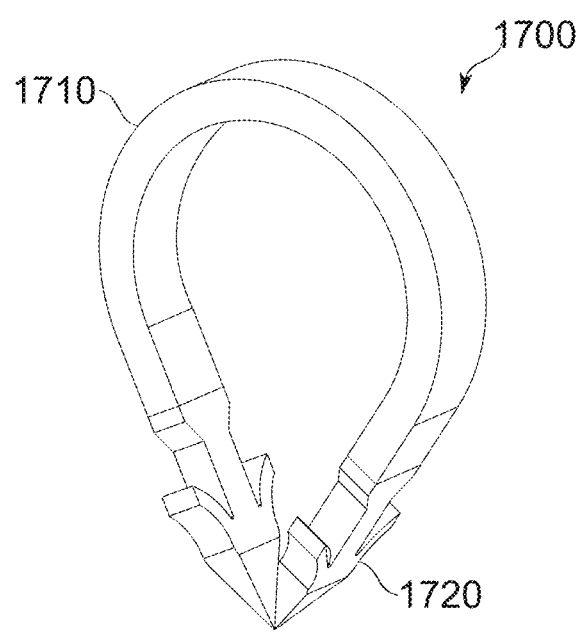

Reference is now made to FIGS. 17A-17B, which show a self-securing clip 100 for securing two gastric wall parts to one another, according to some exemplary embodiments of the invention.

In some embodiments, self-securing clips are provided to join two stomach walls together along a line of approximation to form a gastric sleeve. FIG. 17B shows an exemplary nitinol clip (clip 1700) at its "natural" (unconstrained) shape—a body 1710 curved into a tight loop or U shape. FIG. 17A shows clip 1700 straightened, which it can be constrained to do bending the ends apart from one another. As shown, clip 1700 has sharp tips 1722 at end of short tip shafts 1720, which enables penetration of the ends of the clip into the gastric wall. Barbs 1724, once they have penetrated, help to assure continued fixation into penetrated tissue.

Figure 18A:
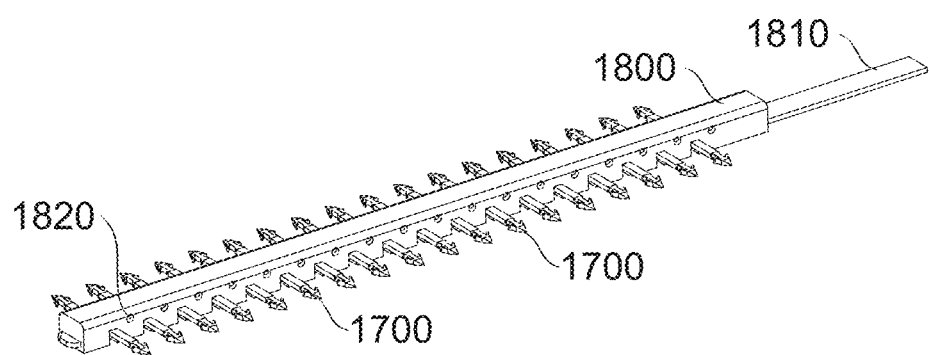
FIGS. 18A-18B show a distal segment of a delivery system comprising a row of self-securing clips for securing two gastric wall parts to one another, according to some exemplary embodiments of the invention.
Figure 18B:
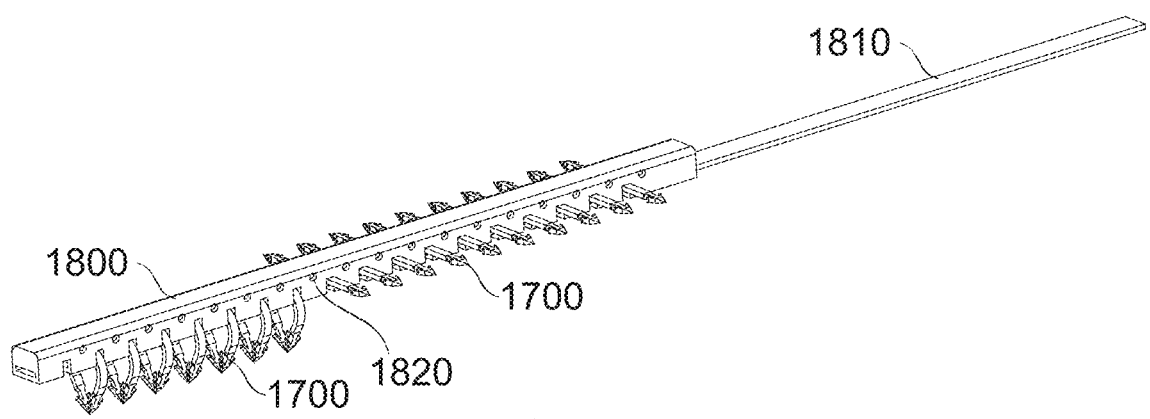

Reference is now made to FIGS. 18A-18B, which show a distal segment of a delivery system comprising a row of self-securing clips 1700 for securing two gastric wall parts to one another, according to some exemplary embodiments of the invention.

In some embodiments, a delivery system for clips 1700 comprises a shaft 1800 and a locking strip 1810. In some embodiments, the space between locking strip 1810 and shaft 1800 is restricted, such that clips 1700, contained in that space, are locked (constrained) into a straightened position in between them (FIG. 18A).

FIG. 18B shows the same shaft 1800 and locking strip 1810 during a process of releasing clips 1700. As strip 1810 is pulled proximally, clips 1700 are sequentially released from their constraints. This frees them to self-shape to their natural curved configuration. Shown is a stage in which seven distal clips 1700 are released, while the rest remain locked.

In some embodiments, shaft 1800 includes vacuum ports 1820 in between the clips. Optionally, vacuum applied to the shaft helps to pull tissue into apposition, impaling it to the sharp ends 1722 of the clips 1700, resulting in clip fixation.

Reference is now made to FIGS. 19A-19F, which show details of the construction of a shaft 1800 of a delivery system for self-securing clips 1700, according to some exemplary embodiments of the invention.

Figure 19A:
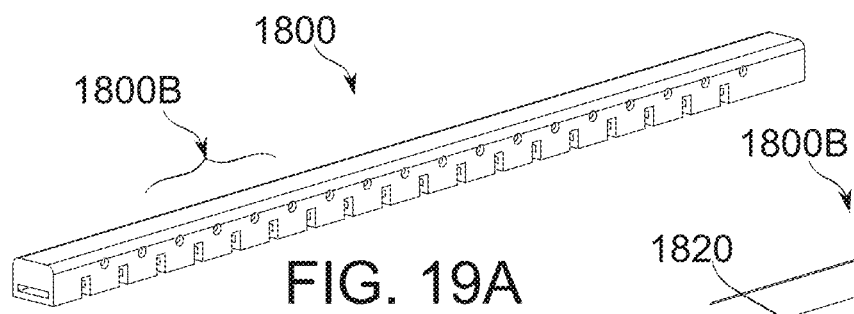
FIGS. 19A-19F show details of the construction of a shaft of a delivery system for self-securing clips, according to some exemplary embodiments of the invention.
Figure 19B:
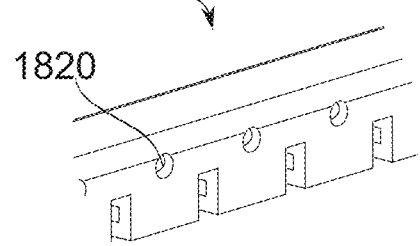

FIGS. 19A-19B illustrate shaft 1800 from a perspective side view: overall (FIG. 19A), and in detail (FIG. 19B) for region 1800B. The positions of vacuum ports 1820 are indicated.

Figure 19C:
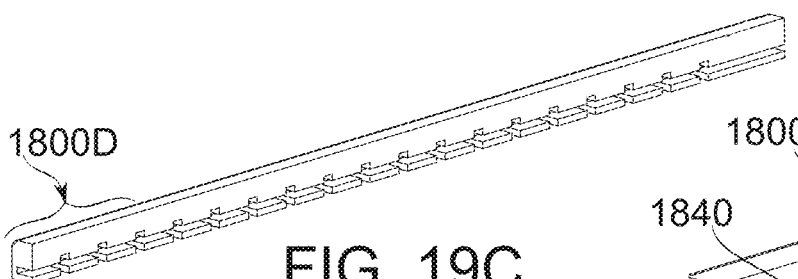
Figure 19D:
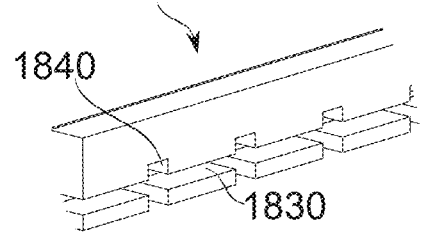

FIGS. 19C-19D illustrate median vertical cross-sections of shaft 1800, and, in particular, detail of region 1800D. Shaft 1800 includes longitudinal slit/hole 1830, through which strip 1810 slides. Grooves 1840 located along slit 1830 are sized to contain and geometrically lock clips 1700.

Figure 19E:
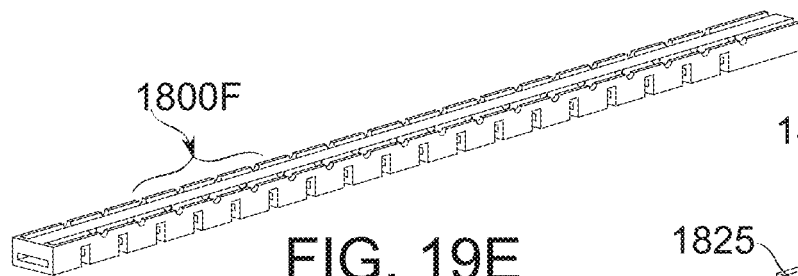
Figure 19F:
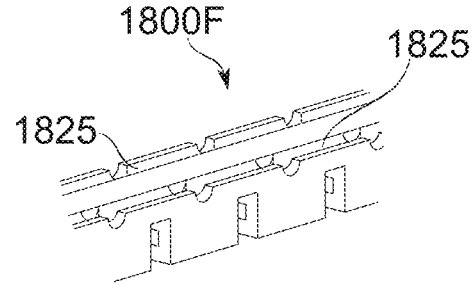

FIGS. 19E-19F show (in horizontal cross-section) vacuum canals 1825, which connect to vacuum ports 1820 along the sides, and, in particular, detail of region 1800F.

Figure 20A:
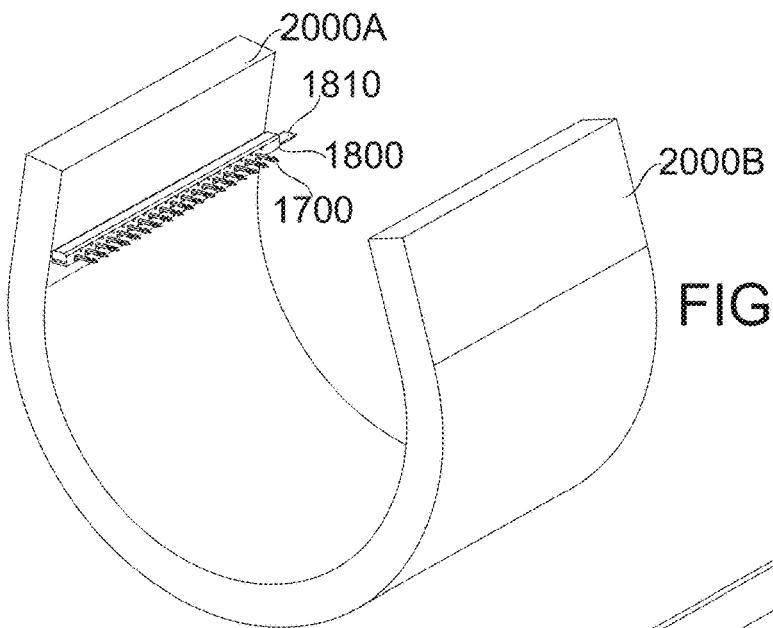
FIGS. 20A-20C demonstrate a sequence of approximating a segment of the stomach's walls, according to some exemplary embodiments of the invention.
Figure 20B:
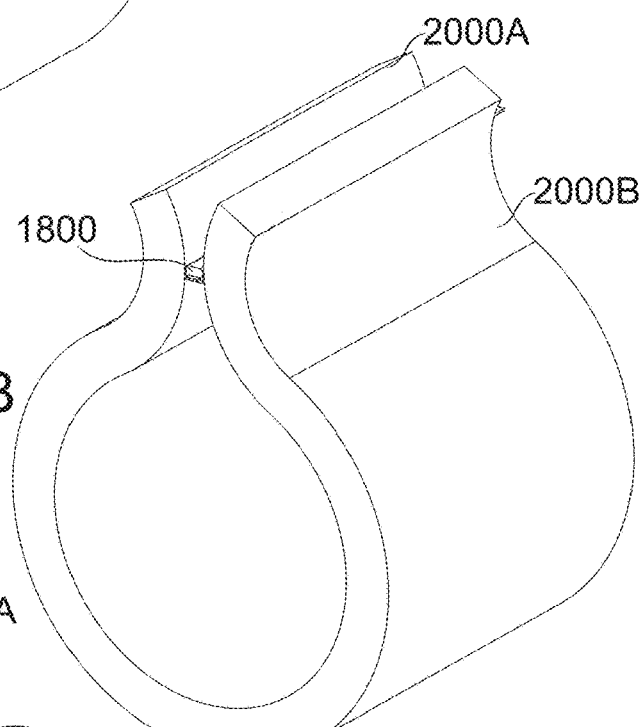
Figure 20C:
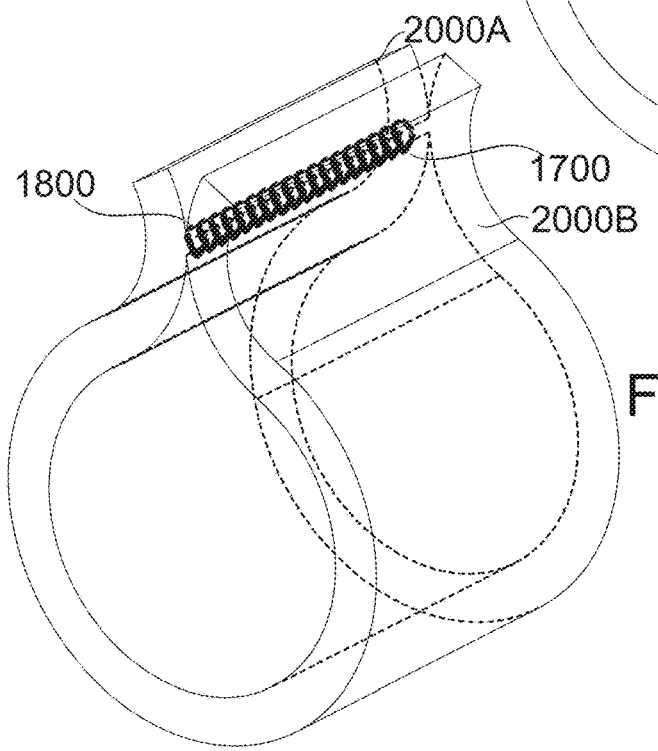

In some embodiments, there are two vacuum canals 1825 which are independently operable. Potentially, this allows grabbing gastric wall tissue in sequence—first by applying vacuum to one side and impaling a first wall region, then by applying vacuum to the other side, and impaling a second wall region. Reference is now made to FIGS. 20A-20C, which demonstrate a sequence of approximating a segment of the stomach's walls, according to some exemplary embodiments of the invention.

In FIG. 20A, device 1800 is shown fixated to a first wall 2000A. Fixation occurs, for example, upon applying a vacuum in the adjacent vacuum canal to impale nearby tissue upon clips 1700. In FIG. 20B, device 1800 is shown additionally fixated to the second wall 2000B, after approximation to the wall, and application of vacuum in the second canal. In FIG. 20C, strip 1810 has been pulled, allowing clips 1700 to bend and self-secure, and the delivery system removed. The walls 2000A, 2000B are left clipped (FIG. 20C).

For simplicity, the drawings show a straight shaft segment. It is to be understood, however, that the delivery system, in some embodiments, comprises a curved shaft. For example, the shaft is curved to more naturally follow the curvature of the gastric anatomy.

Figure 21A:
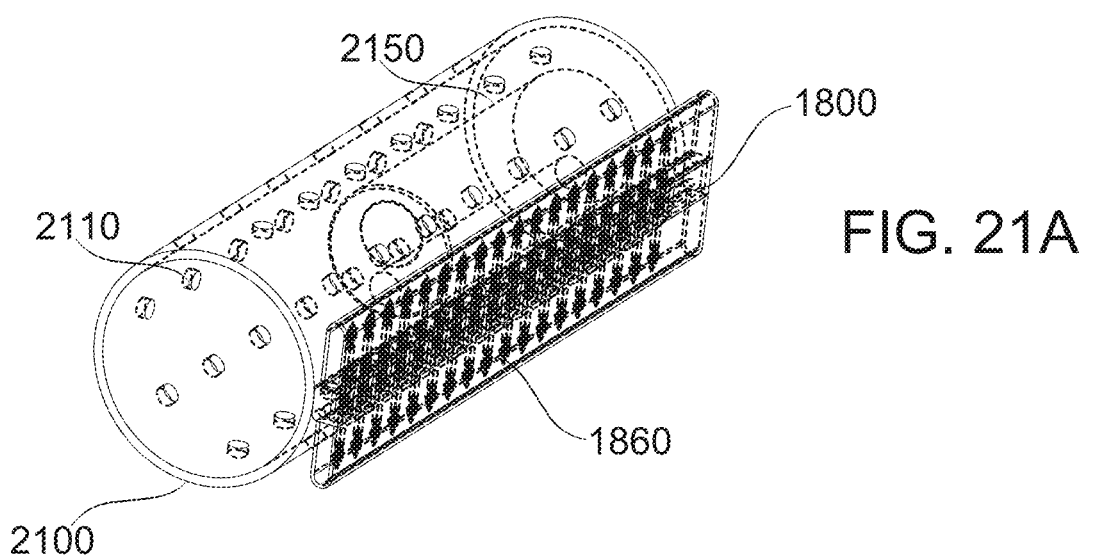
FIGS. 21A-21C demonstrate a clipping device integrated with conventional gastrointestinal means such as bougie and endoscope/gastroscope, according to some exemplary embodiments of the invention.
Figure 21B:
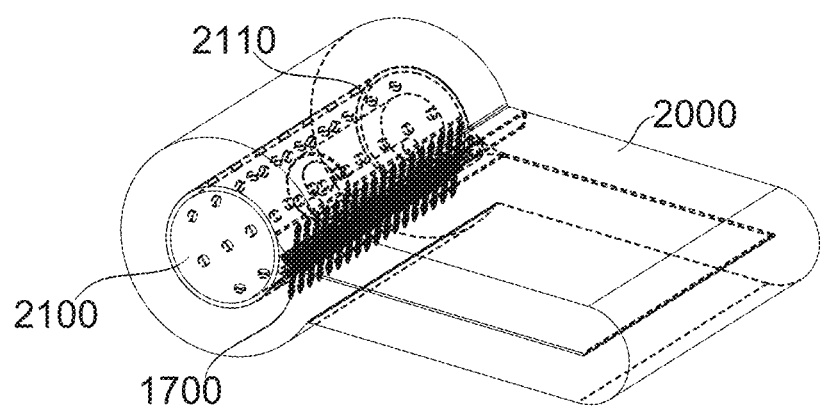
Figure 21C:
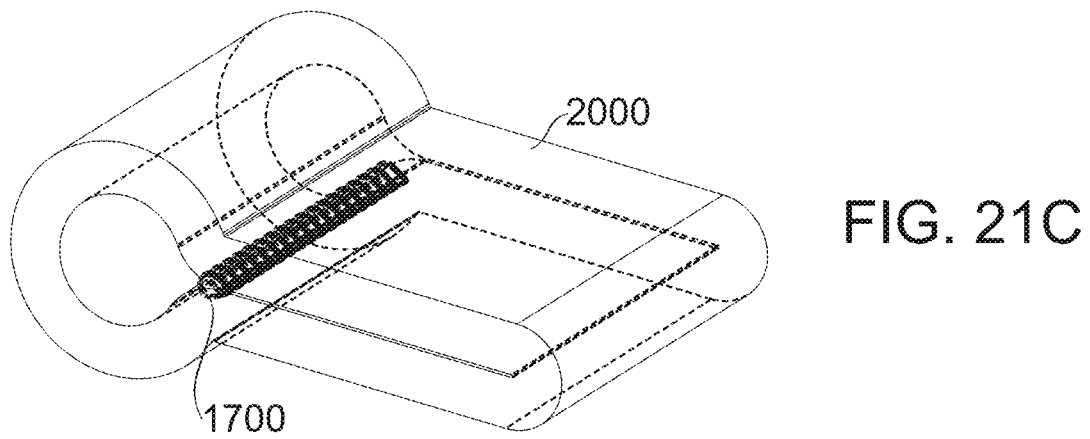

Reference is now made to FIGS. 21A-21C, which demonstrate a clipping device integrated with conventional gastrointestinal means such as bougie and endoscope/gastroscope, according to some exemplary embodiments of the invention.

In some embodiments (FIG. 21A), shaft 1800 is connected to bougie 2100 along one side of the bougie 2100. Optionally, removable covers 1860 are provided to cover the clips. This potentially enables transoral insertion into the stomach without scratching/injury of the gastrointestinal tract by the clips 1700. Optionally, bougie 2100 is made of a transparent material (for instance, polyethylene, cyclic olefin copolymer, polycarbonate, polyolefin, polyurethane, fluorinated ethylene propylene, polyethylene terephthalate, or another polymer) which assists operator visualization during operation of a gastroscope 2150 placed inside its lumen.

In some embodiments, bougie 2100 is perforated by holes 2110, which enable applied vacuum suction to pull and place the gastric wall around the circumference of bougie 2100. The vacuum inside holes 2110 is transmitted, for example, by suction applied to an aperture of bougie lumen 2110, by applying suction through a working channel of gastroscope 2150, and/or by canals (not shown) embedded along a wall of bougie 2100.

After the clipping device is inserted into the stomach (FIG. 21B), the physician optionally switches vacuum on and off (while maintaining covers 1860) repeatedly, together with movements of the device, until the device is well positioned.

Afterwards (FIG. 21C) the physician removes covers 1860, accessing them, for example, from a distal aperture of bougie 2100, and/or releasing a catch accessible from within the bougie 2100. Cover release exposes clips 1700 which penetrate (optionally assisted by a vacuum force which pulls the tissue) into the gastric walls 2000. In FIG. 21C, as previously described, strip 1810 has been pulled, clips 1700 are released, and an intra-gastric sleeve created. In some embodiments, a single long clipping device is used to clip the entire gastric sleeve at once. In some embodiments, clipping devices are separately applied in segments along the gastric sleeve.

Figure 22A:
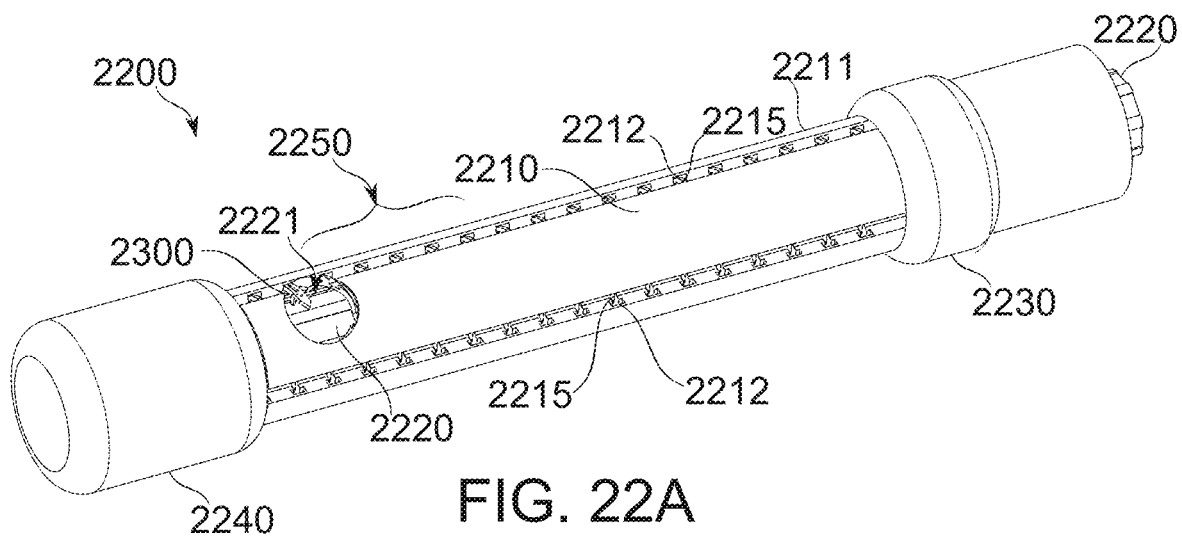
FIGS. 22A-22B illustrate a semi-automatic suturing device, according to some exemplary embodiments of the invention.
Figure 22B:
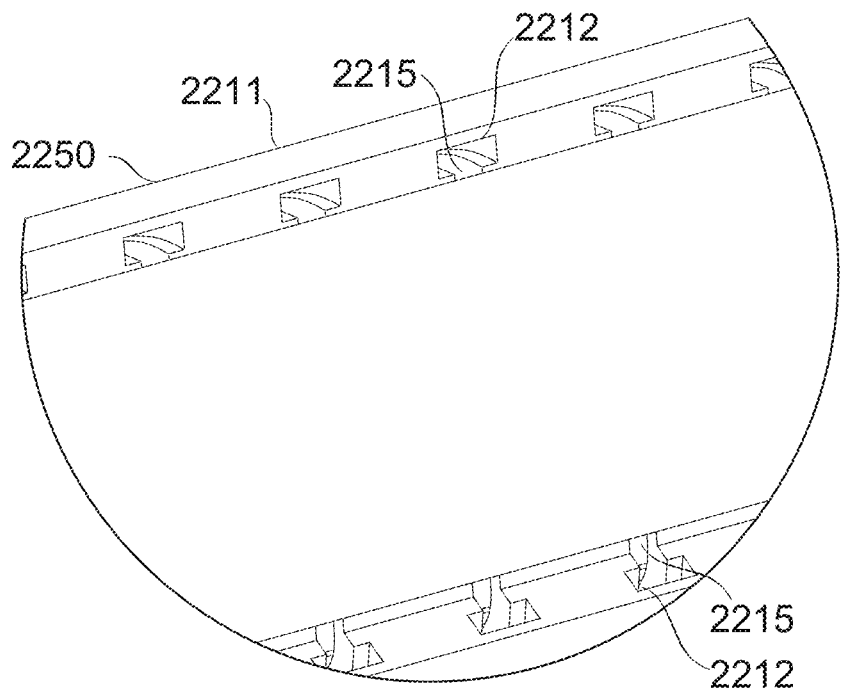

Reference is now made to FIGS. 22A-22B, which illustrate a semi-automatic suturing device 2200 for driving a needle along a partially open spiral path, and repeatedly through tissue fixed to the device, according to some exemplary embodiments of the invention. FIG. 22B shows additional detail of region 2250 of FIG. 22A.

In some embodiments, the suturing device 2200 comprises casing tube 2210 and driving tube 2220. It should be noted that in the drawing, a portion 2221 of casing tube 2210 is shown in cutaway to allow visualization of the driving tube 2220 underneath. Optionally, one or both of tubes 2210, 2220 are polymer made, and substantially transparent. Potentially, this allows endoscopic visualization from within their lumen. In some embodiments, casing tube 2210 comprises an outer jacket 2211 which partially wraps the circumference of casing tube 2210 (for example, between 230°-300° of the circumference; as shown, about 270° of the circumference).

In some embodiments, the jacket 2211 comprises a plurality of longitudinal slits 2212, to which the gastric wall is drawn to be grasped (for example, by applying of vacuum). In some embodiments, jacket 2211 comprises a helical slot 2215, which is optionally partially or fully interrupted around the circumference of the casing tube 2210 at the boundaries of jacket 2211. In some embodiments, helical slot 2215 and longitudinal slits 2212 occupy common lumens. In some embodiments, they comprise separate channels.

In some embodiments, a needle 2300 is provided, sized for travelling around helical slot 2215. The needle 2300 is connected with a suture thread. Where needle 2300 exits the jacket 2211, it potentially encounters tissue, such as gastric wall tissue suctioned to the device. A potential advantage of combining the lumens of slot 2215 and slits 2212 is to enhance fixation at the direct point of penetration by needle 2300.

Optionally, the device comprises a proximal balloon 2230 and/or distal balloon 2240, for sealing (against vacuum) and/or fixation.

Figure 23A:
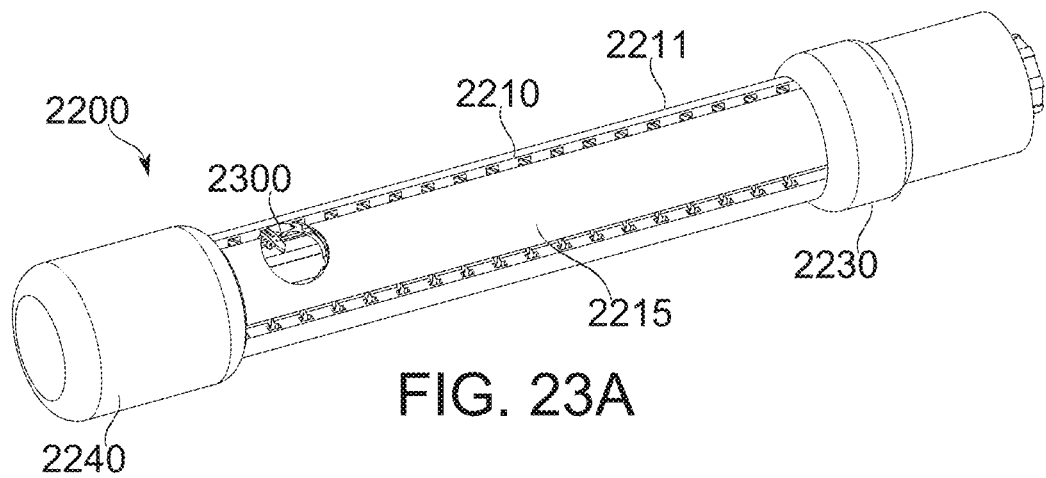
FIGS. 23A-23D demonstrate the driving mechanism of a suturing needle, according to some exemplary embodiments of the invention.
Figure 23B:
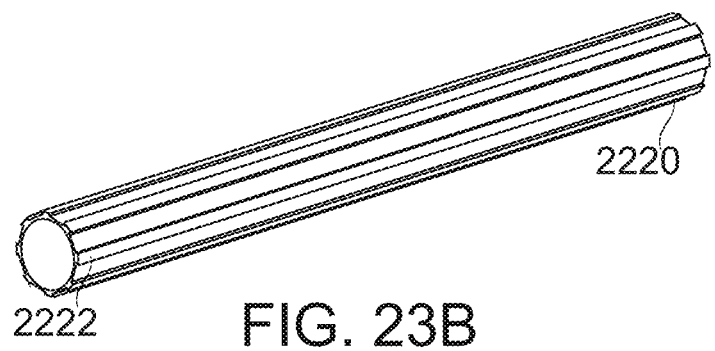
Figures 23C, 23D:
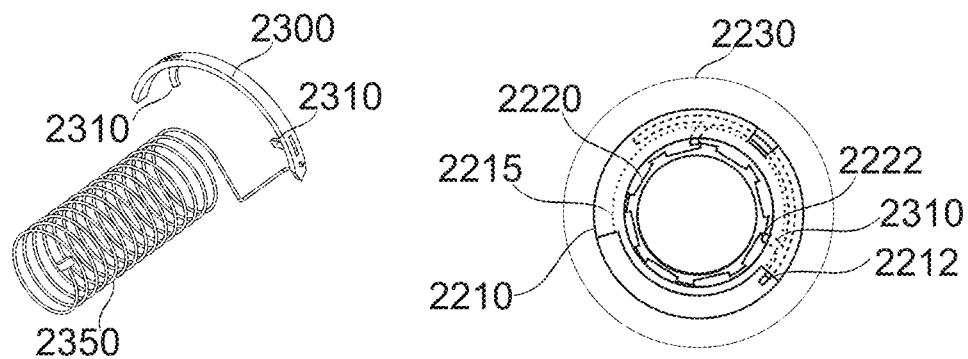

Reference is now made to FIGS. 23A-23D, which demonstrate the driving mechanism of a needle 2300, according to some exemplary embodiments of the invention. FIG. 23A repeats the structure of device 2200 shown in FIG. 22A, for ease of reference. FIGS. 23B-23C comprise illustrations of components of device 2200. FIG. 23D schematically illustrates a cutaway view of device 2200, looking longitudinally along the axis of driving tube 2220 at a level which the needle 2300 occupies.

In some embodiments, needle 2300 is connected to thread 2350, which is stored, for example, underneath balloon 2240. In some embodiments, needle 2300 comprises a plurality of flexible latches 2310. Upon rotation of driving tube 2220, longitudinal protrusions 2222 of the driving tube 2220 push on flexible latches 2310, driving needle 2300 along helical groove 2215 and through the tissue being held along longitudinal slits 2212.

Operation begins with the system placed inside the gastric cavity, for example, under visualization. Visualization is performed by, for example, under fluoroscopy or by using an endoscope (optionally a videoscope-type endoscope) inside the system, and/or another imaging method. In some embodiments, the operator then deploys the proximal (2230) and distal (2240) balloons to seal the gastric inlet and outlet. Potentially, this enhances stability when applying vacuum through the device lumen and its grooves. Upon application of vacuum, the stomach shrinks against the suturing device 2200, for example, substantially as shown in FIG. 21B: gastric wall tissue surrounds the device, with excess tissue collapsed.

As the gastric walls collapse around casing tube 2210 and jacket 2211, the gap in the jacket 2211 is also filled in, and tissue brought to the exit apertures of longitudinal slits 2215. Upon rotation of driving tube 2220, needle 2300 is forced into the gastric wall tissue. The needle is long enough that the tip passes back into the jacket before the other end exits, assuring continuous containment of the needle. The driving latches 2310 are spaced along the needle 2300 such that while one is outside the suture device (in the tissue, for example), at least one other latch is within the device and usable for driving the needle 2300. The depth of the jacket and/or the position of the exiting needle 2300 from slits 2215 determines the depth at which the suture needle will pass through the tissue.

The needle is driven continuously around the device, until a sufficient length of the gastric sleeve is sutured. If performed under visualization, the operator can make the decision based on direct visualization. Alternatively, a predetermined number of rotations are made. The pitch of slits 2215 is, for example, between 0.8 cm and 2 cm, or another greater, larger, or intermediate pitch, according to the distance at which sutures are to be made.

After suturing, the operator removes the suturing device. In some embodiments, the suturing device 2200 is removable in pieces, to prevent suturing-in of the device during operation. For example, driving tube 2220 and/or casing tube are removable separately from jacket 2211. In some embodiments, the floor (in the jacket 2211) of slits 2215 are open, allowing it to separate from the suture thread upon removal.

Freed from the device, suturing thread 2350 is tightened, approximating and/or ensuring continued approximation of the gastric walls to each other. Optionally, a locking element is passed over the thread and secured to maintain a tight suture. In some embodiments, a barbed suture is used to maintain fixation. The result is an intralumenally-created gastric sleeve, created without a requirement for making a surgical opening.

As used herein, the term "about" refers to within ±10%.

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A bougie for shaping a stomach portion to receive sutures, comprising:
    a body comprising a bendable portion and a lumen;
    a plurality of fenestrations to said lumen within said bendable portion of said body;
    a blocker coupled to said body and moveable with respect to said body and said plurality of fenestrations within said body, and comprising a portion positionable with respect to said body to:
        divide said plurality of fenestrations, each into two portions; and
        be moved to merge said two portions, after suturing, thereby allowing release of said bougie from sutures crossing between said fenestration portions and crossing said blocker inside said lumen.

2. The bougie of claim 1, wherein said blocker portion is positionable with respect to said body to block at least one fenestration of said plurality of fenestrations entirely.

3. The bougie of claim 1, wherein said body extends longitudinally, and said plurality of fenestrations are longitudinally distributed along said body;
    wherein said blocker is moveable in a longitudinal direction.

4. The bougie of claim 1, wherein said blocker is moveable laterally with respect to said body.

5. The bougie of claim 1, wherein said blocker is moveable by rotation with respect to said body.

6. The bougie of claim 1, wherein said blocker is a strip running through a center of said plurality of fenestrations.

7. The bougie of claim 1, wherein said bougie is provided as a system including a connection to a vacuum source configured to apply vacuum at said plurality of fenestrations to collapse said stomach portion on said bougie.

8. The bougie of claim 7, comprising one or more expandable elements to seal some or all of said stomach portion to said vacuum.

9. The bougie of claim 8, said one or more expandable elements comprising a proximal expandable element and a distal expandable element spaced apart a distance suitable for sealing said stomach portion while vacuum is applied to said stomach portion via said plurality of fenestrations in said bougie.

10. The bougie of claim 7, wherein said vacuum is 0.4-0.6 bar.

11. The bougie of claim 1, wherein said plurality of fenestrations are sized to receive and position a thickness of gastric tissue for suturing from within said lumen.

12. The bougie of claim 1, wherein said body has a curved longitudinal axis in a resting state thereof.

13. The bougie of claim 1, comprising a guide channel for passage of a needle suturing stomach tissue drawn into said lumen.

14. The bougie of claim 13, wherein said guide channel forms a spiral track for a needle, along a length of said bougie.

15. The bougie of claim 14, wherein said needle is helical.

16. The bougie of claim 1, wherein said plurality of fenestrations are arranged along a longitudinal axis of the body, closed on both a proximal and a distal side of the arrangement, and each sized to admit two externally separated portions of tissue therethough upon application of vacuum to the lumen.

17. The bougie of claim 1, wherein said plurality of fenestrations are separated along a longitudinal extent of the lumen to admit tissue in separately folded and arranged portions, each positioned by its arrangement to receive suturing from a needle passing within the lumen;
wherein each of said two portions of each fenestration is itself sized to admit a separately folded portion of tissue; and
wherein merging said two portions of each fenestration after suturing releases the bougie from sutures crossing between said folded portions of tissue and between said two portions of each fenestration.

18. The bougie of claim 1, wherein said blocker is configured to move to separately merge two portions of a first of said plurality of fenestrations, while two portions of a second of said plurality of fenestrations remains divided.

19. The bougie of claim 1, wherein said blocker is supported in regions separating adjacent fenestrations.

20. A method of intralumenally suturing a gastric sleeve, comprising:
inserting into a stomach a bougie comprising:
a body comprising a bendable portion and a lumen,
a plurality of fenestrations to said lumen within said body, and
a blocker coupled to said body and moveable with respect to said body and said plurality of fenestrations;
wherein said blocker comprises a portion positionable with respect to said body to:
divide said plurality of fenestrations, each into two respective portions, and
be moved to merge said two respective portions;
drawing vacuum through said bougie, such that stomach tissue is drawn to said body, wrapped around said body, and partially intruded into said plurality of fenestrations; and
moving said blocker to gradually one or more of:
divide said plurality of fenestrations each into said two respective portions; and
merge said divided fenestrations of said plurality of fenestrations.

21. The method of claim 20, wherein said moving merges said divided fenestrations and comprises withdrawing said blocker.

22. The method of claim 20, wherein said moving comprises rotating said blocker.

23. The method of claim 20, comprising suturing said stomach tissue which has been drawn into said body of said bougie.

24. The method of claim 23, wherein said moving is before, during or after said suturing.

25. The method of claim 20, wherein moving said blocker gradually divides or merges said plurality of fenestrations through a sequence that leaves at least a first of said plurality of fenestrations divided while a second of said plurality of fenestrations is merged.

* * * * *